United States Patent
Osswald et al.

(10) Patent No.: US 10,822,627 B2
(45) Date of Patent: Nov. 3, 2020

(54) MUTANTS OF HYDANTOINASE

(71) Applicant: EVONIK TECHNOCHEMIE GMBH, Dossenheim (DE)

(72) Inventors: Steffen Osswald, Nidderau (DE); Heiko Schuster, Hanau (DE); Jurgen Roos, Freigericht (DE); Andreas Karau, Geinhausen (DE); Ulrich Schwaneberg, Klemis-Hergenrath (BE); Ronny Martinez, Aachen (DE); Hemanshu Mundhada, Lyngby (DK); Ursula Holter, Willich (DE)

(73) Assignee: Evonik Operations GmbH, Essen (DE)

(*) Notice: Subject to any disclaimer, the term of this patent is extended or adjusted under 35 U.S.C. 154(b) by 36 days.

(21) Appl. No.: 15/952,377

(22) Filed: Apr. 13, 2018

(65) Prior Publication Data

US 2018/0237814 A1    Aug. 23, 2018

Related U.S. Application Data

(62) Division of application No. 14/357,028, filed as application No. PCT/EP2012/072891 on Nov. 16, 2012, now Pat. No. 9,957,536.

(30) Foreign Application Priority Data

Nov. 16, 2011 (EP) .................................. 11189395

(51) Int. Cl.
| | | |
|---|---|---|
| *C12N 15/55* | (2006.01) | |
| *C12N 9/86* | (2006.01) | |
| *C12P 13/22* | (2006.01) | |
| *C12P 13/04* | (2006.01) | |
| *C12P 41/00* | (2006.01) | |

(52) U.S. Cl.
CPC .............. *C12P 13/227* (2013.01); *C12N 9/86* (2013.01); *C12P 13/04* (2013.01); *C12P 41/009* (2013.01); *C12Y 305/02002* (2013.01)

(58) Field of Classification Search
None
See application file for complete search history.

(56) References Cited

FOREIGN PATENT DOCUMENTS

JP    2007189949 A    8/2007
WO    00/58449 A1    10/2000

OTHER PUBLICATIONS

Maniatis et al. "Molecular Cloning: A Laboratory Manual", pp. 387-389 (Year: 1982).*
Guo et al., "Protein Tolerance to Random Amino Acid Change", PNAS 101(25): 9205-9210. (Jun. 2004).
Database Geneseq [Online] Feb. 12, 2001, "Arthrobacter hydantoinase mutant protein V154A", retrieved from EBI accession No. GSP:AAB26141 Database accession No. AAB26141.
May et al. "Substrate-dependent enantioselectivity of a novel hydantoinase from Arthrobacter aurescens DSM 3745: Purification and characterization as new member of cyclic amidases", Journal of Biotechnology 61:1-13. (1998).
Cheon et al., "Manipulation of the Active Site Loops of o-Hydantoinase, a (f3/a)s-Barrel Protein, for Modulation of the Substrate Specificity", Biochemistry, American Chemical Society, US, vol. 43, No. 23, Jun. 15, 2004, pp. 7413-7420.
Xu et al., "Crystal Structure of o-Hydantoinase from Burkholderia pickettii at a Resolution of 2.7 Angstroms: Insights into the Molecular Basis of Enzyme Thermostability". Journal of Bacteriology, vol. 185, No. 14, Jul. 1, 2003, pp. 4038-4049.
Lee et al., "Designing the substrate specificity of o-hydantoinase using a rational approach", Enzyme and Microbial Technology, Stoneham, MA, US, vol. 44, No. 3, Mar. 5, 2009, pp. 170-175.

* cited by examiner

*Primary Examiner* — Rebecca E Prouty
(74) *Attorney, Agent, or Firm* — Reed Smith LLP; Ryan P. Cox

(57) ABSTRACT

The present invention relates to a hydantoinase having an amino acid sequence selected from (i) or (ii), with (i) amino acid sequence selected from SEQ ID NO: 6-20 and SEQ ID NO: 73-119 (ii) amino acid sequence wherein in the amino acid sequence of SEQ ID NO: 6-20 and SEQ ID NO: 73-119, 1 to 75 amino acid residues have been substituted, deleted, inserted and/or added, and wherein further the catalytic activity of the hydantoinase is higher by a factor of at least 1.2 than the catalytic activity of the hydantoinase having amino acid sequence SEQ ID NO: 1. The present invention further relates to a process for preparing amino acids, wherein said hydantoinase is used.

6 Claims, 1 Drawing Sheet

Specification includes a Sequence Listing.

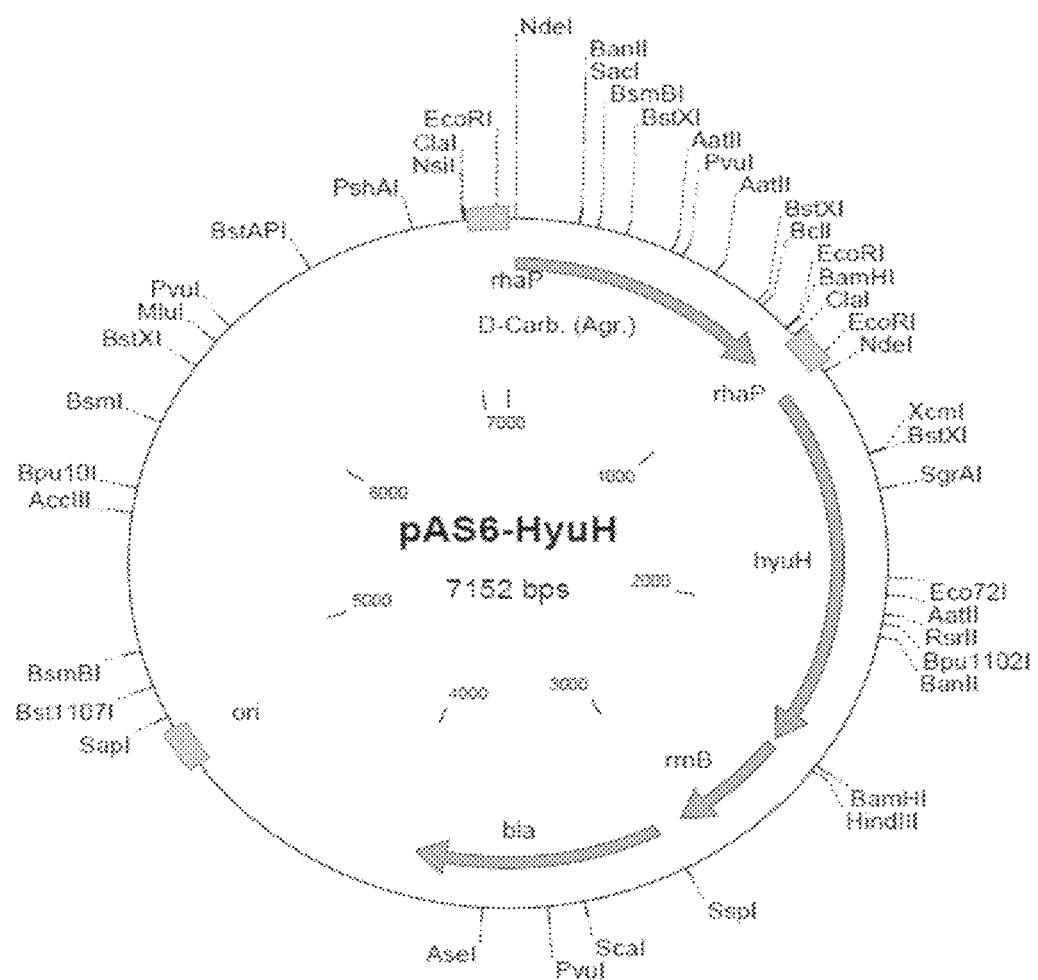

MUTANTS OF HYDANTOINASE

This application is a divisional of U.S. patent application Ser. No. 14/357,028, filed May 8, 2014, now U.S. Pat. No. 9,957,536, which is a United States national stage of International Application No. PCT/EP2012/072891, filed Nov. 16, 2012, which claims benefit of European Patent Application No. 11189395.4, filed Nov. 16, 2011, each of which are herein incorporated by reference in their entirety.

The present invention relates generally to hydantoinases. More particularly, the present invention refers to a series of modified hydantoinases which exhibit increased enzymatic activities relative to previously isolated hydantoinases and their use in processes for preparing amino acids, in particular their use in whole-cell catalysts.

DESCRIPTION OF RELATED ART

Processes for producing amino acids using enzymes are known. Further, there are processes which involve the asymmetric decomposition of chemically inexpensively synthesized 5-substituted hydantoin compounds as the starting material into optically active amino acids. These processes of producing optically active amino acids from 5-substituted hydantoin compounds are important for production of pharmaceutical preparations, products in chemical industry, food additives etc.

In this process of producing amino acids from 5-substituted hydantoin compounds, two enzymes are necessary: (1) an enzyme referred to as hydantoinase (hydantoin hydrolyzing enzyme) which is catalyzing the reaction of forming N-carbamoylamino acid by transforming a 5-substituted hydantoin compound into the respective N-carbamoylamino acid by hydrolysis; (2) an enzyme referred to as N-carbamoylamino acid hydrolase which is catalyzing the reaction of forming an optically active amino acid by transforming the N-carbamoylamino acid mentioned before into the respective amino acid by hydrolysis.

Hydantoin hydrolyzing enzymes, which will be referred here as 'hydantoinases', comprise a diverse class of enzymes having a wide range of specificities and biological functions. An important property of hydantoinases is their enantioselectivity which makes them valuable for the production of optically pure D- or L-amino acids. For producing optically active amino acids from 5-substituted hydantoin compounds, hydantoinase and/or N-carbamoylamino acid hydrolase must be an enantioselective enzyme. Processes of producing L-amino acids by an L-amino acid-producing microorganism or by enzyme-containing materials produced by the microorganism have been described, wherein microorganisms of diverse genera such as *Flavobacterium, Bacillus, Pseudomonas* and *Arthrobacter* (J. Biotechnol. 46, 63, 1996) were employed.

A hydantoinase gene and an N-carbamoylamino acid hydrolase gene have been isolated from a microorganism of the genus *Arthrobacter*, and recombinant proteins encoded by these genes were used to produce L-amino acids.

In view of the importance of hydantoinases to the production of optically pure amino acids, there has been a concentrated effort to develop modified enzymes which have improved properties with respect to amino acid production. As a result of this effort, a number of microorganisms have been isolated and identified which produce hydantoinases with desirable enzymatic properties. U.S. Pat. No. 5,516,660 discloses *Arthrobacter* sp. strains which produce hydantoinases that are capable of producing L-alpha-amino acids from D-, L- and/or D,L-5-monosubstituted hydantoins.

A more recent development is the production of D- and L-amino acids on an industrial scale from the respective hydantoin utilizing whole cell catalyst technology (WO 2002/077212, WO 20041042047, WO 2000/058449, WO 2003/042412). The catalyst contains D-hydantoinase, hydantoin racemase and D-carbamoylase co-expressed in a microorganism such as *E. coli*.

The international patent application WO 00/58449 discloses mutants of hydantoinase derived from *Arthrobacter* resulting in an increase of activity of about 40%.

The testing of these standard catalysts derived from *Arthrobacter* sp. available showed that the production of D-tryptophan from the respective tryptophan hydantoin is possible but with very low transformation rates. The low transformation rate is due to the insufficient property of the available wild-type *Arthrobacter* sp. hydantoinase to accept tryptophan hydantoin as substrate.

The aim of the present invention was the provision of hydantoinase having increased transformation rates in respect of 5-substituted hydantoin, preferably tryptophan hydantoin and a process for the production of amino acids, preferably D-tryptophan, in particular starting from L-tryptophan hydantoin using hydantoin racemase, hydantoinase and carbamoylase, preferably co-expressed in an *E. coli* host.

Therefore, the object of the present invention was to provide an improved hydantoinase with enhanced transformation rates, in particular with enhanced transformation rates in respect of tryptophan hydantoin. In addition, it could be beneficial to increase the enantioselectivity of the hydantoinase.

SUMMARY OF THE PRESENT INVENTION

The object of the present invention is solved by a hydantoinase having an amino acid sequence selected from (i) or (ii), with
  (i) amino acid sequence selected from SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82. SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, or SEQ ID NO: 119,
  (ii) amino acid sequence wherein in the amino acid sequence of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, or SEQ ID NO: 119, 1 to $\varphi$ amino acid residues have been substituted, deleted, inserted and/or added, and wherein $\varphi$ is defined as $\varphi=75$, and wherein further the catalytic activity of the hydantoinase is higher by a factor of at least $\zeta$ than the catalytic activity of the hydantoinase having amino acid sequence SEQ ID NO: 1, and wherein $\zeta$ is defined as $\zeta=1.2$.

In the context of the present invention, and if not defined otherwise, the catalytic activity of a hydantoinase is to be understood as the catalytic activity of this enzyme with respect to the transformation of a 5-substituted D-hydantoin compound to the corresponding D-carbamoylamino acid.

In the context of the present invention the enantioselectivity of a hydantoinase is defined as the ratio $D_{act}/L_{act}$, with $D_{act}$=the catalytic activity of this enzyme for the transformation of 5-substituted D-hydantoin compounds to the corresponding D-carbamoylamino acids, and $L_{act}$=the catalytic activity of this enzyme for the transformation of the enantiomers of the 5-substituted D-hydantoin compounds to the enantiomers of the corresponding D-carbamoylamino acids, in other words $L_{act}$=the catalytic activity of this enzyme for the transformation of the corresponding 5-substituted L-hydantoin compounds to the corresponding L-carbamoylamino acids.

In the context of the present invention the term addition of amino acids means addition of amino acid residues at the N-terminus or C-terminus of a polypeptide.

In preferred embodiments of the present invention $\varphi$ is selected from 70, 60, 50, 40, 30, 20, 10, 9, 8, 7, 6, 5, 4, 3, 2 or 1.

In further preferred embodiments of the present invention $\zeta$ is selected from 1.5, 2, 3, 4, 5, 10, 15, 20, 25 or 30.

In further preferred embodiments of the present invention $\varphi$ and $\zeta$ are selected as follows:

$\varphi=70$ and $\zeta=1.5$, $\varphi=70$ and $\zeta=2$, $\varphi=70$ and $\zeta=3$, $\varphi=70$ and $\zeta=4$, $\varphi=70$ and $\zeta=5$, $\varphi=70$ and $\zeta=10$, $\varphi=70$ and $\zeta=15$, $\varphi=70$ and $\zeta=20$, $\varphi=70$ and $\zeta=25$, $\varphi=70$ and $\zeta=30$, $\varphi=60$ and $\zeta=1.5$, $\varphi=60$ and $\zeta=2$, $\varphi=60$ and $\zeta=3$, $\varphi=60$ and $\zeta=4$, $\varphi=60$ and $\zeta=5$, $\varphi=60$ and $\zeta=10$, $\varphi=60$ and $\zeta=15$, $\varphi=60$ and $\zeta=20$, $\varphi=60$ and $\zeta=25$, $\varphi=60$ and $\zeta=30$, $\varphi=50$ and $\zeta=1.5$, $\varphi=50$ and $\zeta=2$, $\varphi=50$ and $\zeta=3$, $\varphi=50$ and $\zeta=4$, $\varphi=50$ and $\zeta=5$, $\varphi=50$ and $\zeta=10$, $\varphi=50$ and $\zeta=15$, $\varphi=50$ and $\zeta=20$, $\varphi=50$ and $\zeta=25$, $\varphi=50$ and $\zeta=30$, $\varphi=40$ and $\zeta=1.5$, $\varphi=40$ and $\zeta=2$, $\varphi=40$ and $\zeta=3$, $\varphi=40$ and $\zeta=4$, $\varphi=40$ and $\zeta=5$, $\varphi=40$ and $\zeta=10$, $\varphi=40$ and $\zeta=5$, $\varphi=40$ and $\zeta=20$, $\varphi=40$ and $\zeta=25$, $\varphi=40$ and $\zeta=30$, $\varphi=30$ and $\zeta=1.5$, $\varphi=30$ and $\zeta=2$, $\varphi=30$ and $\zeta=3$, $\varphi=30$ and $\zeta=4$, $\varphi=30$ and $\zeta=5$, $\varphi=30$ and $\zeta=10$, $\varphi=30$ and $\zeta=15$, $\varphi=30$ and $\zeta=20$, $\varphi=30$ and 25, $\varphi=30$ and $\zeta=30$, $\varphi=20$ and $\zeta=1.5$, $\varphi=20$ and $\zeta=2$, $\varphi=20$ and $\zeta=3$, $\varphi=20$ and $\zeta=4$, $\varphi=20$ and $\zeta=5$, $\varphi=20$ and $\zeta=10$, $\varphi=20$ and $\zeta=15$, $\varphi=20$ and $\zeta=20$, $\varphi=20$ and $\zeta=25$, $\varphi=20$ and $\zeta=30$, $\varphi=10$ and $\zeta=1.5$, $\varphi=10$ and $\zeta=2$, $\varphi=10$ and $\zeta=3$, $\varphi=10$ and $\zeta=4$, $\varphi=10$ and $\zeta=5$, $\varphi=10$ and $\zeta=10$, $\varphi=10$ and $\zeta=15$. $\varphi=10$ and $\zeta=20$, $\varphi=10$ and $\zeta=25$, $\varphi=10$ and $\zeta=30$, $\varphi=9$ and $\zeta=1.5$, $\varphi=9$ and $\zeta=2$, $\varphi=9$ and $\zeta=3$, $\varphi=9$ and $\zeta=4$, $\varphi=9$ and $\zeta=5$, $\varphi=9$ and $\zeta=10$, $\varphi=9$ and $\zeta=15$, $\varphi=9$ and $\zeta=20$, $\varphi=9$ and $\zeta=25$, $\varphi=9$ and $\zeta=30$, $\varphi=8$ and $\zeta=1.5$, $\varphi=8$ and $\zeta=2$, $\varphi=8$ and $\zeta=3$, $\varphi=8$ and $\zeta=4$, f$\varphi=8$ and $\zeta=5$, $\varphi=8$ and $\zeta=10$, $\varphi=8$ and $\zeta=15$, $\varphi=8$ and $\zeta=20$, $\varphi=8$ and $\zeta=25$, $\varphi=8$ and $\zeta=30$, $\varphi=7$ and $\zeta=1.5$, $\varphi=7$ and $\zeta=2$, $\varphi=7$ and $\zeta=3$, $\varphi=7$ and $\zeta=4$, $\varphi=7$ and $\zeta=5$, $\varphi=7$ and $\zeta=10$, $\varphi=7$ and $\zeta=15$, $\varphi=7$ and $\zeta=20$, $\varphi=7$ and $\zeta=25$, $\varphi=7$ and $\zeta=30$, $\varphi=6$ and $\zeta=1.5$, $\varphi=6$ and $\zeta=2$, $\varphi=6$ and $\zeta=3$, $\varphi=6$ and $\zeta=4$, $\varphi=6$ and $\zeta=5$, $\varphi=6$ and $\zeta=10$, $\varphi=6$ and $\zeta=15$, $\varphi=6$ and $\zeta=20$, $\varphi=6$ and $\zeta=25$, $\varphi=6$ and $\zeta=30$, $\varphi=5$ and $\zeta=1.5$, $\varphi=5$ and $\zeta=2$, $\varphi=5$ and $\zeta=3$, $\varphi=5$ and $\zeta=4$, $\varphi=5$ and $\zeta=5$, $\varphi=5$ and $\zeta=10$, $\varphi=5$ and $\zeta=15$, $\varphi=5$ and $\zeta=20$, $\varphi=5$ and $\zeta=25$, $\varphi=5$ and $\zeta=30$, $\varphi=4$ and $\zeta=1.5$. $\varphi=4$ and $\zeta=2$, $\varphi=4$ and $\zeta=3$, $\varphi=4$ and $\zeta=4$, $\varphi=4$ and $\zeta=5$, $\varphi=4$ and $\zeta=10$, $\varphi=4$ and $\zeta=15$, $\varphi=4$ and $\zeta=20$, $\varphi=4$ and $\zeta=25$, $\varphi=4$ and $\zeta=30$, $\varphi=3$ and $\zeta=1.5$, $\varphi=3$ and $\zeta=2$, $\varphi=3$ and $\zeta=3$, $\varphi=3$ and $\zeta=4$, $\varphi=3$ and $\zeta=5$, $\varphi=3$ and $\zeta=10$, $\varphi=3$ and $\zeta=15$, $\varphi=3$ and $\zeta=20$, $\varphi=3$ and $\zeta=25$, $\varphi=3$ and $\zeta=30$, $\varphi=2$ and $\zeta=1.5$, $\varphi=2$ and $\zeta=2$, $\varphi=2$ and $\zeta=3$, $\varphi=2$ and $\zeta=4$, $\varphi=2$ and $\zeta=5$, $\varphi=2$ and $\zeta=10$, $\varphi=2$ and $\zeta=15$, $\varphi=2$ and $\zeta=20$, $\varphi=2$ and $\zeta=25$, $\varphi=2$ and $\zeta=30$, $\varphi=1$ and $\zeta=1.5$, $\varphi=1$ and $\zeta=2$, $\varphi=1$ and $\zeta=3$, $\varphi=1$ and $\zeta=4$, $\varphi=1$ and $\zeta=5$, $\varphi=1$ and $\zeta=10$, $\varphi=1$ and $\zeta=15$, $\varphi=1$ and $\zeta=20$, $\varphi=1$ and $\zeta=25$, $\varphi=1$ and $\zeta=30$.

In accordance with the present invention, modified hydantoinases (hydantoin hydrolyzing enzymes) are provided which have enhanced catalytic activity as compared to the wild-type hydantoinase produced by the microorganism *Arthrobacter* sp. Hydantoinases of the present invention, further may have increased enantioselectivity as compared to the wild-type hydantoinase produced by the microorganism *Arthrobacter* sp. Hydantoinases according to the present invention exhibit enhanced transformation rates in respect of 5-substituted hydantoin compounds, in particular D-tryptophan hydantoin, and therefore are suitable in processes for the production of D-amino acids. Such processes preferably are suitable for the production of D-tryptophan starting from the respective tryptophan hydantoin in particular using D-hydantoinase, D-carbamoylase and optionally hydantoin racemase. These enzymes preferably are co-expressed in a microorganism such as *E. coli*. In this process of producing amino acids from 5-substituted hydantoin compounds the hydantoinase catalyzes the reaction of forming N-carbamoylamino acid by hydrolyzing a 5-substituted hydantoin compounds, preferably (D-tryptophan hydantoin), to give the respective N-carbamoylamino acids (preferably N-carbamoyl D-tryptophan). This N-carbamoylamino acid is hydrolyzed by N-carbamoylamino acid hydrolase to form the respective amino acid (preferably D-tryptophan).

For the preparation of tryptophan, as starting material also D,L-tryptophan hydantoin or L-tryptophan hydantoin may be used, wherein in particular the presence of hydantoin racemase is favourable in order to provide the D-tryptophan hydantoin substrate for the hydantoinase of the present invention. Such process preferably is suitable for the production of D-tryptophan starting from the respective D,L- or L-tryptophan hydantoin in particular using hydantoin racemase, D-hydantoinase and D-carbamoylase. These three enzymes preferably are co-expressed in a microorganism such as *E. coli*.

The person skilled in the art understands that the information given with respect to a specific amino acid position (e.g. 152) of a specific reference sequence can be transferred to variant hydantoinases and homologous amino acid sequences: the skilled person is able to align the reference amino acid sequence with a variant sequence and to determine the corresponding position (e.g. amino acid position 152) in the variant sequence. Referring to this example, the skilled person understands that in the variant sequence the amino acid position which corresponds to amino acid position 152 of the reference sequence, may not necessarily be the 152th amino acid residue of the variant amino acid sequence, however still has the same position in the three-dimensional structure of the variant enzyme. Methods for aligning amino acid sequences are described in further detail below. Other methods can also be employed in order to determine corresponding positions in a variant sequence compared to the reference sequence.

DESCRIPTION OF THE FIGURE

FIG. 1 shows the plasmid pAS6-HyuH containing the wild type gene hyuH expressing a hydantoinase having amino acid sequence SEQ ID NO: 1 and a gene expressing D-carbamoylase having amino acid sequence SEQ ID NO: 4. The abbreviations indicated in the plasmid map stand for the following elements: D-Carb.=D-carbamoylase gene NRRL, *Agrobacterium* sp.; rhaP=rhamnose promotor; hyuH=hydantoinase DSM9771; rmB=transcription terminator; bla=beta-lactamase; ori=origin of replication ColEI.

DESCRIPTION OF THE SEQUENCES

In the context of the present invention variants of polypeptide sequences are sometimes described by denoting each amino acid substitution present in the variant sequence in comparison with the original sequence in the format AA1XAA2, wherein AA1 denotes the amino acid residue present at position X in the original sequence and AA2 denotes the amino acid residue present at position X in the sequence of the variant.

SEQ ID NO: 1 shows the amino acid sequence of wild-type hydantoinase from *Arthrobacter* sp.

SEQ ID NO: 2 shows the nucleotide sequence encoding the wild-type hydantoinase from *Arthrobacter* sp.

SEQ ID NO: 3 shows the amino acid sequence of wild-type hydantoinase racemase from *Arthrobacter* sp.

SEQ ID NO: 4 shows the amino acid sequence of wild-type D-carbamoylase from *Arthrobacter* sp.

SEQ ID NO: 5 shows the amino acid sequence as reference, wherein amino acid residues X at positions 152, 64, 71, 72, 95, 154, 181, 284, 285, 398 and 452 are defined according to the claims and amino acid residue at position 152 represents any amino acid residue other than alanine.

SEQ ID NO: 6 shows the amino acid sequence of a variant hydantoinase wherein alanine at position 152 has been replaced by glycine.

SEQ ID NO: 7 shows the amino acid sequence of a variant hydantoinase wherein alanine at position 152 has been replaced by cysteine.

SEQ ID NO: 8 shows the amino acid sequence of a variant hydantoinase wherein alanine at position 152 has been replaced by serine.

SEQ ID NO: 9 shows the amino acid sequence of a variant hydantoinase wherein alanine at position 152 has been replaced by threonine.

SEQ ID NO: 10 shows the amino acid sequence of a variant hydantoinase wherein alanine at position 152 has been replaced by valine.

SEQ ID NO: 11 shows the amino acid sequence of a variant hydantoinase wherein alanine at position 152 has been replaced by serine and valine at position 154 has been replaced by isoleucine.

SEQ ID NO: 12 shows the amino acid sequence of a variant hydantoinase wherein alanine at position 152 has been replaced by valine and valine at position 154 has been replaced by cysteine.

SEQ ID NO: 13 shows the amino acid sequence of a variant hydantoinase wherein alanine at position 152 has been replaced by cysteine and valine at position 154 has been replaced by serine.

SEQ ID NO: 14 shows the amino acid sequence of a variant hydantoinase wherein arginine at position 71 has been replaced by asparagine and tyrosine at position 72 has been replaced by histidine and alanine at position 152 has been replaced by serine.

SEQ ID NO: 15 shows the amino acid sequence of a variant hydantoinase wherein arginine at position 71 has been replaced by asparagine and tyrosine at position 72 has been replaced by arginine and alanine at position 152 has been replaced by serine.

SEQ ID NO: 16 shows the amino acid sequence of a variant hydantoinase wherein arginine at position 71 has been replaced by valine and tyrosine at position 72 has been replaced by arginine and alanine at position 152 has been replaced by serine.

SEQ ID NO: 17 shows the amino acid sequence of a variant hydantoinase wherein arginine at position 71 has been replaced by serine and tyrosine at position 72 has been replaced by arginine and alanine at position 152 has been replaced by cysteine and valine at position 154 has been replaced by serine and valine at position 181 has been replaced by alanine.

SEQ ID NO: 18 shows the amino acid sequence of a variant hydantoinase wherein arginine at position 71 has been replaced by tyrosine and tyrosine at position 72 has been replaced by arginine and alanine at position 152 has been replaced by serine.

SEQ ID NO: 19 shows the amino acid sequence of a variant hydantoinase wherein arginine at position 71 has been replaced by leucine and alanine at position 152 has been replaced by cysteine and valine at position 154 has been replaced by serine.

SEQ ID NO: 20 shows the amino acid sequence of a variant hydantoinase wherein arginine at position 71 has been replaced by tyrosine and tyrosine at position 72 has been replaced by histidine and alanine at position 152 has been replaced by serine.

SEQ ID NOs: 21 to 72 show primer sequences used for the mutagenesis of a diversity of amino acid positions of hydantoinase as indicated in table 1.

SEQ ID NO: 73 shows the amino acid sequence of a variant hydantoinase carrying the following substitution as compared with SEQ ID NO: 1: I95H.

SEQ ID NO: 74 shows the amino acid sequence of a variant hydantoinase carrying the following substitution as compared with SEQ ID NO: 1: V154G.

SEQ ID NO: 75 shows the amino acid sequence of a variant hydantoinase carrying the following substitution as compared with SEQ ID NO: 1: V154N.

SEQ ID NO: 76 shows the amino acid sequence of a variant hydantoinase carrying the following substitution as compared with SEQ ID NO: 1: R71D.

SEQ ID NO: 77 shows the amino acid sequence of a variant hydantoinase carrying the following substitution as compared with SEQ ID NO: 1: R71E.

SEQ ID NO: 78 shows the amino acid sequence of a variant hydantoinase carrying the following substitution as compared with SEQ ID NO: 1: V284F.

SEQ ID NO: 79 shows the amino acid sequence of a variant hydantoinase carrying the following substitution as compared with SEQ ID NO: 1: V154A.

SEQ ID NO: 80 shows the amino acid sequence of a variant hydantoinase carrying the following substitution as compared with SEQ ID NO: 1: I64T.

SEQ ID NO: 81 shows the amino acid sequence of a variant hydantoinase carrying the following substitution as compared with SEQ ID NO: 1: I64V.

SEQ ID NO: 82 shows the amino acid sequence of a variant hydantoinase carrying the following substitution as compared with SEQ ID NO: 1: V154S.

SEQ ID NO: 83 shows the amino acid sequence of a variant hydantoinase carrying the following substitutions as compared with SEQ ID NO: 1: V154A, T398A, H452L.

SEQ ID NO: 84 shows the amino acid sequence of a variant hydantoinase carrying the following substitutions as compared with SEQ ID NO: 1: A152S, V154I.

SEQ ID NO: 85 shows the amino acid sequence of a variant hydantoinase carrying the following substitutions as compared with SEQ ID NO: 1: R71D, Y72H, A152S.

SEQ ID NO: 86 shows the amino acid sequence of a variant hydantoinase carrying the following substitutions as compared with SEQ ID NO: 1: R71V, Y72N, A152S.

SEQ ID NO: 87 shows the amino acid sequence of a variant hydantoinase carrying the following substitutions as compared with SEQ ID NO: 1: R71S, Y72N. A152C, V154S, V181A.

SEQ ID NO: 88 shows the amino acid sequence of a variant hydantoinase carrying the following substitutions as compared with SEQ ID NO: 1: R71D, Y72N, A152S.

SEQ ID NO: 89 shows the amino acid sequence of a variant hydantoinase carrying the following substitutions as compared with SEQ ID NO: 1: R71Y, Y72N, A152S.

SEQ ID NO: 90 shows the amino acid sequence of a variant hydantoinase carrying the following substitutions as compared with SEQ ID NO: 1: I64V, R71I, Y72N, A152S.

SEQ ID NO: 91 shows the amino acid sequence of a variant hydantoinase carrying the following substitutions as compared with SEQ ID NO: 1: I64C, R71Y, Y72N, A152S.

SEQ ID NO: 92 shows the amino acid sequence of a variant hydantoinase carrying the following substitutions as compared with SEQ ID NO: 1: I64C, R71D, Y72H, A152S.

SEQ ID NO: 93 shows the amino acid sequence of a variant hydantoinase carrying the following substitutions as compared with SEQ ID NO: 1: I64C, R71D, Y72H, A152S, F448L.

SEQ ID NO: 94 shows the amino acid sequence of a variant hydantoinase carrying the following substitutions as compared with SEQ ID NO: 1: I64C, R71D, Y72H, A152S, M417V.

SEQ ID NO: 95 shows the amino acid sequence of a variant hydantoinase carrying the following substitutions as compared with SEQ ID NO: 1: S14G, I64C, R71D, Y72H, A152S.

SEQ ID NO: 96 shows the amino acid sequence of a variant hydantoinase carrying the following substitutions as compared with SEQ ID NO: 1: S37R, I64C, R71D, Y72H, A152S.

SEQ ID NO: 97 shows the amino acid sequence of a variant hydantoinase carrying the following substitutions as compared with SEQ ID NO: 1: S14G, I64C, R71D, Y72H, A152S, E358K.

SEQ ID NO: 98 shows the amino acid sequence of a variant hydantoinase carrying the following substitutions as compared with SEQ ID NO: 1: S37R, I64C, R71D, Y72H, A152S, V318A.

SEQ ID NO: 99 shows the amino acid sequence of a variant hydantoinase carrying the following substitutions as compared with SEQ ID NO: 1: S37R, I64C, R71D, Y72H, A152S, N303S, Q404R.

SEQ ID NO: 100 shows the amino acid sequence of a variant hydantoinase carrying the following substitutions as compared with SEQ ID NO: 1: S14G, I64C, R71D, Y72H, A152S, N70D.

SEQ ID NO: 101 shows the amino acid sequence of a variant hydantoinase carrying the following substitutions as compared with SEQ ID NO: 1: S14G, I64C, R71D, Y72H, A152S, V154A.

SEQ ID NO: 102 shows the amino acid sequence of a variant hydantoinase carrying the following substitutions as compared with SEQ ID NO: 1: S37G, I64C, R71D, Y72H, A152S.

SEQ ID NO: 103 shows the amino acid sequence of a variant hydantoinase carrying the following substitutions as compared with SEQ ID NO: 1: S14A, S37G, I64C, R71D, Y72H, A152S.

SEQ ID NO: 104 shows the amino acid sequence of a variant hydantoinase carrying the following substitutions as compared with SEQ ID NO: 1: S14V, I64C, R71D, Y72H, A152S.

SEQ ID NO: 105 shows the amino acid sequence of a variant hydantoinase carrying the following substitutions as compared with SEQ ID NO: 1: S14G, S37G, I64C, R71D, Y72H, A152S.

SEQ ID NO: 106 shows the amino acid sequence of a variant hydantoinase carrying the following substitutions as compared with SEQ ID NO: 1: S14A, S37W, I64C, R71D, Y72H, A152S.

SEQ ID NO: 107 shows the amino acid sequence of a variant hydantoinase carrying the following substitutions as compared with SEQ ID NO: 1: S14A, S37V, I64C, R71D, Y72H, A152S.

SEQ ID NO: 108 shows the amino acid sequence of a variant hydantoinase carrying the following substitutions as compared with SEQ ID NO: 1: D15N, I64C, R71D, Y72H, A152S.

SEQ ID NO: 109 shows the amino acid sequence of a variant hydantoinase carrying the following substitutions as compared with SEQ ID NO: 1: S14V. S37R, I64C, R71D, Y72H, A152S.

SEQ ID NO: 110 shows the amino acid sequence of a variant hydantoinase carrying the following substitutions as compared with SEQ ID NO: 1: D15N, I64C, R71D, Y72H, A152S, V154C.

SEQ ID NO: 111 shows the amino acid sequence of a variant hydantoinase carrying the following substitutions as compared with SEQ ID NO: 1: D15N, I64C, R71D, Y72H, A152S, V154I.

SEQ ID NO: 112 shows the amino acid sequence of a variant hydantoinase carrying the following substitutions as compared with SEQ ID NO: 1: S14P, D15G, S37G, I64C, R71D, Y72H, A152S.

SEQ ID NO: 113 shows the amino acid sequence of a variant hydantoinase carrying the following substitutions as compared with SEQ ID NO: 1: S14G, D15R, S37G, I64C, R71D, Y72H, A152S.

SEQ ID NO: 114 shows the amino acid sequence of a variant hydantoinase carrying the following substitutions as compared with SEQ ID NO: 1: S14G, D15Q, S37G, I64C, R71D, Y72H, A152S.

SEQ ID NO: 115 shows the amino acid sequence of a variant hydantoinase carrying the following substitutions as compared with SEQ ID NO: 1: S14F, D15A, S37G, I64C, R71D, Y72H, A152S.

SEQ ID NO: 116 shows the amino acid sequence of a variant hydantoinase carrying the following substitutions as compared with SEQ ID NO: 1: D15S, S37G, I64C, R71D, Y72H, A152S.

SEQ ID NO: 117 shows the amino acid sequence of a variant hydantoinase carrying the following substitutions as compared with SEQ ID NO: 1: S14P, D15G, S37G, R71D, Y72H, A152S.

SEQ ID NO: 118 shows the amino acid sequence of a variant hydantoinase carrying the following substitutions as compared with SEQ ID NO: 1: S14P, D15G, S37G, I64C, R71D, Y72H.

SEQ ID NO: 119 shows the amino acid sequence of a variant hydantoinase carrying the following substitutions as compared with SEQ ID NO: 1: D15S, S37G, I64C, R71D, Y72H.

DETAILED DESCRIPTION OF THE PRESENT INVENTION

As described above, the present invention provides new hydantoinases derived from wild-type hydantoinase having amino acid sequence SEQ ID NO: 1 from *Arthrobacter* sp. with increased catalytic activity and optionally increased enantioselectivity for D-5-substituted hydantoin substrates, in particular for D-tryptophan hydantoin.

Hydantoinases according to the present invention have an amino acid sequence selected from (i) or (ii), with
  (i) amino acid sequence selected from SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18. SEQ ID NO: 19, SEQ ID NO: 20, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, or SEQ ID NO: 119,
  (ii) amino acid sequence wherein in the amino acid sequence of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, or SEQ ID NO: 119, 1 to q amino acid residues have been substituted, deleted, inserted and/or added,
  and wherein $\varphi$ is defined as $\varphi=75$,
  and wherein further the catalytic activity of the hydantoinase is higher by a factor of at least $\zeta$ than the catalytic activity of the hydantoinase having amino acid sequence SEQ ID NO: 1,
  and wherein $\zeta$ is defined as $\zeta=1.2$.

In the context of the present invention, and if not defined otherwise, the catalytic activity of a hydantoinase is defined as the catalytic activity of this enzyme with respect to the transformation of 5-substituted D-hydantoin compounds to the corresponding D-carbamoylamino acids.

In the context of the present invention the enantioselectivity of a hydantoinase is defined as the ratio $D_{act}/L_{act}$, with $D_{act}$=the catalytic activity of this enzyme for the transformation of 5-substituted D-hydantoin compounds to the corresponding D-carbamoylamino acids, and $L_{act}$=the catalytic activity of this enzyme for the transformation of the enantiomers of the 5-substituted D-hydantoin compounds to the enantiomers of the corresponding D-carbamoylamino acids, in other words $L_{act}$=the catalytic activity of this enzyme for the transformation of the corresponding 5-substituted L-hydantoin compounds to the corresponding L-carbamoylamino acids.

In preferred embodiments of the present invention $\varphi$ is selected from 70, 60, 50, 40, 30, 20, 10, 9, 8, 7, 6, 5, 4, 3, 2 or 1.

In further preferred embodiments of the present invention $\zeta$ is selected from 1.5, 2, 3, 4, 5, 10, 15, 20, 25 or 30.

In further preferred embodiments of the present invention $\varphi$ and $\zeta$ are selected as follows:

$\varphi=70$ and $\zeta=1.5$, $\varphi=70$ and $\zeta=2$, $\varphi=70$ and $\zeta=3$, $\varphi=70$ and $\zeta=4$, $\varphi=70$ and $\zeta=5$, $\varphi=70$ and $\zeta=10$, $\varphi=70$ and $\zeta=15$, $\varphi=70$ and $\zeta=20$, $\varphi=70$ and $\zeta=25$, $\varphi=70$ and $\zeta=30$, $\varphi=60$ and $\zeta=1.5$, $\varphi=60$ and $\zeta=2$, $\varphi=60$ and $\zeta=3$, $\varphi=60$ and $\zeta=4$, $\varphi=60$ and $\zeta=5$, $\varphi=60$ and $\zeta=10$, $\varphi=60$ and $\zeta=15$, $\varphi=60$ and $\zeta=20$, $\varphi=60$ and $\zeta=25$, $\varphi=60$ and $\zeta=30$, $\varphi=50$ and $\zeta=1.5$, $\varphi=50$ and $\zeta=2$, $\varphi=50$ and 1=3, $\varphi=50$ and $\zeta=4$, $\varphi=50$ and $\zeta=5$, $\varphi=50$ and $\zeta=10$, $\varphi=50$ and $\zeta=15$, $\varphi=50$ and $\zeta=20$, $\varphi=50$ and $\zeta=25$, $\varphi=50$ and $\zeta=30$, $\varphi=40$ and $\zeta=1.5$, $\varphi=40$ and $\zeta=2$, $\varphi=40$ and $\zeta=3$, $\varphi=40$ and $\zeta=4$, $\varphi=40$ and $\zeta=5$, $\varphi=40$ and $\zeta=10$, $\varphi=40$ and $\zeta=15$, $\varphi=40$ and $\zeta=20$, $\varphi=40$ and $\zeta=25$, $\varphi=40$ and $\zeta=30$, $\varphi=30$ and $\zeta=1.5$, $\varphi=30$ and $\zeta=2$, $\varphi=30$ and $\zeta=3$, $\varphi=30$ and $\zeta=4$, $\varphi=30$ and $\zeta=5$, $\varphi=30$ and $\zeta=10$, $\varphi=30$ and $\zeta=15$, $\varphi=30$ and $\zeta=20$, $\varphi=30$ and $\zeta=25$, $\varphi=30$ and $\zeta=30$, $\varphi=20$ and $\zeta=1.5$, $\varphi=20$ and $\zeta=2$, $\varphi=20$ and $\zeta=3$, $\varphi=20$ and $\zeta=4$, $\varphi=20$ and $\zeta=5$, $\varphi=20$ and $\zeta=10$, $\varphi=20$ and $\zeta=15$, $\varphi=20$ and $\zeta=20$, $\varphi=20$ and $\zeta=25$, $\varphi=20$ and $\zeta=30$, φ=10 and ζ=1.5, φ=10 and ζ=2, φ=10 and ζ=3, φ=10 and ζ=4, φ=10 and ζ=5, φ=10 and ζ=10, φ=10 and ζ=15, φ=10 and ζ=20, φ=10 and ζ=25, φ=10 and ζ=30,
φ=9 and ζ=1.5, φ=9 and ζ=2, φ=9 and ζ=3, φ=9 and ζ=4, φ=9 and ζ=5, φ=9 and ζ=10, φ=9 and ζ=15, φ=9 and ζ=20, φ=9 and ζ=25, φ=9 and ζ=30,
φ=8 and ζ=1.5, φ=8 and ζ=2, φ=8 and ζ=3, φ=8 and ζ=4, φ=8 and ζ=5, φ=8 and ζ=1.50, φ=8 and ζ=15, φ=8 and ζ=20, φ=8 and ζ=25, φ=8 and ζ=30,
φ=7 and ζ=1.5, φ=7 and ζφ=2, φ=7 and ζ=3, φ=7 and ζ=4, φ=7 and ζ=5, φ=7 and ζ=10, φ=7 and ζ=15, φ=7 and ζ=20, φ=7 and ζ=25, φ=7 and ζ=30,
φ=6 and ζ=1.5, φ=6 and ζ=2, φ=6 and ζ=3, φ=6 and ζ=4, φ=6 and ζ=5, φ=6 and ζ=10, φ=6 and ζ=15, φ=6 and ζ=20, φ=6 and ζ=25, φ=6 and ζ=30,
φ=5 and ζ=1.5, φ=5 and ζ=2, φ=5 and ζ=3, φ=5 and ζ=4, φ=5 and ζ=5, φ=5 and ζ=10, φ=5 and ζ=15, φ=5 and ζ=20, φ=5 and ζ=25, φ=5 and ζ=30,
φ=4 and ζ=1.5, φ=4 and ζ=2, φ=4 and ζ=3, φ=4 and ζ=4, φ=4 and ζ=5, φ=4 and ζ=10, φ=4 and ζ=15, φ=4 and ζ=20, φ=4 and ζ=25, φ=4 and ζ=30,
φ=3 and ζ=1.5, φ=3 and ζ=2, φ=3 and ζ=3, φ=3 and ζ=4, φ=3 and ζ=5, φ=3 and ζ=10, φ=3 and ζ=15, φ=3 and ζ=20, φ=3 and ζ=25, φ=3 and ζ=30,
φ=2 and ζ=1.5, φ=2 and ζ=2, φ=2 and ζ=3, φ=2 and ζ=4, φ=2 and ζ=5, φ=2 and ζ=10, φ=2 and ζ=15, φ=2 and ζ=20, φ=2 and ζ=25, φ=2 and ζ=30,
φ=1 and ζ=1.5, φ=1 and ζ=2, φ=1 and ζ=3, φ=1 and ζ=4, φ=1 and ζ=5, φ=1 and ζ=10, φ=1 and ζ=15, φ=1 and ζ=20, φ=1 and ζ=25, φ=1 and ζ=30.

In another embodiment of the present invention the hydantoinase of the present invention has at least 80% identity with or has an amino acid sequence comprising deletion, substitution, insertion and/or addition of a maximum of 90 amino acid residues in comparison with a hydantoinase having amino acid sequence SEQ ID NO: 5; wherein amino acid residues at positions 152, 64, 71, 72, 95, 154, 181, 284, 285, 398 and 452 are defined as X152, X64, X71, X72, X95, X154, X181, X284, X285, X398 and X452 and wherein these amino acid residues are selected as follows:

X152=any amino acid residue other than alanine;
X64=any amino acid residue;
X71=any amino acid residue;
X72=any amino acid residue;
X95=any amino acid residue;
X154=any amino acid residue;
X181=any amino acid residue;
X284=any amino acid residue;
X285=any amino acid residue;
X398=any amino acid residue;
X452=any amino acid residue;

and wherein further the catalytic activity of the hydantoinase is higher by a factor of at least 1.2 than the catalytic activity of the hydantoinase having amino acid sequence SEQ ID NO: 1.

In a preferred embodiment the catalytic activity is higher by a factor of at least 1.5, 2, 3, 4, 5, 10, 15, 20, 25 or 30 than the catalytic activity of the hydantoinase having amino acid sequence SEQ ID NO: 1.

In another preferred embodiment the enantioselectivity for D-hydantoin is higher by a factor of at least 1.2, 1.5, 2, 3, 4, 5, 10, 15, 20, 25, 30, 50, 100 or 150 than the enantioselectivity of the hydantoinase having amino acid sequence SEQ ID NO: 1. In an even more preferred embodiment the enantioselectivity of the hydantoinase for D-5-indolylmethylhydantoin (D-tryptophan hydantoin) has been increased by at least factor of 1.2, preferably at least a factor of 1.5, 2, 3, 4, 5, 10, 15, 20, 25, 30, 50, 100 or 150, compared to the hydantoinase having the amino acid sequence shown in SEQ ID NO: 1.

The person skilled in the art understands that variants of the hydantoinase as described herein are also included in the scope of the present invention. These variant hydantoinases have at least 80% identity with or have an amino acid sequence comprising deletion, substitution, insertion and/or addition of a maximum of 90 amino acid residues in comparison with a hydantoinase having amino acid sequence SEQ ID NO: 1 and SEQ ID NO: 5, respectively. In these variants the specific amino acid substitution(s) with respect to the reference amino acid sequence (SEQ ID NO: 1 and SEQ ID NO: 5, respectively) according to the present invention is/are maintained.

In addition, derivatives of the above mentioned proteins having hydantoinase activity are provided, which derivatives have at least 80% identity, preferably at least 85% identity, further preferred at least 90% identity, still further preferred at least 95% identity, further preferred at least 96% identity, more preferred at least 97% identity, still further preferred at least 98% identity and most preferred at least 99% identity to SEQ ID NO: 5, 6, 7, 8, 9, 10, 11, 12, 13, 14, 15, 16, 17, 18, 19 or 20, respectively. As outlined above, in these variants the amino acid substitution(s) according to the present invention with respect to the reference sequence (SEQ ID NO: 1 and SEQ ID NO: 5, respectively) are maintained.

In addition, derivatives of the above mentioned proteins having hydantoinase activity are provided, which derivatives being represented by a protein having an amino acid sequence comprising deletion, substitution, insertion and/or addition of a maximum of 90 amino acid residues with respect to the amino acid sequence shown in SEQ ID NO: 5, 6, 7, 8, 9, 10, 11, 12, 13, 14, 15, 16, 17, 18, 19 or 20. As outlined above, in these variants the amino acid substitution(s) according to the present invention with respect to the reference sequence (SEQ ID NO: 1 and SEQ ID NO: 5, respectively) are maintained.

The present invention also refers to variant hydantoinases having an amino acid sequence comprising deletion, substitution, insertion and/or addition of a maximum of 90 amino acid residues. The scope "a maximum of 90 amino acid residues" in the phrase "comprising deletion, substitution, insertion and/or addition of a maximum of 90 amino acid residues" used herein may be limited to a maximum of 70, preferred a maximum of 45, further preferred a maximum of 40, more preferred a maximum of 35, further preferred a maximum of 30, still further preferred a maximum of 25, even further preferred a maximum of 20, more preferred a maximum of 15, still further preferred a maximum of 10 and most preferred a maximum of 5 amino acid residues. The term of "a maximum of 90 amino acid residues" in the phrase "comprising deletion, substitution, insertion and/or addition of a maximum of 90 amino acid residues" used herein means preferably 1 to 70, preferred 1 to 45, further preferred 1 to 40, more preferred 1 to 35, further preferred 1 to 30, still further preferred 1 to 25, even further preferred 1 to 20, more preferred 1 to 15, still further preferred 1 to 10 and most preferred 1 to 5 amino acid residues. The term "addition" means N-terminal or C-terminal addition of amino acid residues in respect of above mentioned sequences.

In addition, fragments of the above mentioned proteins having amino acid sequence SEQ ID NO: 5, 6, 7, 8, 9, 10, 11, 12, 13, 14, 15, 16, 17, 18, 19 or 20, respectively, having hydantoinase activity are provided, wherein preferably the fragment contains at least 300, further preferred at least 350 and particularly preferred at least 400 and most preferred at least 450 consecutive amino acids of the amino acid sequence SEQ ID NO: 5, 6, 7, 8, 9, 10, 11, 12, 13, 14, 15, 16, 17, 18, 19 or 20, respectively, or their derivatives as defined above.

In another embodiment of the present invention X152, X64, X71, X72, X95, X154, X181, X284, X285, X398, X452 are further limited as follows:
X152=Cys, Gly, Ser, Thr or Val;
X64=Ile, Thr or Val;
X71=Arg, Gin, Asp, Glu, Val, Ser, Tyr or Leu;
X72=Tyr, His or Asn;
X95=Ile or His;
X154=Val, Ala, Cys, Gly, Ile, Asn or Ser;
X181=Val or Ala;
X284=Val or Phe;
X285=Ala or Asp;
X398=Thr or Ala;
X452=His or Leu.

In another embodiment of the present invention X152, X64. X71, X72, X95, X154, X181, X284, X285, X398, X452 are further limited as follows:
X152=Cys, Ser or Val;
X64=Ile, Thr or Val
X71=Arg, Gin, Asp, Glu, Val, Ser, Tyr or Leu
X72=Tyr, His or Asn
X95=Ile or His;
X154=Cys, Ile or Ser;
X181=Val or Ala;
X284=Val or Phe;
X285=Ala or Asp;
X398=Thr or Ala;
X452=His or Leu.

In another embodiment of the present invention X152, X154 are further limited as follows:
X152=Cys, Gly, Ser, Thr or Val;
X154=Ala, Cys, Gly, Ile, Asn or Ser.

In another embodiment of the present invention X152, X154 are further limited as follows:
X152=Cys, Ser or Val;
X154=Cys, Ile or Ser.

In another embodiment of the present invention X152 is further limited as follows:
X152=Ser; X152=Cys; X152=Val; X152=Gly or X152=Thr.

In another embodiment of the present invention X152 and X154 are further limited as follows:
X152=Ser; X154=Ile.

In another embodiment of the present invention X152 and X154 are further limited as follows:
X152=Val; X154=Cys.

In another embodiment of the present invention X152 and X154 are further limited as follows:
X152=Cys; X154=Ser.

In another embodiment of the present invention X152, X71, X72, X154, X181 are further limited as follows:
X152=Ser; X71=Asp; X72=His; X154=Val; X181=Val.

In another embodiment of the present invention X152, X71, X72, X154, X181 are further limited as follows:
X152=Ser; X71=Asp; X72=Asn; X154=Val; X181=Val.

In another embodiment of the present invention X152, X71, X72, X154, X181 are further limited as follows:
X152=Ser; X71=Val; X72=Asn; X154=Val; X181=Val.

In another embodiment of the present invention X152, X71, X72, X154, X181 are further limited as follows:
X152=Cys; X71=Ser; X72=Asn; X154=Ser; X181=Ala.

In another embodiment of the present invention X152, X71, X72, X154, X181 are further limited as follows:
X152=Ser; X71=Tyr; X72=Asn; X154=Val; X181=Val.

In another embodiment of the present invention X152, X71, X72, X154, X181 are further limited as follows:
X152=Cys; X71=Leu; X72=Tyr; X154=Ser; X181=Val.

In another embodiment of the present invention X152, X71, X72, X154, X181 are further limited as follows:
X152=Ser; X71=Tyr; X72=His; X154=Val; X181=Val.

In another embodiment of the present invention a hydantoinase is provided wherein X152, X64, X71, X72, X95, X154, X181, X284, X285, X398, X452 are further limited as follows:
X152=Ser; X64=Ile; X71=Arg; X72=Tyr; X95=Ile; X154=Val; X181=Val; X284=Val; X285=Ala; X398=Thr; X452=His.

In another embodiment of the present invention X152, X64, X71, X72, X95, X154, X181, X284, X285, X398, X452 are further limited as follows:
X152=Cys; X64=Ile; X71=Arg; X72=Tyr; X95=Ile; X154=Val; X181=Val; X284=Val; X285=Ala; X398=Thr; X452=His.

In another embodiment of the present invention X152, X64, X71, X72, X95, X154, X181, X284, X285, X398, X452 are further limited as follows:
X152=Val; X64=Ile; X71=Arg; X72=Tyr; X95=Ile; X154=Val; X181=Val; X284=Val; X285=Ala; X398=Thr; X452=His.

In another embodiment of the present invention X152, X64, X71, X72, X95, X154, X181, X284, X285, X398, X452 are further limited as follows.
X152=Gly; X64=Ile; X71=Arg; X72=Tyr; X95=Ile; X154=Val; X181=Val; X284=Val; X285=Ala; X398=Thr; X452=His.

In another embodiment of the present invention X152, X64, X71, X72, X95, X154, X181, X284, X285, X398, X452 are further limited as follows:
X152=Thr; X64=Ile; X71=Arg; X72=Tyr; X95=Ile; X154=Val; X181=Val; X284=Val; X285=Ala; X398=Thr; X452=His;

In another embodiment of the present invention X152, X64, X71, X72, X95, X154, X181, X284, X285, X398, X452 are further limited as follows:
X152=Ser; X64=Ile; X71=Arg; X72=Tyr; X95=Ile; X154=Ile; X181=Val; X284=Val; X285=Ala; X398=Thr; X452=His.

In another embodiment of the present invention X152, X64, X71, X72, X95, X154, X181, X284, X285. X398, X452 are further limited as follows:
X152=Val; X64=Ile; X71=Arg; X72=Tyr; X95=Ile; X154=Cys; X181=Val; X284=Val; X285=Ala; X398=Thr; X452=His.

In another embodiment of the present invention X152, X64, X71, X72, X95, X154, X181, X284, X285, X398, X452 are further limited as follows:
X152=Cys; X64=Ile; X71=Arg; X72=Tyr; X95=Ile; X154=Ser; X181=Val; X284=Val; X285=Ala; X398=Thr; X452=His.

In another embodiment of the present invention X152, X64, X71, X72, X95, X154, X181, X284, X285, X398, X452 are further limited as follows:
X152=Ser; X64=Ile; X71=Asp; X72=His; X95=Ile; X154=Val; X181=Val; X284=Val; X285=Ala; X398=Thr; X452=His.

In another embodiment of the present invention X152, X64, X71, X72, X95, X154, X181, X284, X285, X398, X452 are further limited as follows:
   X152=Ser; X64=Ile; X71=Asp; X72=Asn; X95=Ile; X154=Val; X181=Val; X284=Val; X285=Ala; X398=Thr; X452=His.

In another embodiment of the present invention X152, X64, X71, X72, X95, X154, X181, X284, X285, X398, X452 are further limited as follows;
   X152=Ser; X64=Ile; X71=Val; X72=Asn; X95=Ile; X154=Val; X181=Val; X284=Val; X285=Ala; X398=Thr; X452=His.

In another embodiment of the present invention X152, X64. X71, X72. X95, X154, X181, X284, X285, X398, X452 are further limited as follows:
   X152=Cys; X64=Ile; X71=Ser; X72=Asn; X95=Ile; X154=Ser; X181=Ala; X284=Val; X285=Ala; X398=Thr; X452=His.

In another embodiment of the present invention X152, X64, X71, X72, X95, X154, X181, X284, X285, X398, X452 are further limited as follows:
   X152=Ser; X64=Ile; X71=Tyr; X72=Asn; X95=Ile; X154=Val; X181=Val; X284=Val; X285=Ala; X398=Thr; X452=His.

In another embodiment of the present invention X152, X64, X71, X72, X95, X154, X181, X284, X285, X398, X452 are further limited as follows:
   X152=Cys; X64=Ile; X71=Leu; X72=Tyr; X95=Ile; X154=Ser; X181=Val; X284=Val; X285=Ala; X398=Thr; X452=His.

In another embodiment of the present invention X152, X64, X71, X72, X95, X154, X181, X284, X285, X398, X452 are further limited as follows:
   X152=Ser; X64=Ile; X71=Tyr; X72=His; X95=Ile; X154=Val; X181=Val; X284=Val; X285=Ala; X398=Thr; X452=His.

In another embodiment of the present invention a hydantoinase according to the invention transforms at least one of the following substrates hydantoin, 5-methylhydantoin, 5-benzylhydantoin, 5-(4-hydroxybenzyl)hydantoin, 5-indolylmethylhydantoin, 5-(3,4-dihydroxybenzyl)hydantoin, 5-methylthioethylhydantoin, 5-isopropylhydantoin, 5-isobutylhydantoin, 5-sec-butylhydantoin, 5-(4-aminobutyl)hydantoin, 5-hydroxymethylhydantoin, or a 5-substituted hydantoin compound corresponding to a non-natural amino acid, respectively a derivative thereof, to the respective carbamoyl amino acid, wherein the catalytic activity of the hydantoinase in respect of the transformation of said substrate is at least as high as the catalytic activity of the hydantoinase having amino acid sequence SEQ ID NO: 1 in respect of the transformation of D-5-indolylmethylhydantoin.

As mentioned above, substrates for the hydantoinase according to the invention may be any D-5-substituted hydantoin compounds capable of being hydrolyzed at the substrate specificity of this enzyme. Those include also 5-substituted hydantoin compounds corresponding to non-natural amino acid or a derivative thereof. A non-natural amino acid or a derivative thereof refers to an amino acid which is not encoded by standard genetic code. Respective hydantoins of non-natural amino acids or derivatives thereof include 5-phenylhydantoin, 5-(4-hydroxyphenyl)hydantoin, 5-methoxymethylhydantoin, 5-benzyloxymethylhydantoin, 5-(3,4-methylenedioxybenzyl) hydantoin, dihydrouracil. Preferably, the substrate of the hydantoinase according to the present invention is D,L-5-indolylmethylhydantoin, more preferred D-5-indolylmethylhydantoin.

The present invention also provides polynucleotides encoding hydantoinases of the invention.

Accordingly, the present invention provides an isolated or recombinant polynucleotide hybridizing under stringent conditions comprising a wash in a solution of 1× sodium chloride/sodium citrate (SSC) and 0.1% sodium dodecyl sulfate (SDS) at 65° C. to the full-length complement of the polynucleotide having a nucleotide sequence according to the present invention as defined above; wherein the catalytic activity of the hydantoinase is higher by a factor of at least $\zeta$ than the catalytic activity of the hydantoinase having amino acid sequence SEQ ID NO: 1,
and wherein $\zeta$ is defined as $\zeta=1.2$.

The present invention also provides a vector comprising the polynucleotide as described above encoding the hydantoinase according to the present invention. Preferably, the vector further comprises regulatory sequences operatively linked with and suitable for expression of the polynucleotide in a host cell.

The present invention further provides an isolated or transformed host cell comprising the polynucleotide or the vector comprising the polynucleotide as described above encoding the hydantoinase according to the present invention. Preferably, the host is selected from the group consisting of *Escherichia coli*, coryneform bacteria, *Bacillus* sp. The host cell expresses the hydantoinase according to the present invention. In a preferred embodiment the host cell expresses at least the enzymatic activities selected from the following: hydantoinase; hydantoinase and hydantoin racemase; hydantoinase and carbamoylase; or hydantoinase and hydantoin racemase and carbamoylase.

In addition, the present invention provides a process for preparing amino acids comprising the steps of
(a) providing hydantoinase activity of a hydantoinase according to the present invention and carbamoylase activity and at least one 5-substituted hydantoin to a reaction medium, and optionally providing hydantoin racemase activity to said reaction medium;
(b) incubating the reaction medium in order to allow transformation of the 5-substituted hydantoin to the respective amino acids by the enzymatic activities provided in (a); and
(c) recovering the amino acids obtained from the enzymatic transformation of the respective 5-substituted hydantoin from the reaction medium.

In a preferred process said 5-substituted hydantoin is selected from D,L-5-substituted hydantoin, D,L-5-indolylmethylhydantoin (=D,L-tryptophan hydantoin), D-5-substituted hydantoin, D-5-indolylmethylhydantoin (=D-tryptophan hydantoin).

In a still further preferred process said 5-substituted hydantoin provided to the reaction medium is L-5-substituted hydantoin or D,L-5-substituted hydantoin, and in addition hydantoin racemase activity is provided to the reaction medium in step (a) for transforming L-5-substituted hydantoin or D,L-5-substituted hydantoin to D-5-substituted hydantoin.

In yet another preferred process the amino acid to be prepared is D-tryptophan and the 5-substituted hydantoin is selected from D-5-indolylmethylhydantoin, L-5-indolylmethylhydantoin or D,L-5-indolylmethylhydantoin.

In the process the 5-substituted hydantoin is transformed by the hydantoinase of the present invention into the respective carbamoylamino acid which is transformed into the respective amino acid by said carbamoylase activity. In a particularly preferred embodiment said carbamoylamino acid is selected from N-(aminocarbonyl)-DL-tryptophan (=N-carbamoyl-DL-tryptophan; =CA Index Name: N-(aminocarbonyl)-tryptophan; =Registry Number: 98299-50-4; Formula: C12 H13 N3 O3) or N-carbamoyl-L-tryptophan (=CA Index Name: N-(aminocarbonyl)-L-tryptophan=Registry Number: 89595-64-2; Formula: C12 H13 N3 O3).

In yet another preferred process the reaction medium is a medium that partially or entirely consists of cell culture medium and the hydantoinase activity is provided by a host cell according to the present invention, and the host cell is cultivated in said cell reaction medium.

In a particularly preferred process the reaction medium is a medium that partially or entirely consists of cell culture medium and the carbamoylase activity is provided by the host cell according to the present invention or by a second host cell, and said host cell(s) is/are cultivated in said reaction medium.

In a preferred embodiment the host cell(s) expressing hydantoinase activity and carbamoylase activity and optionally hydantoin racemase activity, either in separate cells or in the same cell, are cultivated in a cell culture medium in order to create a biomass, then cell culture medium and biomass are separated and the biomass is resuspended by using buffer or water. The substrate is either added to said buffer or water before, during or after the addition of the biomass in order to start the transformation of the substrate.

The hydantoinases of the present invention may be used as described, for example in Biocatalytic Production of Amino Acids and Derivatives (Rozzell, J. D. and Wagner. F. eds., Hanser Publisher, NY, at pages 75-176 (1992)) for the use in the production of optically pure amino acids from D,L-5-monosubstituted hydantoins. The general use of hydantoinases is also described in "Enzyme catalysis in organic synthesis" (Dranz, K. and Waldmann, H. eds., VCH-Verlag, Weinheim, at pages 409-431 (1995)) and Wagner, T. et al. (Production of 1-methionine from D,L-5-(2-methylthioethyl) hydantoin by resting cells of a new mutant strain of *Arthrobacter* species DSM 7330, Journal of Biotechnology 46: 63-68 (1996)).

For the enzymatic transformation of D,L- or L-5-substituted hydantoins or D,L- or L-carbamoylamino acids into the respective D-amino acid it is preferred to apply whole-cell catalyst technology which includes expression of the hydantoinase of the present invention and expression of carbamoylase, and further preferred also expression of hydantoin racemase.

The hydantoinase according to the present invention can be used within this process also in their free or immobilized form. Also the carbamoylase and hydantoin racemase may be immobilized, too. Techniques to immobilize enzymes are well known to the skilled person. Preferred methods are mentioned in Bhavender P. Sharma, Lorraine F. Bailey and Ralph A. Messing (Immobilisierte Biomaterialien Techniken und Anwendungen, Angew. Chem., 94, pp. 836-852 (1992)); Dordick et al. (J. Am. Chem. Soc., 116, pp. 5009-5010 (1994)), Okahata et al., Tetrahedron Lett., 38, pp. 1971-1974 (1997)), Adlercreutz et al. (Biocatalysis, 6, 291-305 (1992)); Goto et al. (Biotechnol. Prog. 10, pp. 263-268 (1994)), Kamiya et al. (Biotechnol. Prog., 11, pp. 270-275 (1995)), Okahata et al. (Tibtech, February 1997, 15, pp. 50-54); Fishman at al. (Biotechnol. Lett., 20, pp. 535-538 (1998)).

The transformation of 5-substituted hydantoins or carbamoylamino acids into the respective amino acid can be conducted in a batch process or continuous manner. Advantageously, an enzyme-membrane-reactor is used as the reaction vessel (Wandrey et al. in Jahrbuch 1998, Verfahrenstechnik und Chemieingenieurwesen, VDI S. 151ff.; Wandrey et al. in Applied Homogeneous Catalysis with Organometallic Compounds, Vol. 2, VCH 1996, pp. 832 ff.; Kragl et al., Angew. Chem., 6, pp. 684f. (1996)).

In respect of the production of amino acids using whole cell catalyst approach advantageously, bacterial cells are used because of high reproduction rates and easy growing conditions to be applied. There are several bacteria known to the skilled person which can be utilized in this respect. Preferably *E. coli* can be used as the cell and expression system in this regard (Yanisch-Perron et al., Gene, 33, 103-109 (1985)).

For producing amino acids cells expressing the hydantoinase of the present invention, and preferably in addition expressing carbamoylase and further preferred in addition expressing hydantoin racemase, may be used in culture medium. Alternatively, respective isolated cells, washed cells, cell treatment products, crude enzyme solution or purified enzyme solution obtained from the cell treatment product, may be used in a reaction mixture. For carrying out the reaction said culture medium or reaction mixture, respectively, containing 5-substituted hydantoin compound as substrate is kept at a temperature from 15 to 45° C., preferably from 25 to 40° C., at pH 5 to 9, preferably at pH 6 to 8, while allowing to stand or stir for 8 hours to 5 days. Said culture medium or reaction mixture, respectively, may further contain transition metal ions, preferably selected from $Zn^{2+}$, $Mn^{2+}$ and $Co^{2+}$, at a concentration from 0.02 mM to 10 mM, preferably from 0.1 mM to 5 mM. When using intact cells the reaction mixture may further contain nutrient components essential for the growth of the transformed cell such as carbon sources, nitrogen sources and inorganic ions. Further, the substrate (5-substituted hydantoin or carbamoylamino acid compound) may be added to the culture medium or to the reaction mixture in portions.

As the enzymes employed in the described method are also capable to catalyse the respective reverse reaction, the present invention in addition also provides a process for preparing D-amino acids as described above wherein instead of said 5-substituted hydantoin as substrate N-carbamoyl-D,L-amino acid or N-carbamoyl-L-amino acid is used:

said N-carbamoyl-D,L-amino acid or N-carbamoyl-L-amino acid is transformed by the hydantoinase according to the present invention into the respective D,L-5-substituted hydantoin or L-5-substituted hydantoin compound. Further, said D,L-5-substituted hydantoin or L-5-substituted hydantoin compound is transformed by hydantoin racemase into the D-enantiomer, namely the respective D-5-substituted hydantoin compound. Then the D-5-substituted hydantoin compound is transformed by the hydantoinase according to the present invention into the respective N-carbamoyl-D-amino acid. Subsequently, the carbamoylase transforms the N-carbamoyl-D-amino acid into the respective D-amino acid. In a particularly preferred embodiment of this process the N-carbamoylamino acid used as substrate is N-(aminocarbonyl)-DL-tryptophan (=N-carbamoyl-DL-tryptophan; =CA Index Name: N-(aminocarbonyl)-tryptophan; =Registry Number: 98299-50-4; Formula: C12 H13 N3 O3) or N-carbamoyl-L-tryptophan (=CA Index Name: N-(aminocarbonyl)-L-tryptophan=Registry Number: 89595-64-2; Formula: C12 H13 N3 O3).

The amino acid produced in a culture medium or a reaction mixture can rapidly be quantified by a known method. For this, high pressure liquid chromatography (HPLC) may be used employing a C-18 column and for example a mixture of 20 mM potassium phosphate (pH 2.3) containing 1% acetonitrile and acetonitrile containing 10% $H_2O$ as eluent.

Amino acids accumulated in culture medium or reaction mixture can be collected from the culture medium or reaction mixture by standard methods. For example, procedures such as filtration, centrifugation, concentration under vacuum, ion exchange or adsorption chromatography, crystallization and the like, may be employed, if necessary in combination with each other.

The following reaction scheme shows the reaction steps and enzymes involved in the catalytic transformation (exemplified by the transformation of D-hydantoin). D-hydantoin is transformed to N-carbamoyl-D-amino acid by the catalytic activity of D-hydantoinase, which is catalyzing the reaction of hydrolyzing a D-5-substituted hydantoin compound to give an N-carbamoyl-D-amino acid. In a further reaction step an enzyme referred to as N-carbamoylamino acid hydrolase catalyzes the reaction of hydrolyzing said N-carbamoyl-D-amino acid to give an optically active D-amino acid. Further, an enzyme referred to as hydantoin racemase catalyzes the transformation of the optically active L-hydantoin compound to the optically active D-hydantoin compound and vice versa.

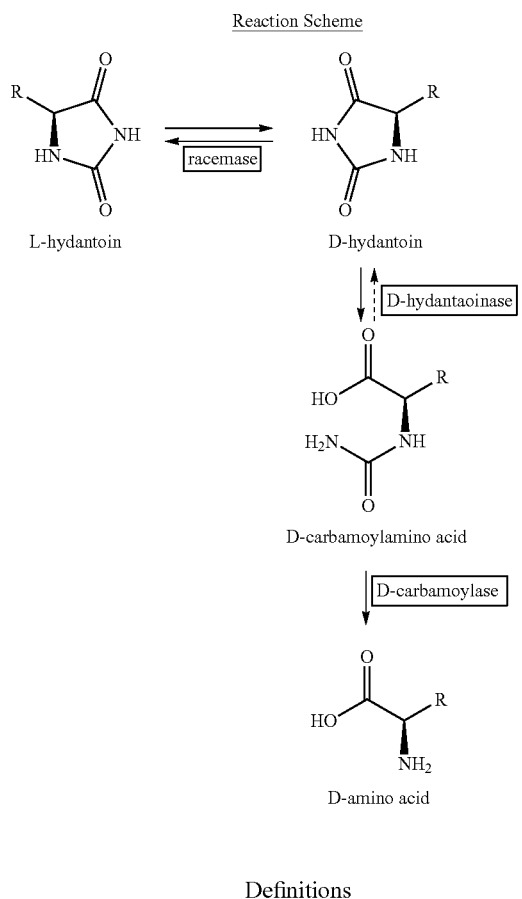

Reaction Scheme

Definitions

Hydantoinase: The term "hydantoinase" or "hydantoinase activity" is defined herein as the enzyme or the activity of an enzyme hydrolyzing hydantoin, in particular 5-substituted hydantoin. Hydantoinases catalyze the reaction of hydrolyzing 5-substituted hydantoin to form the respective N-carbamoylamino acid. In particular, the hydantoinases according to the present invention catalyze the reaction of hydrolyzing D-5-indolylmethylhydantoin to form N-carbamoyl-D-tryptophan, or the reaction of hydrolyzing L-5-indolylmethylhydantoin to form N-carbamoyl-L-tryptophan. An example for a hydantoinase is a protein having amino acid sequence SEQ ID NO: 1. An example for a hydantoinase activity is the catalytic activity of a protein having amino acid sequence SEQ ID NO: 1 towards a compound such as L-5-methylthioethylhydantoin, L-5-(4-hydroxybenzyl)hydantoin or L-5-benzylhydantoin, which is transformed to the respective N-carbamoylamino acid by the activity of said hydantoinase.

Hydantoin racemase: The term "hydantoin racemase" or "hydantoin racemase activity" is defined herein as the enzyme or the activity of an enzyme transforming L-hydantoin to D-hydantoin and vice versa. In particular, N-hydantoin racemase catalyzes the reaction of transforming L-5-indolylmethylhydantoin to form D-5-indolylmethylhydantoin, or catalyzes the reaction of transforming D-5-indolylmethylhydantoin to form L-5-indolylmethylhydantoin. An example for a hydantoin racemase is a protein having amino acid sequence SEQ ID NO: 3. An example for a hydantoin racemase activity is the catalytic activity of a protein having amino acid sequence SEQ ID NO: 3 towards a compound such as L-5-methylthioethylhydantoin, L-5-(4-hydroxybenzyl)hydantoin, L-5-benzylhydantoin or L-5-indolylmethylhydantoin, which is transformed to the respective D-enantiomer by the activity of said hydantoin racemase.

N-carbamoylase: The term "N-carbamoylase" or "N-carbamoylase activity" is defined herein as the enzyme or the activity of an enzyme hydrolyzing N-carbamoylamino acid, in particular N-carbamoyl-D-amino acid. N-carbamoylase or N-carbamoylamino acid hydrolase, respectively, catalyzes the reaction of hydrolyzing said N-carbamoylamino acid, in particular N-carbamoyl-D-amino acid to give the respective amino acid, in particular an optically active D-amino acid. In particular, N-carbamoylases catalyze the reaction of hydrolyzing N-carbamoyl-D-tryptophan to form D-tryptophan, or catalyze the reaction of hydrolyzing N-carbamoyl-L-tryptophan to form L-tryptophan. An example for an N-carbamoylase is a protein having amino acid sequence SEQ ID NO: 4. An example for an N-carbamoylase activity is the catalytic activity of a protein having amino acid sequence SEQ ID NO: 4 towards a compound such as N-carbamoyl methionine, N-carbamoyl tyrosine, N-carbamoyl phenylalanine or N-carbamoyl tryptophan, which is transformed to the respective amino acid by the activity of said N-carbamoylase.

5-substituted hydantoin: The term "5-substituted hydantoin" refers to a compound according to formula (I) below, wherein R is represented by hydrogen, —$CH_3$, —CH($CH_3$)$_2$, —$CH_2$—CH($CH_3$)$_2$, —CH($CH_3$)—$CH_2$—$CH_3$, benzyl, 4-hydroxybenzyl, indolylmethyl, —$CH_2$—COOH, —$CH_2$—$CONH_2$, —$CH_2$—$CH_2$—COOH, —$CH_2$—$CH_2$—$CONH_2$, —$CH_2$—OH, —CH(OH)—$CH_3$, —$CH_2$—SH, —$CH_2$—$CH_2$—S—$CH_3$, imidazolylmethyl, —$CH_2$—$CH_2$—$CH_2$—NH—C(NH)$NH_2$, —$CH_2$—$CH_2$—$CH_2$—$CH_2$—$NH_2$, or the term "5-substituted hydantoin" refers to proline hydantoin. Said residues correspond to naturally occurring amino acids, which are obtained upon hydrolysis of the respective hydantoin compound by hydantoinase and subsequent hydrolysis of the respective N-carbamoylamino acid by N-carbamoylase. Further, the 5-substituted hydantoin compound may correspond to a non-natural amino acid or a derivative thereof, such as 5-phenylhydantoin, 5-(4-hydroxyphenyl)hydantoin, 5-methoxymethylhydantoin, 5-benzyloxymethylhydantoin, 5-(3,4-methylenedioxybenzyl) hydantoin, dihydrouracil. It should be noted that Formula (I) shows the D-enantiomer of a 5-substituted hydantoin.

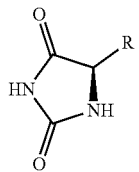

Formula (I)

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequence" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Cell culture medium: The term "cell culture medium" generally means the medium used for cultivation of microorganisms including bacteria, yeast and fungi, and may be referred to also as "fermentation medium".

Non-natural amino acid: The term "non-natural amino acid" refers to an alpha amino acid having the formula $NH_2$—$CH(R)$—$COOH$, wherein R represents a modified residue of a proteinogenic amino acid residue, which proteinogenic amino acid residue is selected from hydrogen, —$CH_3$, —$CH(CH_3)_2$, —$CH_2$—$CH(CH_3)_2$, —$CH(CH_3)$—$CH_2$—$CH_3$, benzyl, 4-hydroxybenzyl, indolylmethyl, —$CH_2$—$COOH$, —$CH_2$—$CONH_2$, —$CH_2$—$CH_2$—$COOH$, —$CH_2$—$CH_2$—$CONH_2$, —$CH_2$—$OH$, —$CH(OH)$—$CH_3$, —$CH_2$—$SH$, —$CH_2$—$CH_2$—$S$—$CH_3$, imidazolylmethyl, —$CH_2$—$CH_2$—$CH_2$—$NH$—$C(NH)NH_2$, —$CH_2$—$CH_2$—$CH_2$—$CH_2$—$NH_2$, or the term "non-natural amino acid" refers a derivative of proline, which may be modified in the —$CH_2$—$CH_2$—$CH_2$— group of its ring structure. The above mentioned modification may be substitution of hydrogen atom(s) by aliphatic group, aromatic group, heterocyclic group, acidic group, basic group, hydroxyl group and/or halogen such as F.

Modification: The term "modification" means herein any chemical modification of the polypeptide consisting of the polypeptide according to the present invention or a homologous sequence thereof; as well as genetic manipulation of the DNA encoding such a polypeptide. The modification can be substitutions, deletions, insertions and/or additions of one or more amino acids.

Variant: When used herein, the term "variant" means a polypeptide having hydantoinase activity produced by an organism expressing a modified nucleotide sequence of the polypeptide according to the present invention or a homologous sequence thereof. The modified nucleotide sequence is obtained through human intervention by modification of the nucleotide sequence. Variant polypeptide sequences may also be naturally occurring. For example, a hydantoinase isolated from *Microbacterium liquefaciens* AJ3912 has been described which has about 83% identity with the hydantoinase having amino acid sequence SEQ ID NO: 1. This *Microbacterium liquefaciens* hydantoinase may be regarded as a (naturally occurring) variant of the amino acid sequence SEQ ID NO: 1.

The proteins of the current invention can, for example, be synthesized, prepared from purified proteins, or produced using recombinant processes and techniques known in the art. Although specific techniques for their preparation are described herein, it is to be understood that all appropriate techniques suitable for production of these peptides are intended to be within the scope of this invention. Generally, these techniques include DNA and protein sequencing, cloning, expression and other recombinant engineering techniques permitting the construction of prokaryotic and eukaryotic vectors encoding and expressing each of the proteins of the invention.

The terms "peptide" and "oligopeptide" are considered synonymous (as is commonly recognized) and each term can be used interchangeably as the context requires indicating a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, 2$^{nd}$, ed. Cold Spring Harbor Laboratory, Cold Spring Harbor Laboratory Press, Cold Spring Harbor, N.Y., 1989).

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The hydantoinase according to the invention can be recovered and purified from recombinant cell cultures by well-known processes including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, fungus, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The proteins of the present invention can be operatively linked to a non-hydantoinase polypeptide (e.g., heterologous amino acid sequences) to form fusion proteins. As used herein, a hydantoinase "chimeric protein" or "fusion protein" comprises a hydantoinase polypeptide operatively linked to a non-hydantoinase polypeptide.

For example, in one embodiment, the fusion protein is a GST-hydantoinase fusion protein in which the hydantoinase sequences are fused to the C-terminus of the GST sequences. Such fusion proteins can facilitate the purification of recombinant hydantoinase. In another embodiment, the fusion protein is a hydantoinase protein containing a heterologous signal sequence at its N-terminus. In certain host cells (e.g., mammalian and yeast host cells), expression and/or secretion of hydantoinase can be increased through use of a heterologous signal sequence.

A signal sequence can be used to facilitate secretion and isolation of a protein or polypeptide of the invention. Signal sequences are typically characterized by a core of hydrophobic amino acids that are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by art-recognized processes. Alternatively, the signal sequence can be linked to the protein of interest using a sequence, which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al, Proc. Natl. Acad. Sci. USA 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., Cell 37:767 (1984), for instance.

Preferably, a chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example. Current Protocols in Molecular Biology, eds. Ausubel et al. John Wiley & Sons: 1992). Moreover, many expression vectors are commercially available that already encode a fusion moiety (e.g, a GST polypeptide). A nucleic acid according to the invention can be cloned into such an expression vector such that the fusion moiety is linked in-frame to the fusion moiety in order to express a fusion protein comprising a protein according to the invention.

The term "conservative substitution" or substitution by "homologous" amino acid residues is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Conservative amino acid substitutions usually have minimal impact on the activity of the resultant protein. Such substitutions are described below. Conservative substitutions replace one amino acid with another amino acid that is similar in size, hydrophobicity, charge, polarity, steric features, aromaticity etc. Such substitutions generally are conservative when it is desired to finely modulate the characteristics of the protein.

"Homologous" amino acid residues as used herein refer to amino acid residues which have similar chemical properties concerning hydrophobicity, charge, polarity, steric features, aromatic feature etc. Examples for amino acids which are homologous to each other include in terms of positive charge lysine, arginine, histidine; in terms of negative charge: glutamic acid, aspartic acid; in terms of hydrophobicity: glycine, alanine, valine, leucine, isoleucine, proline, phenylalanine; in terms of polarity serine, threonine, cysteine, methionine, tryptophan, tyrosine, asparagine, glutamine; in terms of aromaticity: phenylalanine, tyrosine, tryptophan; in terms of chemically similar side groups: serine and threonine; or glutamine and asparagines; or leucine and isoleucine.

Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first process relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, supra, and the references cited therein.

As defined herein, the term "substantially homologous" refers to a first amino acid sequence which contains a sufficient or minimum number of identical or equivalent (e.g., with similar side chain) amino acids to a second amino acid sequence such that the first and the second amino acid sequences have a common domain. For example, amino acid sequences which contain a common domain having about 80%, 85%, 90%, 95%, 96%, 97%, 98% or 99% identity or more are defined herein as sufficiently identical, with the provision that the substitution(s) of the amino acid positions according to the present invention as defined herein are maintained.

Also, nucleic acids encoding other hydantoinase family members, which thus have a nucleotide sequence that differs from a nucleotide sequence of the present invention are within the scope of the invention with the provision that the substitution(s) of the amino acid positions in the encoded amino acid sequence according to the present invention as defined herein are maintained. Such nucleic acid molecules corresponding to variants (e.g. natural allelic variants) and homologues of the DNA according to the invention can be isolated based on their homology to the nucleic acids disclosed herein using the cDNAs disclosed herein or a suitable fragment thereof, as a hybridisation probe according to standard hybridisation techniques preferably under highly stringent hybridisation conditions.

In addition to naturally occurring allelic variants of the sequences provided herein, the skilled person will recognise that further changes can be introduced by mutation into the nucleotide sequences according to the present invention thereby leading to changes in the amino acid sequence of the hydantoinase protein without substantially altering the function of the protein, with the provision that the substitution(s) of the amino acid positions in the encoded amino acid sequence according to the present invention as defined herein are maintained.

According to the present invention improved hydantoinases are provided. Improved hydantoinases are proteins wherein catalytic activity and/or enantioselectivity is improved. Such proteins may be obtained by randomly introducing mutations along all or part of the coding sequence, such as by saturation mutagenesis, and the resulting mutants can be expressed recombinantly and screened for the respective biological activity. For instance, the art provides for standard assays for measuring the catalytic activity of hydantoinases and thus improved proteins may easily be selected.

As used herein, the terms "gene" and "recombinant gene" refer to nucleic acid molecules which may be isolated from chromosomal DNA, which include an open reading frame encoding a protein, e.g. hydantoinase. A gene may include coding sequences, non-coding sequences, introns and regulatory sequences. Moreover, a gene refers to an isolated nucleic acid molecule as defined herein.

A nucleic acid molecule of the present invention or a functional equivalent thereof, can be isolated using standard molecular biology techniques and the sequence information provided herein. For example, using all or a portion of the nucleic acid sequence described herein as a hybridization probe, nucleic acid molecules according to the invention can be isolated using standard hybridization and cloning techniques (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989).

Moreover, a nucleic acid molecule encompassing all or a portion of the nucleic acid sequence according to the present invention can be isolated by the polymerase chain reaction (PCR) using synthetic oligonucleotide primers designed based upon the sequence information contained in the described sequences.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridisable to nucleotide sequences according to the invention can be prepared by standard synthetic techniques, e.g., using an automated DNA synthesizer.

A nucleic acid molecule that is complementary to another nucleotide sequence is one that is sufficiently complementary to the other nucleotide sequence such that it can hybridize to the other nucleotide sequence thereby forming a stable duplex.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Also included within the scope of the invention are the complement strands of the nucleic acid molecules described herein.

The sequence information as provided herein should not be so narrowly construed as to require inclusion of erroneously identified bases. The specific sequences disclosed herein can be readily used to isolate the complete gene from *Arthrobacter* sp. which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing processes well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct such errors.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e. overlapping positions)*100). Preferably, the two sequences are the same length.

The skilled person will be aware of the fact that several different computer programmes are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity two amino acid or nucleotide sequence is determined using the algorithm of E. Meyers and W. Miller (CABIOS, 4:11-17 (1989) which has been incorporated into the ALIGN program (version 2.0) (available at: http/vega.igh.cnrs.frlbin/align-guess.cgi) using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the BLASTN and BLASTX programs (version 2.0) of Altschul, et al. (1990) J. Mol. Biol. 215:403-10. BLAST nucleotide searches can be performed with the BLASTN program, score=100, word length=12 to obtain nucleotide sequences homologous to PLP03 nucleic acid molecules of the invention. BLAST protein searches can be performed with the BLASTX program, score=50, word length=3 to obtain amino acid sequences homologous to PLP03 protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., BLASTX and BLASTN) can be used. See http://www.ncbi.nlm.nih.gov.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

As used herein, the term "hybridizing" is intended to describe conditions for hybridization and washing under which nucleotide sequences at least about 90%, preferably at least about 95%, even more preferably at least about 96%, more preferably at least 98% homologous to each other typically remain hybridized to each other. The skilled person in the art understands that a further provision applies, namely that the substitution(s) of the amino acid positions in the encoded amino acid sequence according to the present invention as defined herein are maintained A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55'C, further preferred at 60° C. and even more preferably at 65° C.

Highly stringent conditions include, for example, hybridizing at 68° C. in 5×SSC/5×Denhardt's solution/1.0% SDS and washing in 0.2*SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

The present invention also relates to nucleic acid constructs comprising an isolated polynucleotide of the present invention operably linked to one or more control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA processes are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothemnnophilus* maltogenic amylase gene (amyM), *Bacillus amyloliquefaciens* alpha-amylase gene (amyQ), *Bacillus licheniformis* penicillinase gene (penP), *Bacillus subtilis* xyIA and xyIB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

As a ribosome binding sequence, any sequence can be used as long as it can be expressed in a host cell. However, it is preferable to use a plasmid in which a Shine-Dalgarno sequence and an initiation codon are adjusted to have an adequate distance (e.g., 6 to 18 bases) therebetween.

In order to efficiently carry out transcription and translation, a protein, in which the N-terminal of a protein having activity of the protein or a protein derived from such a protein by deletion of a portion thereof is fused with the N-terminal of a protein encoded by an expression vector, may be expressed.

The control sequence may also be a suitable transcription terminator sequence, a sequence recognized by a host cell to terminate transcription. Although a transcription termination sequence is not always necessary for the expression of a protein of interest, it is normally part of commercially available vectors. The terminator sequence is operably linked to the 3' terminus of the nucleotide sequence encoding the polypeptide. It is preferable to place a transcription termination sequence directly below a structural gene Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be transformed to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase.

Where both signal peptide and propeptide regions are present at the amino terminus of a polypeptide, the propeptide region is positioned next to the amino terminus of a polypeptide and the signal peptide region is positioned next to the amino terminus of the propeptide region. It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

In order to identify and select these transformants, a gene that encodes a selectable marker (e.g., resistance to antibiotics) is generally introduced into the host cells along with the gene of interest. The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Cells transformed with the introduced nucleic acid can be identified by drug selection (e.g. cells that have incorporated the selectable marker gene will survive, while the other cells die). Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof.

The vectors of the present invention may contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements. Such regulatory sequences are described, for example, in Goeddel; Gene Expression Technology: Methods in Enzymology 185, Academic Press, San Diego, Calif. (1990). Regulatory sequences include those which direct constitutive or inducible expression of a nucleotide sequence in many types of host cells.

The DNA insert should be operatively linked to an appropriate promoter, such as the phage lambda PL promoter, the *E. coli* lacI and lacZ promoters, the T3 and T7 promoters, the gpt promoter, the lambda PR, PL promoters and the trp promoter, the HSV thymidine kinase promoter, the early and late SV40 promoters, the promoters of retroviral LTRs, such as those of the Rous sarcoma virus ("RSV"), CMV (cytomegalovirus) and metallothionein promoters, such as the mouse metallothionein-I promoter. The skilled person will know other suitable promoters. Expression of proteins in prokaryotes is often carried out in *E. coli* with vectors containing constitutive or inducible promoters directing the expression of proteins. In a specific embodiment, promoters are preferred that are capable of directing a high expression level of hydantoinases in microorganisms, preferably in *E. coli, Bacillus* sp. coryneform bacteria. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipid mediated transfection or electroporation. Suitable processes for transforming or transfecting host cells can be found in Sambrook, et al. (Molecular Cloning: A Laboratory Manual, $2^{nd}$, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

Among vectors preferred for use in bacteria are pQE70, pQE60 and PQE-9, available from Qiagen; pBS vectors, Phagescript vectors, Bluescript vectors, pNH8A, pNH16A, pNH18A, pNH46A, available from Stratagene; and ptrc99a, pKK223-3, pKK233-3, pDR540, pRIT5 available from Pharmacia. Among preferred eukaryotic vectors are PWL-NEO, pSV2CAT, pOG44, pZT1 and pSG available from Stratagene; and pSVK3, pBPV, pMSG and pSVL available from Pharmacia. Other suitable vectors will be readily apparent to the skilled artisan.

The present invention also relates to recombinant host cells, comprising a polynucleotide of the present invention, which are advantageously used in the recombinant production of the hydantoinase polypeptides. A vector comprising a polynucleotide of the present invention is introduced into a host cell so that the vector is maintained as a chromosomal integrant or as a self-replicating extrachromosomal vector. The term "host cell" encompasses also any progeny of a parent cell that is not identical to the parent cell due to mutations that occur during replication. The choice of a host cell will to a large extent depend upon the gene encoding the polypeptide and its source.

Reference is also made to a "transformed cell" or "recombinant cell" which is a (host) cell into which (or into an ancestor of which) has been introduced, by means of recombinant DNA techniques, a nucleic acid according to the invention.

Both prokaryotic and eukaryotic cells are included, e.g., bacteria, fungi, yeast, and the like. In particular, useful microorganisms as host cells are bacterial cells such as gram positive or gram negative bacteria, including, but not limited to *Bacillus* sp. e.g., *Bacillus subtilis, Streptomyces* sp., *E. coli, Pseudomonas* sp., *Salmonella typhimurium*, coryneform bacteria, and also Actinomycetes, fungal cells, such as yeast, animal cells and plant cells.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizen, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The following example provides additional details regarding the procedures used to identify and isolate the modified hydantoinases in accordance with the present invention. The present invention is not limited to the description of the examples.

EXAMPLES

Example 1: Cloning and Expression of Hydantoinase

*Arthrobacter* sp. hydantoinase (HyuH) having amino acid sequence SEQ ID NO: 1 was supplied in a pOM18 vector. For further manipulation, sub-cloning with correct orientation of the HyuH gene was required. NdeI and HindIII were used for double digestion of pOM18 vectors. Vector backbone, carbA gene (carbamoylase) from pAS6 and HyuH gene from pOM18 were gel extracted PCR. All three gel extracted products were column purified (Machery Nagel) and subjected for ligation and subsequent transformation in *E. coli* DH5α. Clones were grown over night in LB-amp and culture PCR of was performed using gene specific forward primer from carbA and reverse primer to check for correct orientation. The plasmid pAS6-HyuH obtained contained the wild-type hydantoinase gene, expressing the protein having amino acid sequence SEQ ID NO: 1 and carbamoylase gene expressing the protein having amino acid sequence SEQ ID NO: 4. Plasmids of the desired clone were prepared and were transformed in JM109 cells containing pOM21c (plasmid expressing hydantoin racemase) for expression and activity check. For expression analysis, pre-culture was grown in LB media (with appropriate antibiotics) for overnight at 37. 10 µl of pre-culture was added to 3 ml inducing medium (LB media+2 mg/ml rhamnose). The culture was grown for 20 h at 30° C. 5 µl of cells were subjected for SDS PAGE analysis. Fluorescence based screening assay was used for checking the activity of the enzyme.

Example 2: Mutants of Hydantoinase

Several sites within the wild-type *Arthrobacter* sp. hydantoinase (SEQ ID NO: 1) were determined for mutagenesis. A mutant library was prepared by saturation mutagenesis at the amino acid positions elected. Then the rational mutant library was screened for increased activity using the high throughput screening assay. 5 sites for site saturation (Y72, 195, V154, P155, H316) and 2 sites for mutagenesis (A152G, S153G) were selected. For the determined amino acid positions 5 site saturation mutagenesis and 1 site directed mutation were performed.

Example 2.1: Construction of Focused Mutant Libraries (SSM & SDM)

Phusion polymerase was applied for site saturation mutagenesis (ssm) and site directed mutagenesis (sdm) using the plasmid obtained in example 1 (pAS6-HyuH; FIG. 1) expressing wild-type hydantoinase or in a subsequent step a plasmid carrying a mutant of said hydantoinase.

For site saturation/directed mutagenesis a two step PCR approach was applied for generation of focused mutant libraries. The PCR product was column purified and subjected for overnight DpnI digestion to remove the parent plasmid. The product representing a full-length plasmid having all elements of pAS6-HyuH was then transformed in JM109 cells containing pOM21c.

In detail: a two step PCR protocol was followed for site saturation/directed mutagenesis (SSM). 50 µl PCR reaction mixture contained 1 ng/µl of plasmid template, 1× Phusion buffer (New England Biolabs, Frankfurt, Germany), 1 U of Phusion polymerase and 300 µM dNTP's. The reaction mixture was divided in two equal volumes and 400 nM of forward primer and reverse primer for site saturation of the respective amino acid position (see table 1) were added to separate reaction mixtures. PCR program was 98° C. for 45 sec (1 cycle); 98° C. for sec; 65° C. for 30 sec; 72° C. for 3 min 30 sec (5 cycles); 72° C. for 5 min (1 cycle). After the first step both reactions were pooled and the same program with 18 more repetitions was carried out.

Table 1 summarizes the primers (F=forward primer; R=reverse primer) used for the described PCR methods, also indicating the amino acid position of SEQ ID NO: 1 to be modified.

Example 2.2: Construction of Random Mutant Libraries of *Arthrobacter* sp. Hydantoinase (HyuH)

For generation of epPCR mutant library error prone conditions were generated using $MnCl_2$. PCR was initially performed by varying $MnCl_2$ concentration (0.05 mM, 0.1 mM, 0.2 mM, 0.5 mM). The reaction mixture contained 0.3 ng/µl of plasmid template (using the plasmid obtained in example 1 [pAS6-HyuH; FIG. 1] expressing wild-type hydantoinase or at a later stage of the studies a plasmid carrying a mutant of said hydantoinase obtained), 1× SeSaM® Taq buffer (SeSaM-Biotech GmbH, Bremen, Germany), 1 U of SeSaM® Taq polymerase, 200 µM dNTPs and 250 nM of HyuH_GS_F and HyuH_R primers shown in table 1 each along with variable $MnCl_2$ concentration. The PCR program was 94C for 2 min (1 cycle); 94C for 30 sec; 56° C. for 30 sec; 72° C. for 50 sec (25 cycles); 72° C. for 5 min (1 cycle). SeSaM® protocol (Mundhada et al. "SeSaM-Tv-II generates a protein sequence space that is unobtainable by epPCR" Chembiochem. 2011 Jul. 4; 12(10):1595-601) was used to construct transversion biased mutant library. The PCR products were column purified and subjected for Megawhop for cloning. 50 µl PCR reaction mixtures contained 1 ng/µl of plasmid template, 1× Phusion buffer (New England Biolabs, Frankfurt, Germany), 1 U of Phusion polymerase, 300 µM dNTP's and 5 ng/µl of mutated template from epPCR or SeSaM®. PCR program for Megawhop was 72° C. 3 min (1 cycle); 98° C. 45 sec (1 cycle); 98° C. for sec; 62° C. for 30 sec; 72° C. for 5 min (25 cycles); 72° C. for 5 min (1 cycle). The PCR mix was then column purified and subjected to overnight DpnI (10 U) digestion. The PCR product representing a full length plasmid having all elements of pAS6-HyuH was transformed in chemically competent JM109 cells (Promega, Mannheim, Germany) for protein expression and subsequent analysis.

Example 2.3: Construction of Focused Omnichange Mutant Libraries

The protocol for Omnichange allows multiple site saturation mutagenesis at remote positions in the sequence. It proceeds in four steps, starting which Fragment generation by PCR with primers containing NNK-codons and phosphorothiodiester bonds, then DNA-cleavage reaction with elemental iodine for the generation of complementary 5'-overhangs, thirdly DNA-hybridization and finally transformation and nick repair.

In detail, 50 µl PCR reaction mixture contained 0.5 ng/µl of plasmid template, 1× Phusion buffer (New England Biolabs. Frankfurt. Germany), 5 U of Phusion polymerase, 200 µM dNTP's and 400 µM fragment specific forward and reverse primer. The PCR program for the short fragment was 94C for 3 min (1 cycle); 94C for 30 sec; 55° C. for 30 sec; 72° C. for 30 sec (25 cycles); 72° C. for 1 min (1 cycle). For the vector fragment the PCR program was changed to 94° C. for 3 min (1 cycle); 94° C. for 30 sec; 55° C. for 30 sec; 72°

C. for 1.5 min (25 cycles); 72° C. for 3 min (1 cycle). The PCR mixes was then column purified and subjected to overnight DpnI (10 U) digestion, column purified and diluted to 0.05 pmol/μl. Iodine cleavage and DNA-fragment hybridization were performed according to the original Omnichange protocol (Dennig et al. "OmniChange: The Sequence Independent Method for Simultaneous Site-Saturation of Five Codons" PLoS ONE, 2011, 6(10): e26222). The hybridization products were then transformed in chemically competent JM109 cells (Promega, Mannheim, Germany) for protein expression and subsequent analysis.

Example 3: Fluorescence Based Screening Assay for Microtiter Plates (MTP)

Pre-culture and expression: 100 μl of LB medium containing the appropriate antibiotic in 96-well microtiter plates (MTP) were inoculated with positive and negative controls as well as obtained clones using a tooth pick. The plates were incubated at 37° C. (900 rpm) overnight. For preparing screening plates, clones were transferred to a new MTP with 200 μl/well of medium with antibiotic and 2 mg/mL rhamnose using a 96-well replicator. To the remaining material of the plates 100 μL of 50% glycerol (w/w) was added, briefly mixed and plates were stored at −80° C.

Biotransformation: After incubation at 30° C. (900 rpm) overnight, 100 μL/well of homogenized L- or D-tryptophan hydantoin suspension (5 mg/mL in PBS buffer pH 7.4) was added to the screening plates. The plates were incubated at 30° C. and 900 rpm and fluorescence was measured at 300/350 nm with a suitable plate reader at different time points.

Example 4: Results

The mutant hydantoinases obtained from the site saturation mutagenesis experiment and random mutagenesis library according to example 2 were screened in respect of their activity using the fluorescence assay described in example 3. The readout referred to the differential measurement between 40 min and 60 min. Each measurement was carried out in triplicate. As described above the mutant hydantoinases were assayed with respect to their activity using as substrates L-5-indolylmethylhydantoin (=L-tryptophan hydantoin) and D-5-indolylmethylhydantoin (=D-tryptophan hydantoin), respectively, and their activities were compared to the activity of the wild-type hydantoinase having amino acid sequence SEQ ID NO: 1.

In table 2 the results obtained were summarized. As shown there a series of improved mutants were obtained showing higher catalytic activity and/or higher enantioselectivity compared to the wild-type hydantoinase produced by the microorganism *Arthrobacter* sp. having amino acid sequence SEQ ID NO: 1.

In table 2, the column "mutagenesis round" indicates from which type of mutagenesis the mutant is derived (SSM=site saturation mutagenesis; epPCR=error prone PCR; combi SSM=combinatorial site saturation mutagenesis, a mutagenesis at more than one amino acid position). In the column designated "substitutions" the substitution of an amino acid residue at the given position in amino acid sequence SEQ ID NO: 1 is indicated.

The column designated "Activity ratio of D-Trp-hyd to HyuH wt" shows the fold improvement of catalytic activity with respect to wild type hydantoinase using 0-5-indolylmethylhydantoin (=D-tryptophan hydantoin) as substrate. The column designated "Activity ratio of L-Trp-hyd to HyuH wt" shows the fold improvement of activity with respect to wild type hydantoinase using L-5-indolylmethylhydantoin (=L-tryptophan hydantoin) as substrate.

The column "Activity Ratio of D-Trp-hyd to L-Trp-hyd" indicates the ratio of the catalytic activity of the mutant hydantoinase for transforming D-5-indolylmethylhydantoin versus the activity of the mutant hydantoinase for transforming L-5-indolylmethylhydantoin and shows fold excess preference for either enantiomer. In other words, the column "Activity Ratio of D-Trp-hyd to L-Trp-hyd" indicates the enantioselectivity of the respective hydantoinase.

The hydantoinase according to the present invention showed enhanced transformation rates in respect of 5-substituted hydantoin compounds, in particular D-tryptophan hydantoin. Therefore, the hydantoinase mutants according to the present invention described herein were considered suitable in a process for the production of D-amino acids, in particular D-tryptophan, starting from the D-tryptophan hydantoin using the mutant hydantoinase according to the present invention, as well as D-carbamoylase.

TABLE 1

List of primers and their sequences. Name of the primer denotes the targeted site for focused mutant libraries.

| amino acid position(s) (F = forward primer; R = reverse primer) | SEQ ID NO: | Purpose | Sequence |
|---|---|---|---|
| Y72 (F) | 21 | ssm | ATC TGA AGA ACC GGN NKG GCC GCT TCG AAC T |
| Y72 (R) | 22 | ssm | AGT TCG AAG CGG CCM NNC CGG TTC TTC AGA T |
| I95 (F) | 23 | ssm | CAT CGA GAT GCC GNN KAC CTT CCC GCC CAC |
| I95 (R) | 24 | ssm | GTG GCG GGG AAG GTM NNC GGC ATC TCG ATG |
| V154 (F) | 25 | ssm | TGA TGG CAG CCT CAN NKC CGG GCA TGT TCG |
| V154 (R) | 26 | ssm | CGA ACA TGC CCG GMN NTG AGG CTG CCA TCA |
| P155 (F) | 27 | ssm | TGG CAG CCT CAG TTN NKG GCA TGT TCG ACG |

TABLE 1-continued

List of primers and their sequences. Name of the primer denotes the targeted site for focused mutant libraries.

| amino acid position(s) (F = forward primer; R = reverse primer) | SEQ ID NO: | Purpose | Sequence |
|---|---|---|---|
| P155 (R) | 28 | ssm | GCG TCG AAC ATG CCM NNA ACT GAG GCT GCC A |
| G156 (F) | 29 | ssm | CAG CCT CAG TTC CGN NKC AGC CTC AGT TCC G |
| G156 (R) | 30 | ssm | CGG AAC TGA GGC TGM NNC GGA ACT GAG GCT G |
| H316 (F) | 31 | ssm | CCC TTG GGT CAG ACN NNK GCG GAC ATC CTG |
| H316 (R) | 32 | ssm | CAG GAT GTC CGC CMN NGT CTG ACC CAA GGG |
| A285 (F) | 33 | ssm | CGT ATA TGA AGG TCN NKC CGC CCG TCC GCT CA |
| A285 (R) | 34 | ssm | TGA GCG GAC GGG CGG MNN GAC CTT CAT ATA CG |
| V284 (F) | 35 | ssm | GAC CGT ATA TGA AGN NKG CGC CGC CCG TC |
| V284 (R) | 36 | ssm | GAC GGG CGG CGC MNN CTT CAT ATA CGG TC |
| P94 (F) | 37 | ssm | CAC CAT CAT CGA GAT GNN KAT AAC CTT CCC G |
| P94 (R) | 38 | ssm | CGG GAA GGT TAT MNN CAT CTC GAT GAT GGT G |
| P98 (F) | 39 | ssm | TGC CGA TAA CCT TCN NKC CCA CCA CCA CTT GG |
| P98 (R) | 40 | ssm | CCA AGT GGT GGT GGG MNN GAA GGT TAT CG GCA |
| P99 (F) | 41 | ssm | CGA TAA CCT TCC CGN NKA CCA CCA CTT TGG AC |
| P99 (R) | 42 | ssm | GTC CAA AGT GGT GGT MNN CGG GAA GGT TAT CG |
| R71 (F) | 43 | ssm | GGA TCT GAA GAA CNN KTA TGG CCG CTT CGA AC |
| R71 (R) | 44 | ssm | GTT CGA AGC GGC CAT AMN NGT TCT TCA GAT CC |
| A152 (F) | 45 | ssm | CAA GTC AAT GAT GGC ANN KTC AGT TCC GGG C |
| A152 (R) | 46 | ssm | GCC CGG AAC TGA MNN TGC CAT CAT TGA CTT G |
| F158 (F) | 47 | ssm | CAG TTC CGG GCA TGN NKG ACG CCG TCA GCG AC |
| F158 (R) | 48 | ssm | GTC GCT GAC GGC GTC MNN CAT GCC CGG AAC TG |
| R71 Y72 (F) | 49 | combinatorial ssm | CAT GGA TCT GAA GAA CND TND TGG CCG CTT CGA ACT C |
| R71 Y72 (R) | 50 | combinatorial ssm | GAG TTC GAA GCG GCC AHN AHN GTT CTT CAG ATC CAT G |
| A152 V154 (F) | 51 | combinatorial ssm | GCT TCA AGT CAA TGA TGG CAN DTT CAN DTC CGG GCA TGT TCG AC |
| A152 V154 (R) | 52 | combinatorial ssm | GTC GAA CAT GCC CGG AHN TGA AHN TGC CAT CAT TGA CTT GAA GC |
| A284 A285 (F) | 53 | combinatorial ssm | GGA CCG TAT ATG AAG NDT NDT CCG CCC GTC CGC TC |
| V284 A285 (R) | 54 | combinatorial ssm | GAG CGG ACG GGC GGA HNA HNC TTC ATA TAC GGT CC |
| I65 (F) | 55 | ssm | GAA CAT GTG CAT ATC NNK GAC ATG GAT CTG AAG |
| I65 (R) | 56 | ssm | CTT CAG ATC CAT GTC MNN GAT ATG CAC ATG TTC |
| HyuH_R | 57 | gene specific reverse primer of HyuH | TCA CTT CGA CGC CTC GTA GTC G |

TABLE 1-continued

List of primers and their sequences. Name of the primer denotes the targeted site for focused mutant libraries.

| amino acid position(s) (F = forward primer; R = reverse primer) | SEQ ID NO: | Purpose | Sequence |
|---|---|---|---|
| HyuH_GS_F | 58 | gene specific forward primer for epPCR | ATG TTT GAC GTA ATA GTT AAG AAC TGC CG |
| SeSaMR_HyuHR2 | 59 | SeSaM library construction | GTG TGA TGG CGT GAG GCA GCC TAC TGC CGC CAG GCA AAT TCT |
| SEeSaMF_carbAF | 60 | SeSaM library construction | CAC ACT ACC GCA CTC CGT CGC GTC AGC CAC AGC ACT ACG G |
| S14 (F) | 61 | OmniChange | cgtatggtgtccNNKGACGGAATCACCGAG |
| S14 (R) | 62 | OmniChange | ggacaccatacgGCA GTT CTT AAC TAT TAC G |
| S37 (F) | 63 | OmniChange | agctcggacacaNNKGATGTTGAGGCGAG |
| S37 (R) | 64 | OmniChange | tgt gtc cga gct GAT TGC GGC G |
| S153 V154 (F) | 65 | combi ssm | GTCAATGATGGCAAGTNDTDNYCCGGGCATGTTCGACG |
| S153 V154 (R) | 66 | combi ssm | CGT CGA ACA TGC CCG GRN HAH NAC TTG CCA TCA TTG AC |
| S14 D15 (F) | 67 | combi ssm | CCGTATGGTGICCBBTNNKGGAATCACCGAGG |
| S14 D15 (R) | 68 | combi ssm | CCT CGG TGA TTC CMN NAV VGG ACA CCA TAC GG |
| C64I (F) | 69 | sdm | GAACATGTGCATATCATCGACATGGATCTGAAGA |
| C64I (R) | 70 | sdm | TCT TCA GAT CCA TGT CGA TGA TAT GCA CAT GTT C |
| S152A (F) | 71 | sdm | CAA GTC AAT GAT GGC AGC CTC AGT TCC GGG CAT G |
| S152A (R) | 72 | sdm | CAT GCC CGG AAC TGA GGC TGC CAT CAT TGA CTT G |

TABLE 2

Summary of activity and selectivity of all HyuH mutants.

| Name of mutant | mutagenesis round | Substitutions | Activity Ratio of D-Trp-hyd to HyuH wt | Activity Ratio of L-Trp-hyd to HyuH wt | Activity Ratio of D-Trp-hyd to L-Trp-hyd |
|---|---|---|---|---|---|
| P2.2 | SSM - I95 | I95H | ~1.2 | ~1.2 | ~1 |
| P3.1 | SSM - V154 | V154G | ~1.3 | ~1.3 | ~1 |
| P6.1 | SSM - V154 | V154N | ~1.3 | ~1.3 | ~1 |
| P15.2 | SSM - R71 | R71Q | 1.0 | 1.0 | 0.97 |
| P24.3 | SSM - R71 | R71D | 1.9 | 1.9 | 1.76 |
| P25.2 | SSM - R71 | R71E | 1.9 | 1.2 | 1.58 |
| P32.2 | SSM - A152 | A152G | 4.0 | 0.9 | 4.61 |
| P33.18 | SSM - A152 | A152T | 3.3 | 1.0 | 3.21 |
| P34.8 | SSM - V284 | V284F | 1.8 | 1.1 | 1.60 |
| P37.1 | SSM - A285 | A285D | 1.1 | 0.2 | 6.19 |
| P3.11 | SSM - V154 | V154A | 2.0 | 0.67 | 3.03 |
| P7.3 | epPCR | I64T | 2.1 | 0.31 | 6.87 |
| P7.4 | epPCR | I64V | 1.9 | 0.54 | 3.49 |
| P10.1 | epPCR | V154S | 1.6 | 0.34 | 4.84 |
| P18.1 | epPCR | V154A, T398A, H452L | 1.4 | 0.29 | 4.89 |
| P52.2 | Combi SSM | A152S, V154I | 7.26 | 0.43 | 16.76 |
| P52.7 | Combi SSM | A152V, V154C | 1.38 | 0.23 | 6.07 |
| P53.2 | Combi SSM | A152C, V154S | 6.49 | 0.44 | 14.86 |
| P53.3 | Combi SSM | A152S | 5.09 | 0.95 | 5.34 |

TABLE 2-continued

Summary of activity and selectivity of all HyuH mutants.

| Name of mutant | mutagenesis round | Substitutions | Activity Ratio of D-Trp-hyd to HyuH wt | Activity Ratio of L-Trp-hyd to HyuH wt | Activity Ratio of D-Trp-hyd to L-Trp-hyd |
|---|---|---|---|---|---|
| P56.3 | Combi SSM | R71D, Y72H, A152S | 5.26 | 0.37 | 14.33 |
| P56.9 | Combi SSM | R71V, Y72N, A152S | 4.03 | 0.19 | 20.74 |
| P59.1 | Combi SSM | R71S, Y72N, A152C, V154S, V181A | 3.73 | 0.13 | 29.79 |
| P60.5 | Combi SSM | R71D, Y72N, A152S | 3.73 | 0.07 | 54.61 |
| P61.1 | Combi SSM | R71Y, Y72N, A152S | 4.13 | 0.03 | 131.16 |
| P62.1 | Combi SSM | R71L, A152C, V154S | 4.79 | 0.13 | 36.85 |
| P62.2 | Combi SSM | R71Y, Y72H, A152S | 3.66 | 0.06 | 57.15 |
| P76.1 | SSM5 - I64 | I64V, R71I, Y72N, A152S | 10.97 | 0.04 | 245.23 |
| P83.2 | SSM5 - I64 | I64C, R71Y, Y72N, A152S | 6.76 | 0.08 | 89.72 |
| P84.1 | SSM5 - I64 | I64C, R71D, Y72H, A152S | 4.48 | 0.13 | 34.57 |
| P106.2 | epPCR2 | I64C, R71D, Y72H, A152S, F448L | 6.05 | 0.06 | 93.63 |
| P110.1 | epPCR2 | I64C, R71D, Y72H, A152S, M417V | 5.62 | 0.14 | 39.90 |
| P111.1 | epPCR2 | S14G, I64C, R71D, Y72H, A152S | 3.50 | 0.15 | 23.11 |
| P112.1 | epPCR2 | S37R, I64C, R71D, Y72H, A152S | 3.74 | 0.14 | 26.68 |
| P119.1 | epPCR2 | S14G, I64C, R71D, Y72H, A152S, E358K | 9.12 | 0.05 | 181.46 |
| P121.1 | epPCR3 | S37R, I64C, R71D, Y72H, A152S, V318A | 10.15 | 0.08 | 120.79 |
| P128.1 | epPCR3 | S37R, I64C, R71D, Y72H, A152S, N303S, Q404R | 9.50 | 0.07 | 136.72 |
| P130.1 | epPCR3 | S14G, I64C, R71D, Y72H, A152S, N70D | 4.93 | 0.06 | 76.53 |
| P132.3 | epPCR3 | S14G, I64C, R71D, Y72H, A152S, V154A | 5.31 | 0.01 | 480.31 |
| P137.1 | Omnichange | S37G, I64C, R71D, Y72H, A152S | 21.47 | 0.20 | 150.97 |
| P138.1 | Omnichange | S14A, S37G, I64C, R71D, Y72H, A152S | 21.13 | 0.20 | 180.00 |
| P140.1 | Omnichange | S14V, I64C, R71D, Y72H, A152S | 21.42 | 0.20 | 186.89 |
| P140.2 | Omnichange | S14G, S37G, I64C, R71D, Y72H, A152S | 21.49 | 0.20 | 187.98 |
| P143.1 | Omnichange | S14A, S37W, I64C, R71D, Y72H, A152S | 17.06 | 0.16 | 230.36 |
| P143.2 | Omnichange | S14A, S37V, I64C, R71D, Y72H, A152S | 19.97 | 0.19 | 187.91 |
| P143.3 | Omnichange | D15N, I64C, R71D, Y72H, A152S | 20.61 | 0.19 | 160.71 |
| P143.4 | Omnichange | S14V, S37R, I64C, R71D, Y72H, A152S | 20.58 | 0.19 | 171.64 |
| P146.1 | Combi SSM3 | D15N, I64C, R71D, Y72H, A152S, V154C | 4.61 | 0.04 | 129.72 |
| P148.3 | Combi SSM3 | D15N, I64C, R71D, Y72H, A152S, V154I | 4.18 | 0.07 | 60.60 |
| P152.4 | Combi SSM4 | S14P, D15G, S37G, I64C, R71D, Y72H, A152S | 11.63 | 0.21 | 56.37 |
| P152.5 | Combi SSM4 | S14G, D15R, S37G, I64C, R71D, Y72H, A152S | 16.92 | 0.06 | 277.95 |
| P153.2 | Combi SSM4 | S146, D150, S370, I64C, R71D, Y72H, A152S | 12.75 | 0.00 | 5069.66 |
| P153.3 | Combi SSM4 | S14F, D15A, S37G, I64C, R71D, Y72H, A152S | 10.46 | 0.10 | 110.01 |
| P156.1 | Combi SSM4 | D15S, S37G, I64C, R71D, Y72H, A152S | 6.75 | 0.17 | 38.67 |
| P161.7 | SDM C64I | S14P, D15G, S37G, R71D, Y72H, A152S | 4.01 | 0.08 | 52.00 |
| P161.9 | SDM S152A | S14P, D15G, S37G, I64C, R71D, Y72H | 2.42 | 0.06 | 41.82 |
| P162.9 | SDM S152A | D15S, S37G, I64C, R71D, Y72H | 3.19 | 0.10 | 31.84 |

The invention claimed is:

1. An isolated polynucleotide encoding an hydantoinase, wherein the catalytic activity of the hydantoinase encoded by the isolated polynucleotide is higher by a factor of at least 1.2 than the catalytic activity of an hydantoinase having the amino acid sequence of SEQ ID NO: 1, wherein the catalytic activity of an hydantoinase is the catalytic activity of the hydantoinase with respect to transformation of a 5-substituted D-hydantoin compound to the corresponding D-carbamoylamino acid, and wherein the isolated polynucleotide comprises a nucleotide sequence encoding an hydantoinase comprising an amino sequence selected from the group consisting of SEQ ID NO: 6, SEQ ID NO: 8, SEQ ID NO: 9, SEQ ID NO: 11, SEQ ID NO: 20, SEQ ID NO: 85, SEQ ID NO: 86, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, and SEQ ID NO: 117, or
   an amino acid sequence selected from the group consisting of SEQ ID NO: 6, SEQ ID NO: 8, SEQ ID NO: 9, SEQ ID NO: 11, SEQ ID NO: 20, SEQ ID NO: 85, SEQ ID NO: 86, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, and SEQ ID NO: 117, wherein 1 to 50 amino acid residues have been substituted, deleted, inserted and/or added, and
   wherein the amino acid substitutions present in the amino acid sequence of SEQ ID NO: 6, SEQ ID NO: 8, SEQ ID NO: 9, SEQ ID NO: 11, SEQ ID NO: 20, SEQ ID NO: 85, SEQ ID NO: 86, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, and SEQ ID NO: 117, as compared to the amino acid sequence of SEQ ID NO: 1 are maintained.

2. A vector comprising the isolated polynucleotide of claim 1.

3. A host cell comprising the isolated polynucleotide of claim 1.

4. The host cell according to claim 3, said host cell having at least the following enzymatic activities: hydantoinase and hydantoin racemase; hydantoinase and carbamoylase; or hydantoinase and hydantoin racemase and carbamoylase.

5. A host cell comprising a vector comprising the isolated polynucleotide of claim 1.

6. The host cell of claim 5, said host cell having at least the following enzymatic activities: hydantoinase and hydantoin racemase; hydantoinase and carbamoylase; or hydantoinase and hydantoin racemase and carbamoylase.

* * * * *

SEQUENCE LISTING

<160> NUMBER OF SEQ ID NOS: 119

<210> SEQ ID NO 1
<211> LENGTH: 458
<212> TYPE: PRT
<213> ORGANISM: Arthrobacter sp.

<400> SEQUENCE: 1

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Gly Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365
```

```
Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
    450                 455

<210> SEQ ID NO 2
<211> LENGTH: 1377
<212> TYPE: DNA
<213> ORGANISM: Arthrobacter sp.

<400> SEQUENCE: 2
```

| | |
|---|---:|
| atgtttgacg taatagttaa gaactgccgt atggtgtcca gcgacggaat caccgaggca | 60 |
| gacattctgg tgaaagacgg caaagtcgcc gcaatcagct cggacacaag tgatgttgag | 120 |
| gcgagccgaa ccattgacgc gggtggcaag ttcgtgatgc cgggcgtggt cgatgaacat | 180 |
| gtgcatatca tcgacatgga tctgaagaac cggtatggcc gcttcgaact cgattccgag | 240 |
| tctgcggccg tgggaggcat caccaccatc atcgagatgc cgataacctt cccgcccacc | 300 |
| accactttgg acgccttcct cgaaaagaag agcaggcgg gcagcggtt gaaagttgac | 360 |
| ttcgcgctct atggcggtgg agtgccggga aacctgcccg agatccgcaa aatgcacgac | 420 |
| gccggcgcag tgggcttcaa gtcaatgatg cagcctcag ttccgggcat gttcgacgcc | 480 |
| gtcagcgacg gcgaactgtt cgaaatcttc caggagatcg cagcctgtgg ttcagtcgtc | 540 |
| gtggtccatg ccgagaatga aacgatcatt caagcgctcc agaagcagat caaagccgct | 600 |
| ggtcgcaagg acatggccgc ctacgaggca tcccaaccag ttttccagga gaacgaggcc | 660 |
| attcagcgtg cgttactact gcagaaagaa gccggctgtc gactgattgt gcttcacgtg | 720 |
| agcaaccctg acggggtcga gctgatacat caggcgcaat ccgagggcca ggacgtccac | 780 |
| tgcgagtcgg gtccgcagta tctgaatatc accacggacg acgccgaacg aatcggaccg | 840 |
| tatatgaagg tcgcgccgcc cgtccgctca gccgagatga acgtcagatt atgggaacaa | 900 |
| cttgagaacg ggctcatcga caccctttggg tcagaccacg gcggacatcc tgtcgaggac | 960 |
| aaagaacccg gctggaagga cgtgtggaaa gccggcaacg gtgcgctggg ccttgagaca | 1020 |
| tccctgccta tgatgctgac caacggagtg aataaaggca ggctatcctt ggaacgcctc | 1080 |
| gtcgaggtga tgtgcgagaa acctgcgaag ctctttggca tctatccgca gaagggcacg | 1140 |
| ctacaggttg gttccgacgc cgatctgctc atcctcgatc tggatattga caccaaagtg | 1200 |
| gatgcctcgc agttccgatc cctgcataag tacagcccgt tcgacgggat gcccgtcacg | 1260 |
| ggtgcaccgg ttctgacgat ggtgcgcgga acggtggtgg cagagaaggg agaagttctg | 1320 |
| gtcgagcagg gattcggcca gttcgtcacc cgtcacgact acgaggcgtc gaagtga | 1377 |

```
<210> SEQ ID NO 3
<211> LENGTH: 236
<212> TYPE: PRT
<213> ORGANISM: Agrobacterium sp.

<400> SEQUENCE: 3
```

Met Arg Ile Leu Val Ile Asn Pro Asn Ser Ser Ala Leu Thr Glu
1               5                   10                  15

Ser Val Ala Asp Ala Ala Gln Gln Val Val Ala Thr Gly Thr Ile Ile
                20                  25                  30

Ser Ala Ile Asn Pro Ser Arg Gly Pro Ala Val Ile Glu Gly Ser Phe
            35                  40                  45

Asp Glu Ala Leu Ala Thr Phe His Leu Ile Glu Glu Val Glu Arg Ala
    50                  55                  60

Glu Arg Glu Asn Pro Pro Asp Ala Tyr Val Ile Ala Cys Phe Gly Asp
65                  70                  75                  80

Pro Gly Leu Asp Ala Val Lys Glu Leu Thr Asp Arg Pro Val Val Gly
                85                  90                  95

Val Ala Glu Ala Ala Ile His Met Ser Ser Phe Val Ala Thr Phe
                100                 105                 110

Ser Ile Val Ser Ile Leu Pro Arg Val Arg Lys His Leu His Glu Leu
            115                 120                 125

Val Arg Gln Ala Gly Ala Thr Asn Arg Leu Ala Ser Ile Lys Leu Pro
130                 135                 140

Asn Leu Gly Val Met Ala Phe His Glu Asp His Ala Ala Leu Glu
145                 150                 155                 160

Thr Leu Lys Gln Ala Ala Lys Glu Ala Val Gln Glu Asp Gly Ala Glu
                165                 170                 175

Ser Ile Val Leu Gly Cys Ala Gly Met Val Gly Phe Ala Arg Gln Leu
            180                 185                 190

Ser Asp Glu Leu Gly Val Pro Val Ile Asp Pro Val Glu Ala Ala Cys
            195                 200                 205

Arg Val Ala Glu Ser Leu Val Ala Leu Gly Tyr Gln Thr Ser Lys Ala
210                 215                 220

Asn Ser Tyr Gln Lys Pro Thr Glu Lys Gln Tyr Leu
225                 230                 235

<210> SEQ ID NO 4
<211> LENGTH: 306
<212> TYPE: PRT
<213> ORGANISM: Agrobacterium sp.

<400> SEQUENCE: 4

Met Thr Arg Gln Met Ile Leu Ala Val Gly Gln Gln Gly Pro Ile Ala
1               5                   10                  15

Arg Ala Glu Thr Arg Glu Gln Val Val Gly Arg Leu Leu Asp Met Leu
                20                  25                  30

Thr Asn Ala Ala Ser Arg Gly Val Asn Phe Ile Val Phe Pro Glu Leu
            35                  40                  45

Ala Leu Thr Thr Phe Phe Pro Arg Trp His Phe Thr Asp Glu Ala Glu
    50                  55                  60

Leu Asp Ser Phe Tyr Glu Thr Glu Met Pro Gly Pro Val Val Arg Pro
65                  70                  75                  80

Leu Phe Glu Thr Ala Ala Glu Leu Gly Ile Gly Phe Asn Leu Gly Tyr
                85                  90                  95

Ala Glu Leu Val Val Glu Gly Gly Val Lys Arg Arg Phe Asn Thr Ser
                100                 105                 110

Ile Leu Val Asp Lys Ser Gly Lys Ile Val Gly Lys Tyr Arg Lys Ile
            115                 120                 125

His Leu Pro Gly His Lys Glu Tyr Glu Ala Tyr Arg Pro Phe Gln His

```
                    130                 135                 140
Leu Glu Lys Arg Tyr Phe Glu Pro Gly Asp Leu Gly Phe Pro Val Tyr
145                 150                 155                 160

Asp Val Asp Ala Ala Lys Met Gly Met Phe Ile Cys Asn Asp Arg Arg
                165                 170                 175

Trp Pro Glu Thr Trp Arg Val Met Gly Leu Lys Gly Ala Glu Ile Ile
            180                 185                 190

Cys Gly Gly Tyr Asn Thr Pro Thr His Asn Pro Pro Val Pro Gln His
        195                 200                 205

Asp His Leu Thr Ser Phe His His Leu Leu Ser Met Gln Ala Gly Ser
    210                 215                 220

Tyr Gln Asn Gly Ala Trp Ser Ala Ala Ala Gly Lys Val Gly Met Glu
225                 230                 235                 240

Glu Gly Cys Met Leu Leu Gly His Ser Cys Ile Val Ala Pro Thr Gly
                245                 250                 255

Glu Ile Val Ala Leu Thr Thr Thr Leu Glu Asp Glu Val Ile Thr Ala
            260                 265                 270

Ala Val Asp Leu Asp Arg Cys Arg Glu Leu Arg Glu His Ile Phe Asn
        275                 280                 285

Phe Lys Ala His Arg Gln Pro Gln His Tyr Gly Leu Ile Ala Glu Phe
    290                 295                 300

Gly Ile
305
```

<210> SEQ ID NO 5
<211> LENGTH: 458
<212> TYPE: PRT
<213> ORGANISM: Artificial
<220> FEATURE:
<223> OTHER INFORMATION: mutant polypeptide
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (284)..(285)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (452)..(452)
<223> OTHER INFORMATION: Xaa can be any naturally occurring amino acid

<400> SEQUENCE: 5

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Xaa
    50                  55                  60

Asp Met Asp Leu Lys Asn Xaa Xaa Gly Arg Phe Glu Leu Asp Ser Glu
65                  70                  75                  80

Ser Ala Ala Val Gly Gly Ile Thr Thr Ile Ile Glu Met Pro Xaa Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Xaa Ser Xaa Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Xaa Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Xaa Xaa Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Xaa Lys Val
385                 390                 395                 400

Asp Ala Ser Gln Phe Arg Ser Leu His Lys Tyr Ser Pro Phe Asp Gly
                405                 410                 415
```

-continued

```
Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
            435                 440                 445

Val Thr Arg Xaa Asp Tyr Glu Ala Ser Lys
        450                 455

<210> SEQ ID NO 6
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (152)..(152)
<223> OTHER INFORMATION: A replaced by G

<400> SEQUENCE: 6

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Gly Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
```

```
                290                 295                 300
Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
                370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455

<210> SEQ ID NO 7
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (152)..(152)
<223> OTHER INFORMATION: A replaced by C

<400> SEQUENCE: 7

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
                20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Ile
        50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
                115                 120                 125

Pro Gly Asn Leu Pro Glu Ile Arg Lys Met His Asp Ala Gly Ala Val
            130                 135                 140

Gly Phe Lys Ser Met Met Ala Cys Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175
```

```
Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 8
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (152)..(152)
<223> OTHER INFORMATION: A replaced by S

<400> SEQUENCE: 8

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60
```

```
Asp Met Asp Leu Lys Asn Arg Tyr Gly Arg Phe Glu Leu Asp Ser Glu
 65                  70                  75                  80

Ser Ala Ala Val Gly Gly Ile Thr Thr Ile Glu Met Pro Ile Thr
             85                  90                  95

Phe Pro Pro Thr Thr Thr Leu Asp Ala Phe Leu Glu Lys Lys Lys Gln
             100                 105                 110

Ala Gly Gln Arg Leu Lys Val Asp Phe Ala Leu Tyr Gly Gly Gly Val
             115                 120                 125

Pro Gly Asn Leu Pro Glu Ile Arg Lys Met His Asp Ala Gly Ala Val
             130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
                210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
                275                 280                 285

Arg Ser Ala Glu Met Asn Val Arg Leu Trp Glu Gln Leu Glu Asn Gly
290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
                370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455
```

<210> SEQ ID NO 9
<211> LENGTH: 458

```
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (152)..(152)
<223> OTHER INFORMATION: A replaced by T

<400> SEQUENCE: 9
```

| | | | | | | | | | | | | | | |
|---|---|---|---|---|---|---|---|---|---|---|---|---|---|---|
| Met | Phe | Asp | Val | Ile | Val | Lys | Asn | Cys | Arg | Met | Val | Ser | Ser | Asp | Gly |
| 1 | | | | 5 | | | | | 10 | | | | | 15 | |

| | | | | | | | | | | | | | | |
|---|---|---|---|---|---|---|---|---|---|---|---|---|---|---|
| Ile | Thr | Glu | Ala | Asp | Ile | Leu | Val | Lys | Asp | Gly | Lys | Val | Ala | Ala | Ile |
| | | | 20 | | | | | 25 | | | | | 30 | | |

| | | | | | | | | | | | | | | |
|---|---|---|---|---|---|---|---|---|---|---|---|---|---|---|
| Ser | Ser | Asp | Thr | Ser | Asp | Val | Glu | Ala | Ser | Arg | Thr | Ile | Asp | Ala | Gly |
| | | | 35 | | | | | 40 | | | | | 45 | | |

| | | | | | | | | | | | | | | |
|---|---|---|---|---|---|---|---|---|---|---|---|---|---|---|
| Gly | Lys | Phe | Val | Met | Pro | Gly | Val | Val | Asp | Glu | His | Val | His | Ile | Ile |
| | 50 | | | | | 55 | | | | | 60 | | | | |

| | | | | | | | | | | | | | | |
|---|---|---|---|---|---|---|---|---|---|---|---|---|---|---|
| Asp | Met | Asp | Leu | Lys | Asn | Arg | Tyr | Gly | Arg | Phe | Glu | Leu | Asp | Ser | Glu |
| 65 | | | | | 70 | | | | | 75 | | | | | 80 |

| | | | | | | | | | | | | | | |
|---|---|---|---|---|---|---|---|---|---|---|---|---|---|---|
| Ser | Ala | Ala | Val | Gly | Gly | Ile | Thr | Thr | Ile | Ile | Glu | Met | Pro | Ile | Thr |
| | | | | 85 | | | | | 90 | | | | | 95 | |

| | | | | | | | | | | | | | | |
|---|---|---|---|---|---|---|---|---|---|---|---|---|---|---|
| Phe | Pro | Pro | Thr | Thr | Thr | Leu | Asp | Ala | Phe | Leu | Glu | Lys | Lys | Lys | Gln |
| | | | 100 | | | | | 105 | | | | | 110 | | |

| | | | | | | | | | | | | | | |
|---|---|---|---|---|---|---|---|---|---|---|---|---|---|---|
| Ala | Gly | Gln | Arg | Leu | Lys | Val | Asp | Phe | Ala | Leu | Tyr | Gly | Gly | Gly | Val |
| | | | 115 | | | | | 120 | | | | | 125 | | |

| | | | | | | | | | | | | | | |
|---|---|---|---|---|---|---|---|---|---|---|---|---|---|---|
| Pro | Gly | Asn | Leu | Pro | Glu | Ile | Arg | Lys | Met | His | Asp | Ala | Gly | Ala | Val |
| | 130 | | | | | 135 | | | | | 140 | | | | |

| | | | | | | | | | | | | | | |
|---|---|---|---|---|---|---|---|---|---|---|---|---|---|---|
| Gly | Phe | Lys | Ser | Met | Met | Ala | Thr | Ser | Val | Pro | Gly | Met | Phe | Asp | Ala |
| 145 | | | | | 150 | | | | | 155 | | | | | 160 |

| | | | | | | | | | | | | | | |
|---|---|---|---|---|---|---|---|---|---|---|---|---|---|---|
| Val | Ser | Asp | Gly | Glu | Leu | Phe | Glu | Ile | Phe | Gln | Glu | Ile | Ala | Ala | Cys |
| | | | | 165 | | | | | 170 | | | | | 175 | |

| | | | | | | | | | | | | | | |
|---|---|---|---|---|---|---|---|---|---|---|---|---|---|---|
| Gly | Ser | Val | Val | Val | Val | His | Ala | Glu | Asn | Glu | Thr | Ile | Ile | Gln | Ala |
| | | | 180 | | | | | 185 | | | | | 190 | | |

| | | | | | | | | | | | | | | |
|---|---|---|---|---|---|---|---|---|---|---|---|---|---|---|
| Leu | Gln | Lys | Gln | Ile | Lys | Ala | Ala | Gly | Arg | Lys | Asp | Met | Ala | Ala | Tyr |
| | | | 195 | | | | | 200 | | | | | 205 | | |

| | | | | | | | | | | | | | | |
|---|---|---|---|---|---|---|---|---|---|---|---|---|---|---|
| Glu | Ala | Ser | Gln | Pro | Val | Phe | Gln | Glu | Asn | Glu | Ala | Ile | Gln | Arg | Ala |
| | 210 | | | | | 215 | | | | | 220 | | | | |

| | | | | | | | | | | | | | | |
|---|---|---|---|---|---|---|---|---|---|---|---|---|---|---|
| Leu | Leu | Leu | Gln | Lys | Glu | Ala | Gly | Cys | Arg | Leu | Ile | Val | Leu | His | Val |
| 225 | | | | | 230 | | | | | 235 | | | | | 240 |

| | | | | | | | | | | | | | | |
|---|---|---|---|---|---|---|---|---|---|---|---|---|---|---|
| Ser | Asn | Pro | Asp | Gly | Val | Glu | Leu | Ile | His | Gln | Ala | Gln | Ser | Glu | Gly |
| | | | | 245 | | | | | 250 | | | | | 255 | |

| | | | | | | | | | | | | | | |
|---|---|---|---|---|---|---|---|---|---|---|---|---|---|---|
| Gln | Asp | Val | His | Cys | Glu | Ser | Gly | Pro | Gln | Tyr | Leu | Asn | Ile | Thr | Thr |
| | | | 260 | | | | | 265 | | | | | 270 | | |

| | | | | | | | | | | | | | | |
|---|---|---|---|---|---|---|---|---|---|---|---|---|---|---|
| Asp | Asp | Ala | Glu | Arg | Ile | Gly | Pro | Tyr | Met | Lys | Val | Ala | Pro | Pro | Val |
| | | | 275 | | | | | 280 | | | | | 285 | | |

| | | | | | | | | | | | | | | |
|---|---|---|---|---|---|---|---|---|---|---|---|---|---|---|
| Arg | Ser | Ala | Glu | Met | Asn | Val | Arg | Leu | Trp | Glu | Gln | Leu | Glu | Asn | Gly |
| | 290 | | | | | 295 | | | | | 300 | | | | |

| | | | | | | | | | | | | | | |
|---|---|---|---|---|---|---|---|---|---|---|---|---|---|---|
| Leu | Ile | Asp | Thr | Leu | Gly | Ser | Asp | His | Gly | Gly | His | Pro | Val | Glu | Asp |
| 305 | | | | | 310 | | | | | 315 | | | | | 320 |

| | | | | | | | | | | | | | | |
|---|---|---|---|---|---|---|---|---|---|---|---|---|---|---|
| Lys | Glu | Pro | Gly | Trp | Lys | Asp | Val | Trp | Lys | Ala | Gly | Asn | Gly | Ala | Leu |
| | | | | 325 | | | | | 330 | | | | | 335 | |

| | | | | | | | | | | | | | | |
|---|---|---|---|---|---|---|---|---|---|---|---|---|---|---|
| Gly | Leu | Glu | Thr | Ser | Leu | Pro | Met | Met | Leu | Thr | Asn | Gly | Val | Asn | Lys |
| | | | 340 | | | | | 345 | | | | | 350 | | |

| | | | | | | | | | | | | | | |
|---|---|---|---|---|---|---|---|---|---|---|---|---|---|---|
| Gly | Arg | Leu | Ser | Leu | Glu | Arg | Leu | Val | Glu | Val | Met | Cys | Glu | Lys | Pro |
| | | | 355 | | | | | 360 | | | | | 365 | | |

```
Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 10
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (152)..(152)
<223> OTHER INFORMATION: A replaced by V

<400> SEQUENCE: 10

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Val Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Gly Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
```

-continued

```
                245                 250                 255
Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 11
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (152)..(152)
<223> OTHER INFORMATION: A replaced by S
<220> FEATURE:
<221> NAME/KEY: VARIANT
<222> LOCATION: (154)..(154)
<223> OTHER INFORMATION: V replaced by I

<400> SEQUENCE: 11

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110
```

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
130                 135                 140

Gly Phe Lys Ser Met Met Ala Ser Ser Ile Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Gly Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 12
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (152)..(152)
<223> OTHER INFORMATION: A replaced by V
<220> FEATURE:

<221> NAME/KEY: VARIANT
<222> LOCATION: (154)..(154)
<223> OTHER INFORMATION: V replaced by C

<400> SEQUENCE: 12

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Val Ser Cys Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
```

```
                385                 390                 395                 400
Asp Ala Ser Gln Phe Arg Ser Leu His Lys Tyr Ser Pro Phe Asp Gly
                    405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455

<210> SEQ ID NO 13
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (152)..(152)
<223> OTHER INFORMATION: A replaced by C
<220> FEATURE:
<221> NAME/KEY: VARIANT
<222> LOCATION: (154)..(154)
<223> OTHER INFORMATION: V replaced by S

<400> SEQUENCE: 13

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Cys Ser Ser Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255
```

-continued

```
Gln Asp Val His Cys Glu Ser Gly Pro Gln Tyr Leu Asn Ile Thr Thr
        260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
        290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
        340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
        405                 410                 415

Met Pro Val Thr Gly Ala Pro Val Leu Thr Met Val Arg Gly Thr Val
        420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
        450                 455
```

<210> SEQ ID NO 14
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (71)..(71)
<223> OTHER INFORMATION: R replaced by D
<220> FEATURE:
<221> NAME/KEY: VARIANT
<222> LOCATION: (72)..(72)
<223> OTHER INFORMATION: Y replaced by H
<220> FEATURE:
<221> NAME/KEY: VARIANT
<222> LOCATION: (152)..(152)
<223> OTHER INFORMATION: A replaced by S

<400> SEQUENCE: 14

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
            85                  90                  95
```

```
Phe Pro Pro Thr Thr Thr Leu Asp Ala Phe Leu Glu Lys Lys Lys Gln
                100                 105                 110
Ala Gly Gln Arg Leu Lys Val Asp Phe Ala Leu Tyr Gly Gly Gly Val
            115                 120                 125
Pro Gly Asn Leu Pro Glu Ile Arg Lys Met His Asp Ala Gly Ala Val
        130                 135                 140
Gly Phe Lys Ser Met Met Ala Ser Ser Val Pro Gly Met Phe Asp Ala
145                 150                 155                 160
Val Ser Asp Gly Glu Leu Phe Glu Ile Phe Gln Glu Ile Ala Ala Cys
                165                 170                 175
Gly Ser Val Val Val His Ala Glu Asn Glu Thr Ile Ile Gln Ala
            180                 185                 190
Leu Gln Lys Gln Ile Lys Ala Ala Gly Arg Lys Asp Met Ala Ala Tyr
        195                 200                 205
Glu Ala Ser Gln Pro Val Phe Gln Glu Asn Glu Ala Ile Gln Arg Ala
    210                 215                 220
Leu Leu Leu Gln Lys Glu Ala Gly Cys Arg Leu Ile Val Leu His Val
225                 230                 235                 240
Ser Asn Pro Asp Gly Val Glu Leu Ile His Gln Ala Gln Ser Glu Gly
                245                 250                 255
Gln Asp Val His Cys Glu Ser Gly Pro Gln Tyr Leu Asn Ile Thr Thr
            260                 265                 270
Asp Asp Ala Glu Arg Ile Gly Pro Tyr Met Lys Val Ala Pro Pro Val
        275                 280                 285
Arg Ser Ala Glu Met Asn Val Arg Leu Trp Glu Gln Leu Glu Asn Gly
    290                 295                 300
Leu Ile Asp Thr Leu Gly Ser Asp His Gly Gly His Pro Val Glu Asp
305                 310                 315                 320
Lys Glu Pro Gly Trp Lys Asp Val Trp Lys Ala Gly Asn Gly Ala Leu
                325                 330                 335
Gly Leu Glu Thr Ser Leu Pro Met Met Leu Thr Asn Gly Val Asn Lys
            340                 345                 350
Gly Arg Leu Ser Leu Glu Arg Leu Val Glu Val Met Cys Glu Lys Pro
        355                 360                 365
Ala Lys Leu Phe Gly Ile Tyr Pro Gln Lys Gly Thr Leu Gln Val Gly
    370                 375                 380
Ser Asp Ala Asp Leu Leu Ile Leu Asp Leu Asp Ile Asp Thr Lys Val
385                 390                 395                 400
Asp Ala Ser Gln Phe Arg Ser Leu His Lys Tyr Ser Pro Phe Asp Gly
                405                 410                 415
Met Pro Val Thr Gly Ala Pro Val Leu Thr Met Val Arg Gly Thr Val
            420                 425                 430
Val Ala Glu Lys Gly Glu Val Leu Val Glu Gln Gly Phe Gly Gln Phe
        435                 440                 445
Val Thr Arg His Asp Tyr Glu Ala Ser Lys
    450                 455

<210> SEQ ID NO 15
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
```

```
<222> LOCATION: (71)..(71)
<223> OTHER INFORMATION: R replaced by D
<220> FEATURE:
<221> NAME/KEY: VARIANT
<222> LOCATION: (72)..(72)
<223> OTHER INFORMATION: Y replaced by N
<220> FEATURE:
<221> NAME/KEY: VARIANT
<222> LOCATION: (152)..(152)
<223> OTHER INFORMATION: A replaced by S

<400> SEQUENCE: 15
```

| Met<br>1 | Phe | Asp | Val | Ile<br>5 | Val | Lys | Asn | Cys | Arg<br>10 | Met | Val | Ser | Ser | Asp<br>15 | Gly |
|---|---|---|---|---|---|---|---|---|---|---|---|---|---|---|---|
| Ile | Thr | Glu<br>20 | Ala | Asp | Ile | Leu | Val<br>25 | Lys | Asp | Gly | Lys | Val<br>30 | Ala | Ala | Ile |
| Ser | Ser<br>35 | Asp | Thr | Ser | Asp<br>40 | Val | Glu | Ala | Ser | Arg<br>45 | Thr | Ile | Asp | Ala | Gly |
| Gly<br>50 | Lys | Phe | Val | Met | Pro<br>55 | Val | Val | Asp | Glu | His<br>60 | Val | His | Ile | Ile |
| Asp<br>65 | Met | Asp | Leu | Lys | Asn<br>70 | Asp | Asn | Gly | Arg | Phe<br>75 | Glu | Leu | Asp | Ser | Glu<br>80 |
| Ser | Ala | Ala | Val | Gly<br>85 | Gly | Ile | Thr | Thr | Ile<br>90 | Ile | Glu | Met | Pro | Ile<br>95 | Thr |
| Phe | Pro | Pro | Thr<br>100 | Thr | Thr | Leu | Asp | Ala<br>105 | Phe | Leu | Glu | Lys | Lys<br>110 | Lys | Gln |
| Ala | Gly | Gln<br>115 | Arg | Leu | Lys | Val | Asp<br>120 | Phe | Ala | Leu | Tyr | Gly<br>125 | Gly | Gly | Val |
| Pro | Gly<br>130 | Asn | Leu | Pro | Glu | Ile<br>135 | Arg | Lys | Met | His | Asp<br>140 | Ala | Gly | Ala | Val |
| Gly<br>145 | Phe | Lys | Ser | Met | Met<br>150 | Ala | Ser | Ser | Val | Pro<br>155 | Gly | Met | Phe | Asp | Ala<br>160 |
| Val | Ser | Asp | Gly | Glu<br>165 | Leu | Phe | Glu | Ile | Phe<br>170 | Gln | Glu | Ile | Ala | Ala<br>175 | Cys |
| Gly | Ser | Val | Val<br>180 | Val | Val | His | Ala | Glu<br>185 | Asn | Glu | Thr | Ile | Ile<br>190 | Gln | Ala |
| Leu | Gln | Lys<br>195 | Gln | Ile | Lys | Ala | Ala<br>200 | Gly | Arg | Lys | Asp | Met<br>205 | Ala | Ala | Tyr |
| Glu | Ala<br>210 | Ser | Gln | Pro | Val | Phe<br>215 | Gln | Glu | Asn | Glu | Ala<br>220 | Ile | Gln | Arg | Ala |
| Leu<br>225 | Leu | Leu | Gln | Lys | Glu<br>230 | Ala | Gly | Cys | Arg | Leu<br>235 | Ile | Val | Leu | His | Val<br>240 |
| Ser | Asn | Pro | Asp | Gly<br>245 | Val | Glu | Leu | Ile | His<br>250 | Gln | Ala | Gln | Ser | Glu<br>255 | Gly |
| Gln | Asp | Val | His<br>260 | Cys | Glu | Ser | Gly | Pro<br>265 | Gln | Tyr | Leu | Asn | Ile<br>270 | Thr | Thr |
| Asp | Asp<br>275 | Ala | Glu | Arg | Ile | Gly<br>280 | Pro | Tyr | Met | Lys | Val<br>285 | Ala | Pro | Pro | Val |
| Arg | Ser<br>290 | Ala | Glu | Met | Asn<br>295 | Val | Arg | Leu | Trp | Glu<br>300 | Gln | Leu | Glu | Asn | Gly |
| Leu<br>305 | Ile | Asp | Thr | Leu | Gly<br>310 | Ser | Asp | His | Gly | His<br>315 | Pro | Val | Glu | Asp | Lys<br>320 |
| Lys | Glu | Pro | Gly | Trp<br>325 | Lys | Asp | Val | Trp | Lys<br>330 | Ala | Gly | Asn | Gly | Ala<br>335 | Leu |
| Gly | Leu | Glu | Thr<br>340 | Ser | Leu | Pro | Met | Met<br>345 | Leu | Thr | Asn | Gly | Val<br>350 | Asn | Lys |

```
Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 16
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (71)..(71)
<223> OTHER INFORMATION: R replaced by V
<220> FEATURE:
<221> NAME/KEY: VARIANT
<222> LOCATION: (72)..(72)
<223> OTHER INFORMATION: Y replaced by N
<220> FEATURE:
<221> NAME/KEY: VARIANT
<222> LOCATION: (152)..(152)
<223> OTHER INFORMATION: A replaced by S

<400> SEQUENCE: 16

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Val Asn Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190
```

Leu Gln Lys Gln Ile Lys Ala Gly Arg Lys Asp Met Ala Ala Tyr
            195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 17
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (71)..(71)
<223> OTHER INFORMATION: R replaced by S
<220> FEATURE:
<221> NAME/KEY: VARIANT
<222> LOCATION: (72)..(72)
<223> OTHER INFORMATION: Y replaced by N
<220> FEATURE:
<221> NAME/KEY: VARIANT
<222> LOCATION: (152)..(152)
<223> OTHER INFORMATION: A replaced by C
<220> FEATURE:
<221> NAME/KEY: VARIANT
<222> LOCATION: (154)..(154)
<223> OTHER INFORMATION: V replaced by S
<220> FEATURE:
<221> NAME/KEY: VARIANT
<222> LOCATION: (181)..(181)
<223> OTHER INFORMATION: V replaced by A

```
<400> SEQUENCE: 17

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Ser Asn Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Cys Ser Ser Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Ala Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415
```

```
Met Pro Val Thr Gly Ala Pro Val Leu Thr Met Val Arg Gly Thr Val
        420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
        450                 455

<210> SEQ ID NO 18
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (71)..(71)
<223> OTHER INFORMATION: R replaced by Y
<220> FEATURE:
<221> NAME/KEY: VARIANT
<222> LOCATION: (72)..(72)
<223> OTHER INFORMATION: Y replaced by N
<220> FEATURE:
<221> NAME/KEY: VARIANT
<222> LOCATION: (152)..(152)
<223> OTHER INFORMATION: A replaced by S

<400> SEQUENCE: 18

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Tyr Asn Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255
```

```
Gln Asp Val His Cys Glu Ser Gly Pro Gln Tyr Leu Asn Ile Thr Thr
        260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
        290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
        340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
        450                 455

<210> SEQ ID NO 19
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
<222> LOCATION: (71)..(71)
<223> OTHER INFORMATION: R replaced by L
<220> FEATURE:
<221> NAME/KEY: VARIANT
<222> LOCATION: (152)..(152)
<223> OTHER INFORMATION: A replaced by C
<220> FEATURE:
<221> NAME/KEY: VARIANT
<222> LOCATION: (154)..(154)
<223> OTHER INFORMATION: V replaced by S

<400> SEQUENCE: 19

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Leu Tyr Gly Arg Phe Glu Leu Asp Ser Glu
65                  70                  75                  80

Ser Ala Ala Val Gly Gly Ile Thr Ile Ile Glu Met Pro Ile Thr
            85                  90                  95
```

```
Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Cys Ser Ser Pro Gly Met Phe Asp Ala
145                 150                 155                 160

Val Ser Asp Gly Glu Leu Phe Glu Ile Phe Gln Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Gly Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 20
<211> LENGTH: 458
<212> TYPE: PRT
<213> ORGANISM: Artificial
<220> FEATURE:
<223> OTHER INFORMATION: mutant sequence
<220> FEATURE:
<221> NAME/KEY: VARIANT
```

```
<222> LOCATION: (71)..(71)
<223> OTHER INFORMATION: R replaced by Y
<220> FEATURE:
<221> NAME/KEY: VARIANT
<222> LOCATION: (72)..(72)
<223> OTHER INFORMATION: Y replaced by H
<220> FEATURE:
<221> NAME/KEY: VARIANT
<222> LOCATION: (152)..(152)
<223> OTHER INFORMATION: A replaced by S

<400> SEQUENCE: 20
```

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
                35                  40                  45

Gly Lys Phe Val Met Pro Gly Val Val Asp Glu His Val His Ile Ile
        50                  55                  60

Asp Met Asp Leu Lys Asn Tyr His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

```
Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 21
<211> LENGTH: 31
<212> TYPE: DNA
<213> ORGANISM: Artificial
<220> FEATURE:
<223> OTHER INFORMATION: synthetic peptide
<220> FEATURE:
<221> NAME/KEY: misc_feature
<222> LOCATION: (15)..(16)
<223> OTHER INFORMATION: n is a, c, g, or t

<400> SEQUENCE: 21
atctgaagaa ccggnnkggc cgcttcgaac t                              31

<210> SEQ ID NO 22
<211> LENGTH: 31
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (16)..(17)
<223> OTHER INFORMATION: n is a, c, g, or t

<400> SEQUENCE: 22
agttcgaagc ggccmnnccg gttcttcaga t                              31

<210> SEQ ID NO 23
<211> LENGTH: 30
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (14)..(15)
<223> OTHER INFORMATION: n is a, c, g, or t

<400> SEQUENCE: 23
catcgagatg ccgnnkacct tcccgcccac                                30

<210> SEQ ID NO 24
<211> LENGTH: 30
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (16)..(17)
```

```
<223> OTHER INFORMATION: n is a, c, g, or t

<400> SEQUENCE: 24
gtgggcggga aggtmnncgg catctcgatg                                           30

<210> SEQ ID NO 25
<211> LENGTH: 30
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 25
tgatggcagc ctcannkccg ggcatgttcg                                           30

<210> SEQ ID NO 26
<211> LENGTH: 30
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 26
cgaacatgcc cggmnntgag gctgccatca                                           30

<210> SEQ ID NO 27
<211> LENGTH: 30
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 27
tggcagcctc agttnnkggc atgttcgacg                                           30

<210> SEQ ID NO 28
<211> LENGTH: 31
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (16)..(17)
<223> OTHER INFORMATION: n is a, c, g, or t

<400> SEQUENCE: 28
gcgtcgaaca tgccmnnaac tgaggctgcc a                                         31

<210> SEQ ID NO 29
<211> LENGTH: 31
<212> TYPE: DNA
<213> ORGANISM: Artificial
<220> FEATURE:
<223> OTHER INFORMATION: synthetic DNA
<220> FEATURE:
<221> NAME/KEY: misc_feature
```

<222> LOCATION: (15)..(16)
<223> OTHER INFORMATION: n is a, c, g, or t

<400> SEQUENCE: 29
cagcctcagt tccgnnkcag cctcagttcc g                                31

<210> SEQ ID NO 30
<211> LENGTH: 31
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (16)..(17)
<223> OTHER INFORMATION: n is a, c, g, or t

<400> SEQUENCE: 30
cggaactgag gctgmnncgg aactgaggct g                                31

<210> SEQ ID NO 31
<211> LENGTH: 30
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 31
cccttgggtc agacnnkggc ggacatcctg                                  30

<210> SEQ ID NO 32
<211> LENGTH: 30
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 32
caggatgtcc gccmnngtct gacccaaggg                                  30

<210> SEQ ID NO 33
<211> LENGTH: 32
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 33
cgtatatgaa ggtcnnkccg cccgtccgct ca                               32

<210> SEQ ID NO 34
<211> LENGTH: 32
<212> TYPE: DNA
<213> ORGANISM: Artificial
<220> FEATURE:
<223> OTHER INFORMATION: synthetic DNA
<220> FEATURE:

```
<221> NAME/KEY: misc_feature
<222> LOCATION: (17)..(18)
<223> OTHER INFORMATION: n is a, c, g, or t

<400> SEQUENCE: 34
tgagcggacg ggcggmnnga ccttcatata cg                              32

<210> SEQ ID NO 35
<211> LENGTH: 29
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 35
gaccgtatat gaagnnkgcg ccgcccgtc                                  29

<210> SEQ ID NO 36
<211> LENGTH: 29
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (14)..(15)
<223> OTHER INFORMATION: n is a, c, g, or t

<400> SEQUENCE: 36
gacgggcggc gcmnncttca tatacggtc                                  29

<210> SEQ ID NO 37
<211> LENGTH: 31
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (17)..(18)
<223> OTHER INFORMATION: n is a, c, g, or t

<400> SEQUENCE: 37
caccatcatc gagatgnnka taaccttccc g                               31

<210> SEQ ID NO 38
<211> LENGTH: 31
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (14)..(15)
<223> OTHER INFORMATION: n is a, c, g, or t

<400> SEQUENCE: 38
cgggaaggtt atmnncatct cgatgatggt g                               31

<210> SEQ ID NO 39
<211> LENGTH: 33
<212> TYPE: DNA
<213> ORGANISM: Artificial
<220> FEATURE:
<223> OTHER INFORMATION: synthetic DNA
```

```
<220> FEATURE:
<221> NAME/KEY: misc_feature
<222> LOCATION: (15)..(16)
<223> OTHER INFORMATION: n is a, c, g, or t

<400> SEQUENCE: 39
tgccgataac cttcnnkccc accaccactt tgg                              33

<210> SEQ ID NO 40
<211> LENGTH: 33
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (18)..(19)
<223> OTHER INFORMATION: n is a, c, g, or t

<400> SEQUENCE: 40
ccaaagtggt ggtgggmnng aaggttatcg gca                              33

<210> SEQ ID NO 41
<211> LENGTH: 32
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 41
cgataacctt cccgnnkacc accactttgg ac                               32

<210> SEQ ID NO 42
<211> LENGTH: 32
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (17)..(18)
<223> OTHER INFORMATION: n is a, c, g, or t

<400> SEQUENCE: 42
gtccaaagtg gtggtmnncg ggaaggttat cg                               32

<210> SEQ ID NO 43
<211> LENGTH: 32
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (14)..(15)
<223> OTHER INFORMATION: n is a, c, g, or t

<400> SEQUENCE: 43
ggatctgaag aacnnktatg gccgcttcga ac                               32

<210> SEQ ID NO 44
<211> LENGTH: 32
<212> TYPE: DNA
<213> ORGANISM: Artificial
<220> FEATURE:
```

<223> OTHER INFORMATION: synthetic DNA
<220> FEATURE:
<221> NAME/KEY: misc_feature
<222> LOCATION: (18)..(19)
<223> OTHER INFORMATION: n is a, c, g, or t

<400> SEQUENCE: 44
gttcgaagcg gccatamnng ttcttcagat cc                                    32

<210> SEQ ID NO 45
<211> LENGTH: 31
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (17)..(18)
<223> OTHER INFORMATION: n is a, c, g, or t

<400> SEQUENCE: 45
caagtcaatg atggcannkt cagttccggg c                                     31

<210> SEQ ID NO 46
<211> LENGTH: 31
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (14)..(15)
<223> OTHER INFORMATION: n is a, c, g, or t

<400> SEQUENCE: 46
gcccggaact gamnntgcca tcattgactt g                                     31

<210> SEQ ID NO 47
<211> LENGTH: 32
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 47
cagttccggg catgnnkgac gccgtcagcg ac                                    32

<210> SEQ ID NO 48
<211> LENGTH: 32
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (17)..(18)
<223> OTHER INFORMATION: n is a, c, g, or t

<400> SEQUENCE: 48
gtcgctgacg gcgtcmnnca tgcccggaac tg                                    32

<210> SEQ ID NO 49
<211> LENGTH: 37
<212> TYPE: DNA
<213> ORGANISM: Artificial

```
<220> FEATURE:
<223> OTHER INFORMATION: synthetic DNA
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 49
catggatctg aagaacndtn dtggccgctt cgaactc                              37

<210> SEQ ID NO 50
<211> LENGTH: 37
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 50
gagttcgaag cggccahnah ngttcttcag atccatg                              37

<210> SEQ ID NO 51
<211> LENGTH: 44
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 51
gcttcaagtc aatgatggca ndttcandtc cgggcatgtt cgac                      44

<210> SEQ ID NO 52
<211> LENGTH: 44
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 52
gtcgaacatg cccggahntg aahntgccat cattgacttg aagc                      44

<210> SEQ ID NO 53
<211> LENGTH: 35
<212> TYPE: DNA
```

```
<213> ORGANISM: Artificial
<220> FEATURE:
<223> OTHER INFORMATION: synthetic DNA
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 53
ggaccgtata tgaagndtnd tccgcccgtc cgctc                              35

<210> SEQ ID NO 54
<211> LENGTH: 35
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 54
gagcggacgg gcggahnahn cttcatatac ggtcc                              35

<210> SEQ ID NO 55
<211> LENGTH: 33
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (16)..(17)
<223> OTHER INFORMATION: n is a, c, g, or t

<400> SEQUENCE: 55
gaacatgtgc atatcnnkga catggatctg aag                                33

<210> SEQ ID NO 56
<211> LENGTH: 33
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (17)..(18)
<223> OTHER INFORMATION: n is a, c, g, or t

<400> SEQUENCE: 56
cttcagatcc atgtcmnnga tatgcacatg ttc                                33

<210> SEQ ID NO 57
<211> LENGTH: 22
<212> TYPE: DNA
<213> ORGANISM: Artificial
<220> FEATURE:
<223> OTHER INFORMATION: synthetic DNA

<400> SEQUENCE: 57
tcacttcgac gcctcgtagt cg                                            22
```

<210> SEQ ID NO 58
<211> LENGTH: 29
<212> TYPE: DNA
<213> ORGANISM: Artificial
<220> FEATURE:
<223> OTHER INFORMATION: synthetic DNA

<400> SEQUENCE: 58
atgtttgacg taatagttaa gaactgccg                              29

<210> SEQ ID NO 59
<211> LENGTH: 42
<212> TYPE: DNA
<213> ORGANISM: Artificial
<220> FEATURE:
<223> OTHER INFORMATION: synthetic DNA

<400> SEQUENCE: 59
gtgtgatggc gtgaggcagc ctactgccgc caggcaaatt ct              42

<210> SEQ ID NO 60
<211> LENGTH: 40
<212> TYPE: DNA
<213> ORGANISM: Artificial
<220> FEATURE:
<223> OTHER INFORMATION: synthetic DNA

<400> SEQUENCE: 60
cacactaccg cactccgtcg cgtcagccac agcactacgg                  40

<210> SEQ ID NO 61
<211> LENGTH: 30
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (13)..(14)
<223> OTHER INFORMATION: n is a, c, g, or t

<400> SEQUENCE: 61
cgtatggtgt ccnnkgacgg aatcaccgag                             30

<210> SEQ ID NO 62
<211> LENGTH: 31
<212> TYPE: DNA
<213> ORGANISM: Artificial
<220> FEATURE:
<223> OTHER INFORMATION: synthetic DNA

<400> SEQUENCE: 62
ggacaccata cggcagttct taactattac g                           31

<210> SEQ ID NO 63
<211> LENGTH: 29
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (13)..(14)
<223> OTHER INFORMATION: n is a, c, g, or t

<400> SEQUENCE: 63
agctcggaca cannkgatgt tgaggcgag    29

<210> SEQ ID NO 64
<211> LENGTH: 22
<212> TYPE: DNA
<213> ORGANISM: Artificial
<220> FEATURE:
<223> OTHER INFORMATION: synthetic DNA

<400> SEQUENCE: 64
tgtgtccgag ctgattgcgg cg    22

<210> SEQ ID NO 65
<211> LENGTH: 38
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 65
gtcaatgatg gcaagtndtd nyccgggcat gttcgacg    38

<210> SEQ ID NO 66
<211> LENGTH: 38
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 66
cgtcgaacat gcccggrnha hnacttgcca tcattgac    38

<210> SEQ ID NO 67
<211> LENGTH: 32
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (17)..(18)
<223> OTHER INFORMATION: n is a, c, g, or t

<400> SEQUENCE: 67
ccgtatggtg tccbbtnnkg gaatcaccga gg    32

<210> SEQ ID NO 68
<211> LENGTH: 32
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (15)..(16)
<223> OTHER INFORMATION: n is a, c, g, or t

<400> SEQUENCE: 68
cctcggtgat tccmnnavvg gacaccatac gg                                32

<210> SEQ ID NO 69
<211> LENGTH: 34
<212> TYPE: DNA
<213> ORGANISM: Artificial
<220> FEATURE:
<223> OTHER INFORMATION: synthetic DNA

<400> SEQUENCE: 69
gaacatgtgc atatcatcga catggatctg aaga                              34

<210> SEQ ID NO 70
<211> LENGTH: 34
<212> TYPE: DNA
<213> ORGANISM: Artificial
<220> FEATURE:
<223> OTHER INFORMATION: synthetic DNA

<400> SEQUENCE: 70
tcttcagatc catgtcgatg atatgcacat gttc                              34

<210> SEQ ID NO 71
<211> LENGTH: 34
<212> TYPE: DNA
<213> ORGANISM: Artificial
<220> FEATURE:
<223> OTHER INFORMATION: synthetic DNA

<400> SEQUENCE: 71
caagtcaatg atggcagcct cagttccggg catg                              34

<210> SEQ ID NO 72
<211> LENGTH: 34
<212> TYPE: DNA
<213> ORGANISM: Artificial
<220> FEATURE:
<223> OTHER INFORMATION: synthetic DNA

<400> SEQUENCE: 72
catgcccgga actgaggctg ccatcattga cttg                              34

<210> SEQ ID NO 73
<211> LENGTH: 458
<212> TYPE: PRT
<213> ORGANISM: Artificial
<220> FEATURE:
<223> OTHER INFORMATION: mutant sequence

<400> SEQUENCE: 73

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
                20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Ile
        50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro His Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 74
<211> LENGTH: 458
<212> TYPE: PRT
<213> ORGANISM: Artificial
<220> FEATURE:

<223> OTHER INFORMATION: mutant sequence

<400> SEQUENCE: 74

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
        130                 135                 140

Gly Phe Lys Ser Met Met Ala Ala Ser Gly Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
            290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
            325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400
```

```
Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455
```

<210> SEQ ID NO 75
<211> LENGTH: 458
<212> TYPE: PRT
<213> ORGANISM: Artificial
<220> FEATURE:
<223> OTHER INFORMATION: mutant sequence

<400> SEQUENCE: 75

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Asp Glu His Val His Ile Ile
    50                  55                  60

Asp Met Asp Leu Lys Asn Arg Tyr Gly Arg Phe Glu Leu Asp Ser Glu
65              70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Asn Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300
```

```
Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
            325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Val Leu Val Glu Gln Gly Phe Gly Gln Phe
                435                 440                 445

Val Thr Arg His Asp Tyr Glu Ala Ser Lys
                450                 455

<210> SEQ ID NO 76
<211> LENGTH: 458
<212> TYPE: PRT
<213> ORGANISM: Artificial
<220> FEATURE:
<223> OTHER INFORMATION: mutant sequence

<400> SEQUENCE: 76

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Asp Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
        180                 185                 190

Leu Gln Lys Gln Ile Lys Ala Ala Gly Arg Lys Asp Met Ala Ala Tyr
    195                 200                 205
```

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
    355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
    435                 440                 445

Val Thr Arg His Asp Tyr Glu Ala Ser Lys
            450                 455

<210> SEQ ID NO 77
<211> LENGTH: 458
<212> TYPE: PRT
<213> ORGANISM: Artificial
<220> FEATURE:
<223> OTHER INFORMATION: mutant sequence

<400> SEQUENCE: 77

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Glu Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Ile Ala Ala Cys
            165                 170                 175

Gly Ser Val Val Val His Ala Glu Asn Glu Thr Ile Ile Gln Ala
        180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 78
<211> LENGTH: 458
<212> TYPE: PRT
<213> ORGANISM: Artificial
<220> FEATURE:
<223> OTHER INFORMATION: mutant sequence

<400> SEQUENCE: 78

Met Phe Asp Val Ile Val Lys Asn Cys Arg Met Val Ser Ser Asp Gly
1               5                   10                  15

```
Ile Thr Glu Ala Asp Ile Leu Val Lys Asp Gly Lys Val Ala Ala Ile
         20                  25                  30

Ser Ser Asp Thr Ser Asp Val Glu Ala Ser Arg Thr Ile Asp Ala Gly
     35                  40                  45

Gly Lys Phe Val Met Pro Gly Val Val Asp Glu His Val His Ile Ile
     50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
             85                  90                  95

Phe Pro Pro Thr Thr Thr Leu Asp Ala Phe Leu Glu Lys Lys Lys Gln
             100                 105                 110

Ala Gly Gln Arg Leu Lys Val Asp Phe Ala Leu Tyr Gly Gly Gly Val
         115                 120                 125

Pro Gly Asn Leu Pro Glu Ile Arg Lys Met His Asp Ala Gly Ala Val
         130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
             165                 170                 175

Gly Ser Val Val Val His Ala Glu Asn Glu Thr Ile Ile Gln Ala
             180                 185                 190

Leu Gln Lys Gln Ile Lys Ala Ala Gly Arg Lys Asp Met Ala Ala Tyr
         195                 200                 205

Glu Ala Ser Gln Pro Val Phe Gln Glu Asn Glu Ala Ile Gln Arg Ala
     210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
             245                 250                 255

Gln Asp Val His Cys Glu Ser Gly Pro Gln Tyr Leu Asn Ile Thr Thr
             260                 265                 270

Asp Asp Ala Glu Arg Ile Gly Pro Tyr Met Lys Phe Ala Pro Pro Val
         275                 280                 285

Arg Ser Ala Glu Met Asn Val Arg Leu Trp Glu Gln Leu Glu Asn Gly
290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
             325                 330                 335

Gly Leu Glu Thr Ser Leu Pro Met Met Leu Thr Asn Gly Val Asn Lys
             340                 345                 350

Gly Arg Leu Ser Leu Glu Arg Leu Val Glu Val Met Cys Glu Lys Pro
         355                 360                 365

Ala Lys Leu Phe Gly Ile Tyr Pro Gln Lys Gly Thr Leu Gln Val Gly
         370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                 405                 410                 415

Met Pro Val Thr Gly Ala Pro Val Leu Thr Met Val Arg Gly Thr Val
             420                 425                 430

Val Ala Glu Lys Gly Glu Val Leu Val Glu Gln Gly Phe Gly Gln Phe
```

```
            435                 440                 445
Val Thr Arg His Asp Tyr Glu Ala Ser Lys
    450                 455

<210> SEQ ID NO 79
<211> LENGTH: 458
<212> TYPE: PRT
<213> ORGANISM: Artificial
<220> FEATURE:
<223> OTHER INFORMATION: mutant sequence

<400> SEQUENCE: 79

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Ala Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
```

```
            340             345             350
Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455

<210> SEQ ID NO 80
<211> LENGTH: 458
<212> TYPE: PRT
<213> ORGANISM: Artificial
<220> FEATURE:
<223> OTHER INFORMATION: mutant sequence

<400> SEQUENCE: 80

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Thr
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
```

```
                        245                 250                 255
Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
        290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 81
<211> LENGTH: 458
<212> TYPE: PRT
<213> ORGANISM: Artificial
<220> FEATURE:
<223> OTHER INFORMATION: mutant sequence

<400> SEQUENCE: 81

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
                20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Val
        50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
```

```
        145                 150                 155                 160
Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
        210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
        290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 82
<211> LENGTH: 458
<212> TYPE: PRT
<213> ORGANISM: Artificial
<220> FEATURE:
<223> OTHER INFORMATION: mutant sequence

<400> SEQUENCE: 82

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
```

50                  55                  60
Asp Met Asp Leu Lys Asn Arg Tyr Gly Arg Phe Glu Leu Asp Ser Glu
 65                  70                  75                  80

Ser Ala Ala Val Gly Gly Ile Thr Thr Ile Ile Glu Met Pro Ile Thr
                     85                  90                  95

Phe Pro Pro Thr Thr Thr Leu Asp Ala Phe Leu Glu Lys Lys Lys Gln
                    100                 105                 110

Ala Gly Gln Arg Leu Lys Val Asp Phe Ala Leu Tyr Gly Gly Gly Val
                115                 120                 125

Pro Gly Asn Leu Pro Glu Ile Arg Lys Met His Asp Ala Gly Ala Val
                130                 135                 140

Gly Phe Lys Ser Met Met Ala Ala Ser Ser Pro Gly Met Phe Asp Ala
145                 150                 155                 160

Val Ser Asp Gly Glu Leu Phe Glu Ile Phe Gln Glu Ile Ala Ala Cys
                    165                 170                 175

Gly Ser Val Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
                210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                    245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
                275                 280                 285

Arg Ser Ala Glu Met Asn Val Arg Leu Trp Glu Gln Leu Glu Asn Gly
                290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                    325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
                370                 375                 380

Ser Asp Ala Asp Leu Leu Ile Leu Asp Leu Ile Asp Thr Lys Val
385                 390                 395                 400

Asp Ala Ser Gln Phe Arg Ser Leu His Lys Tyr Ser Pro Phe Asp Gly
                    405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455

<210> SEQ ID NO 83

<211> LENGTH: 458
<212> TYPE: PRT
<213> ORGANISM: Artificial
<220> FEATURE:
<223> OTHER INFORMATION: mutant sequence

<400> SEQUENCE: 83

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Ala Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

```
Ser Asp Ala Asp Leu Leu Ile Leu Asp Leu Asp Ile Asp Ala Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg Leu Asp Tyr Glu Ala Ser Lys
            450                 455

<210> SEQ ID NO 84
<211> LENGTH: 458
<212> TYPE: PRT
<213> ORGANISM: Artificial
<220> FEATURE:
<223> OTHER INFORMATION: mutant sequence

<400> SEQUENCE: 84

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Ile
        50                  55                  60

Asp Met Asp Leu Lys Asn Arg Tyr Gly Arg Phe Glu Leu Asp Ser Glu
65              70                  75                  80

Ser Ala Ala Val Gly Gly Ile Thr Thr Ile Ile Glu Met Pro Ile Thr
            85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
            130                 135                 140

Gly Phe Lys Ser Met Met Ala Ser Ser Ile Pro Gly Met Phe Asp Ala
145                 150                 155                 160

Val Ser Asp Gly Glu Leu Phe Glu Ile Phe Gln Glu Ile Ala Ala Cys
            165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
            245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
            275                 280                 285
```

```
Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
    450                 455

<210> SEQ ID NO 85
<211> LENGTH: 458
<212> TYPE: PRT
<213> ORGANISM: Artificial
<220> FEATURE:
<223> OTHER INFORMATION: mutant sequence

<400> SEQUENCE: 85

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190
```

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
        210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 86
<211> LENGTH: 458
<212> TYPE: PRT
<213> ORGANISM: Artificial
<220> FEATURE:
<223> OTHER INFORMATION: mutant sequence

<400> SEQUENCE: 86

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60

Asp Met Asp Leu Lys Asn Val Asn Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 87
<211> LENGTH: 458
<212> TYPE: PRT
<213> ORGANISM: Artificial
<220> FEATURE:
<223> OTHER INFORMATION: mutant sequence

<400> SEQUENCE: 87

-continued

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
                20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Ile
        50                  55                  60

Asp Met Asp Leu Lys Asn Val Asn Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
        130                 135                 140

Gly Phe Lys Ser Met Met Ala Cys Ser Ser Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Ala Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415
```

```
Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
    450                 455

<210> SEQ ID NO 88
<211> LENGTH: 458
<212> TYPE: PRT
<213> ORGANISM: Artificial
<220> FEATURE:
<223> OTHER INFORMATION: mutant sequence

<400> SEQUENCE: 88

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
                20                  25                  30

Ser Ser Asp Thr Ser Asp Val Glu Ala Ser Arg Thr Ile Asp Ala Gly
                35                  40                  45

Gly Lys Phe Val Met Pro Gly Val Val Asp Glu His Val His Ile Ile
    50                  55                  60

Asp Met Asp Leu Lys Asn Asp Asn Gly Arg Phe Glu Leu Asp Ser Glu
65              70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
                115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
    275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320
```

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455

<210> SEQ ID NO 89
<211> LENGTH: 458
<212> TYPE: PRT
<213> ORGANISM: Artificial
<220> FEATURE:
<223> OTHER INFORMATION: mutant sequence

<400> SEQUENCE: 89

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Ile
50                  55                  60

Asp Met Asp Leu Lys Asn Tyr Asn Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
210                 215                 220

```
Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
            245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
            290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455

<210> SEQ ID NO 90
<211> LENGTH: 458
<212> TYPE: PRT
<213> ORGANISM: Artificial
<220> FEATURE:
<223> OTHER INFORMATION: mutant sequence

<400> SEQUENCE: 90

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Cys
50                  55                  60

Asp Met Asp Leu Lys Asn Ile Asn Gly Arg Phe Glu Leu Asp Ser Glu
65                  70                  75                  80

Ser Ala Ala Val Gly Gly Ile Thr Thr Ile Ile Glu Met Pro Ile Thr
            85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
            115                 120                 125
```

```
Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
                275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Val Leu Val Glu Gln Gly Phe Gly Gln Phe
    435                 440                 445

Val Thr Arg His Asp Tyr Glu Ala Ser Lys
    450                 455

<210> SEQ ID NO 91
<211> LENGTH: 458
<212> TYPE: PRT
<213> ORGANISM: Artificial
<220> FEATURE:
<223> OTHER INFORMATION: mutant sequence

<400> SEQUENCE: 91

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
                20                  25                  30
```

```
Ser Ser Asp Thr Ser Asp Val Glu Ala Ser Arg Thr Ile Asp Ala Gly
         35                  40                  45
Gly Lys Phe Val Met Pro Gly Val Val Asp Glu His Val His Ile Cys
 50                  55                  60
Asp Met Asp Leu Lys Asn Tyr Asn Gly Arg Phe Glu Leu Asp Ser Glu
 65                  70                  75                  80
Ser Ala Ala Val Gly Gly Ile Thr Thr Ile Glu Met Pro Ile Thr
                 85                  90                  95
Phe Pro Pro Thr Thr Thr Leu Asp Ala Phe Leu Glu Lys Lys Lys Gln
                100                 105                 110
Ala Gly Gln Arg Leu Lys Val Asp Phe Ala Leu Tyr Gly Gly Gly Val
        115                 120                 125
Pro Gly Asn Leu Pro Glu Ile Arg Lys Met His Asp Ala Gly Ala Val
    130                 135                 140
Gly Phe Lys Ser Met Met Ala Ser Ser Val Pro Gly Met Phe Asp Ala
145                 150                 155                 160
Val Ser Asp Gly Glu Leu Phe Glu Ile Phe Gln Glu Ile Ala Ala Cys
                165                 170                 175
Gly Ser Val Val Val Val His Ala Glu Asn Glu Thr Ile Ile Gln Ala
            180                 185                 190
Leu Gln Lys Gln Ile Lys Ala Ala Gly Arg Lys Asp Met Ala Ala Tyr
        195                 200                 205
Glu Ala Ser Gln Pro Val Phe Gln Glu Asn Glu Ala Ile Gln Arg Ala
    210                 215                 220
Leu Leu Leu Gln Lys Glu Ala Gly Cys Arg Leu Ile Val Leu His Val
225                 230                 235                 240
Ser Asn Pro Asp Gly Val Glu Leu Ile His Gln Ala Gln Ser Glu Gly
                245                 250                 255
Gln Asp Val His Cys Glu Ser Gly Pro Gln Tyr Leu Asn Ile Thr Thr
            260                 265                 270
Asp Asp Ala Glu Arg Ile Gly Pro Tyr Met Lys Val Ala Pro Pro Val
        275                 280                 285
Arg Ser Ala Glu Met Asn Val Arg Leu Trp Glu Gln Leu Glu Asn Gly
    290                 295                 300
Leu Ile Asp Thr Leu Gly Ser Asp His Gly Gly His Pro Val Glu Asp
305                 310                 315                 320
Lys Glu Pro Gly Trp Lys Asp Val Trp Lys Ala Gly Asn Gly Ala Leu
                325                 330                 335
Gly Leu Glu Thr Ser Leu Pro Met Met Leu Thr Asn Gly Val Asn Lys
            340                 345                 350
Gly Arg Leu Ser Leu Glu Arg Leu Val Glu Val Met Cys Glu Lys Pro
        355                 360                 365
Ala Lys Leu Phe Gly Ile Tyr Pro Gln Lys Gly Thr Leu Gln Val Gly
    370                 375                 380
Ser Asp Ala Asp Leu Leu Ile Leu Asp Leu Asp Ile Asp Thr Lys Val
385                 390                 395                 400
Asp Ala Ser Gln Phe Arg Ser Leu His Lys Tyr Ser Pro Phe Asp Gly
                405                 410                 415
Met Pro Val Thr Gly Ala Pro Val Leu Thr Met Val Arg Gly Thr Val
            420                 425                 430
Val Ala Glu Lys Gly Glu Val Leu Val Glu Gln Gly Phe Gly Gln Phe
        435                 440                 445
Val Thr Arg His Asp Tyr Glu Ala Ser Lys
```

```
                   450                 455

<210> SEQ ID NO 92
<211> LENGTH: 458
<212> TYPE: PRT
<213> ORGANISM: Artificial
<220> FEATURE:
<223> OTHER INFORMATION: mutant sequence

<400> SEQUENCE: 92

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
```

```
                  355                 360                 365
Ala Lys Leu Phe Gly Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                    405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
450                 455

<210> SEQ ID NO 93
<211> LENGTH: 458
<212> TYPE: PRT
<213> ORGANISM: Artificial
<220> FEATURE:
<223> OTHER INFORMATION: mutant sequence

<400> SEQUENCE: 93

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
                20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Cys
        50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
        130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
```

```
                260               265               270
Asp Asp Ala Glu Arg Ile Gly Pro Tyr Met Lys Val Ala Pro Pro Val
            275               280               285

Arg Ser Ala Glu Met Asn Val Arg Leu Trp Glu Gln Leu Glu Asn Gly
        290               295               300

Leu Ile Asp Thr Leu Gly Ser Asp His Gly His Pro Val Glu Asp
305             310               315               320

Lys Glu Pro Gly Trp Lys Asp Val Trp Lys Ala Gly Asn Gly Ala Leu
                325               330               335

Gly Leu Glu Thr Ser Leu Pro Met Met Leu Thr Asn Gly Val Asn Lys
            340               345               350

Gly Arg Leu Ser Leu Glu Arg Leu Val Glu Val Met Cys Glu Lys Pro
        355               360               365

Ala Lys Leu Phe Gly Ile Tyr Pro Gln Lys Gly Thr Leu Gln Val Gly
            370               375               380

Ser Asp Ala Asp Leu Leu Ile Leu Asp Leu Asp Ile Asp Thr Lys Val
385             390               395               400

Asp Ala Ser Gln Phe Arg Ser Leu His Lys Tyr Ser Pro Phe Asp Gly
                405               410               415

Met Pro Val Thr Gly Ala Pro Val Leu Thr Met Val Arg Gly Thr Val
            420               425               430

Val Ala Glu Lys Gly Glu Val Leu Val Glu Gln Gly Phe Gly Gln Leu
        435               440               445

Val Thr Arg His Asp Tyr Glu Ala Ser Lys
    450               455

<210> SEQ ID NO 94
<211> LENGTH: 458
<212> TYPE: PRT
<213> ORGANISM: Artificial
<220> FEATURE:
<223> OTHER INFORMATION: mutant sequence

<400> SEQUENCE: 94

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
```

```
                    165                 170                 175
Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
            290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Val Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455

<210> SEQ ID NO 95
<211> LENGTH: 458
<212> TYPE: PRT
<213> ORGANISM: Artificial
<220> FEATURE:
<223> OTHER INFORMATION: mutant sequence

<400> SEQUENCE: 95

Met Phe Asp Val Ile Val Lys Asn Cys Arg Met Val Ser Gly Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Cys
        50                  55                  60

Asp Met Asp Leu Lys Asn Asp His Gly Arg Phe Glu Leu Asp Ser Glu
```

```
                65                  70                  75                  80
        Ser Ala Ala Val Gly Gly Ile Thr Thr Ile Ile Glu Met Pro Ile Thr
                            85                  90                  95

Phe Pro Pro Thr Thr Thr Leu Asp Ala Phe Leu Glu Lys Lys Lys Gln
                        100                 105                 110

Ala Gly Gln Arg Leu Lys Val Asp Phe Ala Leu Tyr Gly Gly Gly Val
                    115                 120                 125

Pro Gly Asn Leu Pro Glu Ile Arg Lys Met His Asp Ala Gly Ala Val
                130                 135                 140

Gly Phe Lys Ser Met Met Ala Ser Ser Val Pro Gly Met Phe Asp Ala
        145                 150                 155                 160

Val Ser Asp Gly Glu Leu Phe Glu Ile Phe Gln Glu Ile Ala Ala Cys
                        165                 170                 175

Gly Ser Val Val Val His Ala Glu Asn Glu Thr Ile Ile Gln Ala
                    180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
        225                 230                 235                 240

Ser Asn Pro Asp Gly Val Glu Leu Ile His Gln Ala Gln Ser Glu Gly
                        245                 250                 255

Gln Asp Val His Cys Glu Ser Gly Pro Gln Tyr Leu Asn Ile Thr Thr
                    260                 265                 270

Asp Asp Ala Glu Arg Ile Gly Pro Tyr Met Lys Val Ala Pro Pro Val
                275                 280                 285

Arg Ser Ala Glu Met Asn Val Arg Leu Trp Glu Gln Leu Glu Asn Gly
            290                 295                 300

Leu Ile Asp Thr Leu Gly Ser Asp His Gly Gly His Pro Val Glu Asp
        305                 310                 315                 320

Lys Glu Pro Gly Trp Lys Asp Val Trp Lys Ala Gly Asn Gly Ala Leu
                        325                 330                 335

Gly Leu Glu Thr Ser Leu Pro Met Met Leu Thr Asn Gly Val Asn Lys
                    340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
        385                 390                 395                 400

Asp Ala Ser Gln Phe Arg Ser Leu His Lys Tyr Ser Pro Phe Asp Gly
                        405                 410                 415

Met Pro Val Thr Gly Ala Pro Val Leu Thr Met Val Arg Gly Thr Val
                    420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
            450                 455

<210> SEQ ID NO 96
<211> LENGTH: 458
<212> TYPE: PRT
<213> ORGANISM: Artificial
```

<220> FEATURE:
<223> OTHER INFORMATION: mutant sequence

<400> SEQUENCE: 96

```
Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Arg Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400
```

```
Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 97
<211> LENGTH: 458
<212> TYPE: PRT
<213> ORGANISM: Artificial
<220> FEATURE:
<223> OTHER INFORMATION: mutant sequence

<400> SEQUENCE: 97

Met Phe Asp Val Ile Val Lys Asn Cys Arg Met Val Ser Gly Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300
```

```
Leu Ile Asp Thr Leu Gly Ser Asp His Gly Gly His Pro Ala Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 98
<211> LENGTH: 458
<212> TYPE: PRT
<213> ORGANISM: Artificial
<220> FEATURE:
<223> OTHER INFORMATION: mutant sequence

<400> SEQUENCE: 98

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Arg Asp Val Glu Ala Ser Arg Thr Ile Asp Ala Gly
        35                  40                  45

Gly Lys Phe Val Met Pro Gly Val Val Asp Glu His Val His Ile Cys
50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
            85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
            165                 170                 175

Gly Ser Val Val Val Val His Ala Glu Asn Glu Thr Ile Ile Gln Ala
        180                 185                 190

Leu Gln Lys Gln Ile Lys Ala Ala Gly Arg Lys Asp Met Ala Ala Tyr
    195                 200                 205
```

```
Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Lys Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 99
<211> LENGTH: 458
<212> TYPE: PRT
<213> ORGANISM: Artificial
<220> FEATURE:
<223> OTHER INFORMATION: mutant sequence

<400> SEQUENCE: 99

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Arg Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110
```

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
        130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Ser Gly
290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Arg Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 100
<211> LENGTH: 458
<212> TYPE: PRT
<213> ORGANISM: Artificial
<220> FEATURE:
<223> OTHER INFORMATION: mutant sequence

<400> SEQUENCE: 100

Met Phe Asp Val Ile Val Lys Asn Cys Arg Met Val Ser Gly Asp Gly
1               5                   10                  15

-continued

```
Ile Thr Glu Ala Asp Ile Leu Val Lys Asp Gly Lys Val Ala Ala Ile
         20                  25                  30

Ser Ser Asp Thr Ser Asp Val Glu Ala Ser Arg Thr Ile Asp Ala Gly
         35                  40                  45

Gly Lys Phe Val Met Pro Gly Val Val Asp Glu His Val His Ile Cys
 50                  55                  60

Asp Met Asp Leu Lys Asp Asp His Gly Arg Phe Glu Leu Asp Ser Glu
 65                  70                  75                  80

Ser Ala Ala Val Gly Gly Ile Thr Thr Ile Glu Met Pro Ile Thr
                 85                  90                  95

Phe Pro Pro Thr Thr Thr Leu Asp Ala Phe Leu Glu Lys Lys Gln
             100                 105                 110

Ala Gly Gln Arg Leu Lys Val Asp Phe Ala Leu Tyr Gly Gly Gly Val
             115                 120                 125

Pro Gly Asn Leu Pro Glu Ile Arg Lys Met His Asp Ala Gly Ala Val
 130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                 165                 170                 175

Gly Ser Val Val Val His Ala Glu Asn Glu Thr Ile Ile Gln Ala
             180                 185                 190

Leu Gln Lys Gln Ile Lys Ala Ala Gly Arg Lys Asp Met Ala Ala Tyr
             195                 200                 205

Glu Ala Ser Gln Pro Val Phe Gln Glu Asn Glu Ala Ile Gln Arg Ala
     210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
             245                 250                 255

Gln Asp Val His Cys Glu Ser Gly Pro Gln Tyr Leu Asn Ile Thr Thr
             260                 265                 270

Asp Asp Ala Glu Arg Ile Gly Pro Tyr Met Lys Val Ala Pro Pro Val
             275                 280                 285

Arg Ser Ala Glu Met Asn Val Arg Leu Trp Glu Gln Leu Glu Asn Gly
 290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                 325                 330                 335

Gly Leu Glu Thr Ser Leu Pro Met Met Leu Thr Asn Gly Val Asn Lys
             340                 345                 350

Gly Arg Leu Ser Leu Glu Arg Leu Val Glu Val Met Cys Glu Lys Pro
             355                 360                 365

Ala Lys Leu Phe Gly Ile Tyr Pro Gln Lys Gly Thr Leu Gln Val Gly
             370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
             405                 410                 415

Met Pro Val Thr Gly Ala Pro Val Leu Thr Met Val Arg Gly Thr Val
             420                 425                 430
```

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455

<210> SEQ ID NO 101
<211> LENGTH: 458
<212> TYPE: PRT
<213> ORGANISM: Artificial
<220> FEATURE:
<223> OTHER INFORMATION: mutant sequence

<400> SEQUENCE: 101

Met Phe Asp Val Ile Val Lys Asn Cys Arg Met Val Ser Gly Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Ala Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

```
Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
            450                 455

<210> SEQ ID NO 102
<211> LENGTH: 458
<212> TYPE: PRT
<213> ORGANISM: Artificial
<220> FEATURE:
<223> OTHER INFORMATION: mutant sequence

<400> SEQUENCE: 102

Met Phe Asp Val Ile Val Lys Asn Cys Arg Met Val Ser Ser Asp Gly
1               5                   10                  15

Ile Thr Glu Ala Asp Ile Leu Val Lys Asp Gly Lys Val Ala Ala Ile
            20                  25                  30

Ser Ser Asp Thr Gly Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240
```

```
Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
            290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
                370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455

<210> SEQ ID NO 103
<211> LENGTH: 458
<212> TYPE: PRT
<213> ORGANISM: Artificial
<220> FEATURE:
<223> OTHER INFORMATION: mutant sequence

<400> SEQUENCE: 103

Met Phe Asp Val Ile Val Lys Asn Cys Arg Met Val Ser Ala Asp Gly
1               5                   10                  15

Ile Thr Glu Ala Asp Ile Leu Val Lys Asp Gly Lys Val Ala Ala Ile
                20                  25                  30

Ser Ser Asp Thr Gly Asp Val Glu Ala Ser Arg Thr Ile Asp Ala Gly
            35                  40                  45

Gly Lys Phe Val Met Pro Gly Val Val Asp Glu His Val His Ile Cys
        50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
        130                 135                 140
```

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
        210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
        450                 455

<210> SEQ ID NO 104
<211> LENGTH: 458
<212> TYPE: PRT
<213> ORGANISM: Artificial
<220> FEATURE:
<223> OTHER INFORMATION: mutant sequence

<400> SEQUENCE: 104

Met Phe Asp Val Ile Val Lys Asn Cys Arg Met Val Ser Val Asp Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

-continued

```
Gly Lys Phe Val Met Pro Gly Val Asp Glu His Val His Ile Cys
 50                  55                  60

Asp Met Asp Leu Lys Asn Asp His Gly Arg Phe Glu Leu Asp Ser Glu
 65                  70                  75                  80

Ser Ala Ala Val Gly Gly Ile Thr Thr Ile Ile Glu Met Pro Ile Thr
                     85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
                115                 120                 125

Pro Gly Asn Leu Pro Glu Ile Arg Lys Met His Asp Ala Gly Ala Val
130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
                275                 280                 285

Arg Ser Ala Glu Met Asn Val Arg Leu Trp Glu Gln Leu Glu Asn Gly
                290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
450                 455
```

```
<210> SEQ ID NO 105
<211> LENGTH: 458
<212> TYPE: PRT
<213> ORGANISM: Artificial
<220> FEATURE:
<223> OTHER INFORMATION: mutant sequence

<400> SEQUENCE: 105

Met Phe Asp Val Ile Val Lys Asn Cys Arg Met Val Ser Gly Asp Gly
1               5                   10                  15

Ile Thr Glu Ala Asp Ile Leu Val Lys Asp Gly Lys Val Ala Ala Ile
            20                  25                  30

Ser Ser Asp Thr Gly Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Glu Met Pro Ile Thr
                85                  90                  95

Phe Pro Pro Thr Thr Thr Leu Asp Ala Phe Leu Glu Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
```

```
            370                 375                 380
Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455

<210> SEQ ID NO 106
<211> LENGTH: 458
<212> TYPE: PRT
<213> ORGANISM: Artificial
<220> FEATURE:
<223> OTHER INFORMATION: mutant sequence

<400> SEQUENCE: 106

Met Phe Asp Val Ile Val Lys Asn Cys Arg Met Val Ser Ala Asp Gly
1               5                   10                  15

Ile Thr Glu Ala Asp Ile Leu Val Lys Asp Gly Lys Val Ala Ala Ile
                20                  25                  30

Ser Ser Asp Thr Trp Asp Val Glu Ala Ser Arg Thr Ile Asp Ala Gly
            35                  40                  45

Gly Lys Phe Val Met Pro Gly Val Val Asp Glu His Val His Ile Cys
50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
                115                 120                 125

Pro Gly Asn Leu Pro Glu Ile Arg Lys Met His Asp Ala Gly Ala Val
            130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
```

```
            275                 280                 285
Arg Ser Ala Glu Met Asn Val Arg Leu Trp Glu Gln Leu Glu Asn Gly
290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 107
<211> LENGTH: 458
<212> TYPE: PRT
<213> ORGANISM: Artificial
<220> FEATURE:
<223> OTHER INFORMATION: mutant sequence

<400> SEQUENCE: 107

Met Phe Asp Val Ile Val Lys Asn Cys Arg Met Val Ser Ala Asp Gly
1               5                   10                  15

Ile Thr Glu Ala Asp Ile Leu Val Lys Asp Gly Lys Val Ala Ala Ile
            20                  25                  30

Ser Ser Asp Thr Val Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
```

```
                180             185              190
Leu Gln Lys Gln Ile Lys Ala Ala Gly Arg Lys Asp Met Ala Ala Tyr
            195                 200             205
Glu Ala Ser Gln Pro Val Phe Gln Glu Asn Glu Ala Ile Gln Arg Ala
            210                 215             220
Leu Leu Leu Gln Lys Glu Ala Gly Cys Arg Leu Ile Val Leu His Val
225                 230                 235             240
Ser Asn Pro Asp Gly Val Glu Leu Ile His Gln Ala Gln Ser Glu Gly
                245                 250             255
Gln Asp Val His Cys Glu Ser Gly Pro Gln Tyr Leu Asn Ile Thr Thr
            260                 265             270
Asp Asp Ala Glu Arg Ile Gly Pro Tyr Met Lys Val Ala Pro Pro Val
            275                 280             285
Arg Ser Ala Glu Met Asn Val Arg Leu Trp Glu Gln Leu Glu Asn Gly
            290                 295             300
Leu Ile Asp Thr Leu Gly Ser Asp His Gly Gly His Pro Val Glu Asp
305                 310                 315             320
Lys Glu Pro Gly Trp Lys Asp Val Trp Lys Ala Gly Asn Gly Ala Leu
                325                 330             335
Gly Leu Glu Thr Ser Leu Pro Met Met Leu Thr Asn Gly Val Asn Lys
            340                 345             350
Gly Arg Leu Ser Leu Glu Arg Leu Val Glu Val Met Cys Glu Lys Pro
            355                 360             365
Ala Lys Leu Phe Gly Ile Tyr Pro Gln Lys Gly Thr Leu Gln Val Gly
            370                 375             380
Ser Asp Ala Asp Leu Leu Ile Leu Asp Leu Asp Ile Asp Thr Lys Val
385                 390                 395             400
Asp Ala Ser Gln Phe Arg Ser Leu His Lys Tyr Ser Pro Phe Asp Gly
                405                 410             415
Met Pro Val Thr Gly Ala Pro Val Leu Thr Met Val Arg Gly Thr Val
            420                 425             430
Val Ala Glu Lys Gly Glu Val Leu Val Glu Gln Gly Phe Gly Gln Phe
            435                 440             445
Val Thr Arg His Asp Tyr Glu Ala Ser Lys
            450                 455

<210> SEQ ID NO 108
<211> LENGTH: 458
<212> TYPE: PRT
<213> ORGANISM: Artificial
<220> FEATURE:
<223> OTHER INFORMATION: mutant sequence

<400> SEQUENCE: 108

Met Phe Asp Val Ile Val Lys Asn Cys Arg Met Val Ser Ser Asn Gly
1               5                   10              15
Ile Thr Glu Ala Asp Ile Leu Val Lys Asp Gly Lys Val Ala Ala Ile
            20                  25              30
Ser Ser Asp Thr Ser Asp Val Glu Ala Ser Arg Thr Ile Asp Ala Gly
            35                  40              45
Gly Lys Phe Val Met Pro Gly Val Val Asp Glu His Val His Ile Cys
        50                  55              60
Asp Met Asp Leu Lys Asn Asp His Gly Arg Phe Glu Leu Asp Ser Glu
65              70                  75              80
Ser Ala Ala Val Gly Gly Ile Thr Thr Ile Ile Glu Met Pro Ile Thr
```

```
            85                  90                  95
Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
            130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                    165                 170                 175

Gly Ser Val Val Val His Ala Glu Asn Glu Thr Ile Ile Gln Ala
                    180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                    245                 250                 255

Gln Asp Val His Cys Glu Ser Gly Pro Gln Tyr Leu Asn Ile Thr Thr
                    260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
            290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                    325                 330                 335

Gly Leu Glu Thr Ser Leu Pro Met Met Leu Thr Asn Gly Val Asn Lys
                    340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                    405                 410                 415

Met Pro Val Thr Gly Ala Pro Val Leu Thr Met Val Arg Gly Thr Val
                    420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455

<210> SEQ ID NO 109
<211> LENGTH: 458
<212> TYPE: PRT
<213> ORGANISM: Artificial
<220> FEATURE:
<223> OTHER INFORMATION: mutant sequence
```

<400> SEQUENCE: 109

Met Phe Asp Val Ile Val Lys Asn Cys Arg Met Val Ser Val Asp Gly
1               5                   10                  15

Ile Thr Glu Ala Asp Ile Leu Val Lys Asp Gly Lys Val Ala Ala Ile
            20                  25                  30

Ser Ser Asp Thr Arg Asp Val Glu Ala Ser Arg Thr Ile Asp Ala Gly
        35                  40                  45

Gly Lys Phe Val Met Pro Gly Val Val Asp Glu His Val His Ile Cys
50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

```
Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455

<210> SEQ ID NO 110
<211> LENGTH: 458
<212> TYPE: PRT
<213> ORGANISM: Artificial
<220> FEATURE:
<223> OTHER INFORMATION: mutant sequence

<400> SEQUENCE: 110

Met Phe Asp Val Ile Val Lys Asn Cys Arg Met Val Ser Ser Asn Gly
1               5                   10                  15

Ile Thr Glu Ala Asp Ile Leu Val Lys Asp Gly Lys Val Ala Ala Ile
            20                  25                  30

Ser Ser Asp Thr Ser Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Cys Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Gly Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320
```

```
Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455

<210> SEQ ID NO 111
<211> LENGTH: 458
<212> TYPE: PRT
<213> ORGANISM: Artificial
<220> FEATURE:
<223> OTHER INFORMATION: mutant sequence

<400> SEQUENCE: 111

Met Phe Asp Val Ile Val Lys Asn Cys Arg Met Val Ser Ser Asn Gly
1               5                   10                  15

Ile Thr Glu Ala Asp Ile Leu Val Lys Asp Gly Lys Val Ala Ala Ile
                20                  25                  30

Ser Ser Asp Thr Ser Asp Val Glu Ala Ser Arg Thr Ile Asp Ala Gly
            35                  40                  45

Gly Lys Phe Val Met Pro Gly Val Val Asp Glu His Val His Ile Cys
        50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
        130                 135                 140

Gly Phe Lys Ser Met Met Ala Ser Ser Ile Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
        210                 215                 220
```

```
Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
            245                 250                 255

Gln Asp Val His Cys Glu Ser Gly Pro Gln Tyr Leu Asn Ile Thr Thr
        260                 265                 270

Asp Asp Ala Glu Arg Ile Gly Pro Tyr Met Lys Val Ala Pro Pro Val
    275                 280                 285

Arg Ser Ala Glu Met Asn Val Arg Leu Trp Glu Gln Leu Glu Asn Gly
290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 112
<211> LENGTH: 458
<212> TYPE: PRT
<213> ORGANISM: Artificial
<220> FEATURE:
<223> OTHER INFORMATION: mutant sequence

<400> SEQUENCE: 112

Met Phe Asp Val Ile Val Lys Asn Cys Arg Met Val Ser Pro Gly Gly
1               5                   10                  15

Ile Thr Glu Ala Asp Ile Leu Val Lys Asp Gly Lys Val Ala Ala Ile
            20                  25                  30

Ser Ser Asp Thr Gly Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65              70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125
```

```
Pro Gly Asn Leu Pro Glu Ile Arg Lys Met His Asp Ala Gly Ala Val
            130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455
```

<210> SEQ ID NO 113
<211> LENGTH: 458
<212> TYPE: PRT
<213> ORGANISM: Artificial
<220> FEATURE:
<223> OTHER INFORMATION: mutant sequence

<400> SEQUENCE: 113

```
Met Phe Asp Val Ile Val Lys Asn Cys Arg Met Val Ser Gly Arg Gly
1               5                   10                  15

Ile Thr Glu Ala Asp Ile Leu Val Lys Asp Gly Lys Val Ala Ala Ile
            20                  25                  30
```

```
Ser Ser Asp Thr Gly Asp Val Glu Ala Ser Arg Thr Ile Asp Ala Gly
        35              40                  45

Gly Lys Phe Val Met Pro Gly Val Val Asp Glu His Val His Ile Cys
 50                  55                  60

Asp Met Asp Leu Lys Asn Asp His Gly Arg Phe Glu Leu Asp Ser Glu
 65              70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
            130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Gln Leu Glu Asn Gly
            290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
            325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445
```

Val Thr Arg His Asp Tyr Glu Ala Ser Lys
    450                 455

<210> SEQ ID NO 114
<211> LENGTH: 458
<212> TYPE: PRT
<213> ORGANISM: Artificial
<220> FEATURE:
<223> OTHER INFORMATION: mutant sequence

<400> SEQUENCE: 114

Met Phe Asp Val Ile Val Lys Asn Cys Arg Met Val Ser Gly Gln Gly
1               5                   10                  15

Ile Thr Glu Ala Asp Ile Leu Val Lys Asp Gly Lys Val Ala Ala Ile
            20                  25                  30

Ser Ser Asp Thr Gly Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

```
Gly Arg Leu Ser Leu Glu Arg Leu Val Glu Val Met Cys Glu Lys Pro
            355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
        450                 455

<210> SEQ ID NO 115
<211> LENGTH: 458
<212> TYPE: PRT
<213> ORGANISM: Artificial
<220> FEATURE:
<223> OTHER INFORMATION: mutant sequence

<400> SEQUENCE: 115

Met Phe Asp Val Ile Val Lys Asn Cys Arg Met Val Ser Phe Ala Gly
1               5                   10                  15

Ile Thr Glu Ala Asp Ile Leu Val Lys Asp Gly Lys Val Ala Ala Ile
            20                  25                  30

Ser Ser Asp Thr Gly Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255
```

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
        290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 116
<211> LENGTH: 458
<212> TYPE: PRT
<213> ORGANISM: Artificial
<220> FEATURE:
<223> OTHER INFORMATION: mutant sequence

<400> SEQUENCE: 116

Met Phe Asp Val Ile Val Lys Asn Cys Arg Met Val Ser Ser Ser Gly
1               5                   10                  15

Ile Thr Glu Ala Asp Ile Leu Val Lys Asp Gly Lys Val Ala Ala Ile
            20                  25                  30

Ser Ser Asp Thr Gly Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
            85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

```
Val Ser Asp Gly Glu Leu Phe Glu Ile Phe Gln Glu Ile Ala Ala Cys
            165                 170                 175

Gly Ser Val Val Val His Ala Glu Asn Glu Thr Ile Ile Gln Ala
        180                 185                 190

Leu Gln Lys Gln Ile Lys Ala Ala Gly Arg Lys Asp Met Ala Ala Tyr
            195                 200                 205

Glu Ala Ser Gln Pro Val Phe Gln Glu Asn Glu Ala Ile Gln Arg Ala
            210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
        290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455

<210> SEQ ID NO 117
<211> LENGTH: 458
<212> TYPE: PRT
<213> ORGANISM: Artificial
<220> FEATURE:
<223> OTHER INFORMATION: mutant sequence

<400> SEQUENCE: 117

Met Phe Asp Val Ile Val Lys Asn Cys Arg Met Val Ser Pro Gly Gly
1               5                   10                  15

Ile Thr Glu Ala Asp Ile Leu Val Lys Asp Gly Lys Val Ala Ala Ile
            20                  25                  30

Ser Ser Asp Thr Gly Asp Val Glu Ala Ser Arg Thr Ile Asp Ala Gly
        35                  40                  45

Gly Lys Phe Val Met Pro Gly Val Val Asp Glu His Val His Ile Ile
    50                  55                  60
```

Asp Met Asp Leu Lys Asn Asp His Gly Arg Phe Glu Leu Asp Ser Glu
65                  70                  75                  80

Ser Ala Ala Val Gly Gly Ile Thr Thr Ile Glu Met Pro Ile Thr
            85                  90                  95

Phe Pro Pro Thr Thr Thr Leu Asp Ala Phe Leu Glu Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ser Ser Val Pro Gly Met Phe Asp Ala
145                 150                 155                 160

Val Ser Asp Gly Glu Leu Phe Glu Ile Phe Gln Glu Ile Ala Ala Cys
            165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
            245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
            325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455

<210> SEQ ID NO 118
<211> LENGTH: 458
<212> TYPE: PRT

<213> ORGANISM: Artificial
<220> FEATURE:
<223> OTHER INFORMATION: mutant sequence

<400> SEQUENCE: 118

```
Met Phe Asp Val Ile Val Lys Asn Cys Arg Met Val Ser Pro Gly Gly
1               5                   10                  15

Ile Thr Glu Ala Asp Ile Leu Val Lys Asp Gly Lys Val Ala Ala Ile
            20                  25                  30

Ser Ser Asp Thr Gly Asp Val Glu Ala Ser Arg Thr Ile Asp Ala Gly
        35                  40                  45

Gly Lys Phe Val Met Pro Gly Val Val Asp Glu His Val His Ile Cys
    50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Asp Ile Asp Thr Lys Val
```

```
        385                 390                 395                 400
Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455

<210> SEQ ID NO 119
<211> LENGTH: 458
<212> TYPE: PRT
<213> ORGANISM: Artificial
<220> FEATURE:
<223> OTHER INFORMATION: mutant sequence

<400> SEQUENCE: 119

Met Phe Asp Val Ile Val Lys Asn Cys Arg Met Val Ser Ser Ser Gly
1               5                   10                  15

Ile Thr Glu Ala Asp Ile Leu Val Lys Asp Gly Lys Val Ala Ala Ile
                20                  25                  30

Ser Ser Asp Thr Gly Asp Val Glu Ala Ser Arg Thr Ile Asp Ala Gly
                35                  40                  45

Gly Lys Phe Val Met Pro Gly Val Val Asp Glu His Val His Ile Cys
            50                  55                  60

Asp Met Asp Leu Lys Asn Asp His Gly Arg Phe Glu Leu Asp Ser Glu
65                  70                  75                  80

Ser Ala Ala Val Gly Gly Ile Thr Thr Ile Ile Glu Met Pro Ile Thr
                85                  90                  95

Phe Pro Pro Thr Thr Thr Leu Asp Ala Phe Leu Glu Lys Lys Lys Gln
                100                 105                 110

Ala Gly Gln Arg Leu Lys Val Asp Phe Ala Leu Tyr Gly Gly Gly Val
                115                 120                 125

Pro Gly Asn Leu Pro Glu Ile Arg Lys Met His Asp Ala Gly Ala Val
                130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
                180                 185                 190

Leu Gln Lys Gln Ile Lys Ala Ala Gly Arg Lys Asp Met Ala Ala Tyr
                195                 200                 205

Glu Ala Ser Gln Pro Val Phe Gln Glu Asn Glu Ala Ile Gln Arg Ala
                210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
                260                 265                 270

Asp Asp Ala Glu Arg Ile Gly Pro Tyr Met Lys Val Ala Pro Pro Val
                275                 280                 285

Arg Ser Ala Glu Met Asn Val Arg Leu Trp Glu Gln Leu Glu Asn Gly
```

```
                290                 295                 300
Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Gly Ile Tyr Pro Gln Lys Gly Thr Leu Gln Val Gly
                370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
450                 455
```